(12) United States Patent
Jeanmart et al.

(10) Patent No.: US 8,530,667 B2
(45) Date of Patent: Sep. 10, 2013

(54) HERBICIDES

(75) Inventors: Stephane André Marie Jeanmart, Bracknell (GB); John Benjamin Taylor, Bracknell (GB); Melloney Tyte, Bracknell (GB); Christopher John Mathews, Bracknell (GB); Stephen Christopher Smith, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 116 days.

(21) Appl. No.: 12/675,975

(22) PCT Filed: Sep. 1, 2008

(86) PCT No.: PCT/EP2008/007132
§ 371 (c)(1),
(2), (4) Date: Jun. 15, 2010

(87) PCT Pub. No.: WO2009/030450
PCT Pub. Date: Mar. 12, 2009

(65) Prior Publication Data
US 2010/0298140 A1    Nov. 25, 2010

(30) Foreign Application Priority Data
Sep. 3, 2007   (GB) .................................. 0717082.2

(51) Int. Cl.
| C07D 293/00 | (2006.01) |
| C07D 277/30 | (2006.01) |
| C07D 409/00 | (2006.01) |
| C07D 307/00 | (2006.01) |
| C07D 333/16 | (2006.01) |
| C07D 405/00 | (2006.01) |
| C07D 239/02 | (2006.01) |

(52) U.S. Cl.
USPC .......... 548/100; 548/204; 546/287.7; 549/60; 549/459; 549/78; 544/318

(58) Field of Classification Search
None
See application file for complete search history.

(56) References Cited

U.S. PATENT DOCUMENTS

| 2005/0164883 A1 | 7/2005 | Maetzke |
| 2012/0021912 A1 | 1/2012 | Mathews et al. |
| 2012/0028800 A1 | 2/2012 | Mathews et al. |
| 2012/0094832 A1 | 4/2012 | Tyte et al. |
| 2012/0142529 A1 | 6/2012 | Tyte et al. |

FOREIGN PATENT DOCUMENTS

| WO | 9603366 | 2/1996 |
| WO | 9948869 | 9/1999 |
| WO | 0174770 | 10/2001 |
| WO | 2004058712 | 7/2004 |
| WO | 2005123667 | 12/2005 |

*Primary Examiner* — Nyeemah A Grazier
(74) *Attorney, Agent, or Firm* — R. Kody Jones

(57) ABSTRACT

Compounds of formula (I) wherein the substituents are as defined in claim 1, are suitable for use as herbicides.

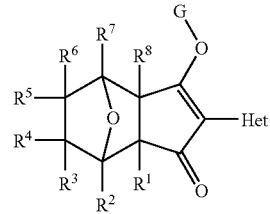

13 Claims, No Drawings

HERBICIDES

This application is a 371 of International Application No. PCT/EP2008/007132 filed Sep. 1, 2008, which claims priority to GB 0717082.2 filed Sep. 3, 2007, the contents of which are incorporated herein by reference.

The present invention relates to novel, herbicidally active cyclopentanedione compounds, and derivatives thereof, to processes for their preparation, to compositions comprising those compounds, and to their use in controlling weeds, especially in crops of useful plants, or in inhibiting undesired plant growth.

Cyclopentanedione compounds having herbicidal action are described, for example, in WO 01/74770 and WO 96/03366.

Novel cyclopentanedione compounds, and derivatives thereof, having herbicidal and growth-inhibiting properties have now been found.

The present invention accordingly relates to compounds of formula (I)

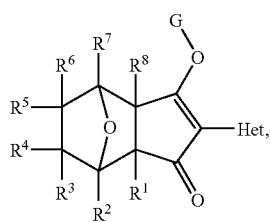

wherein
$R^1$ and $R^8$ are independently of each other hydrogen, $C_1$-$C_3$alkyl, $C_1$-$C_3$haloalkyl, $C_1$-$C_3$alkoxy, $C_1$-$C_3$alkylthio, halogen or $C_1$-$C_6$alkoxycarbonyl,
$R^2$, $R^3$, $R^4$, $R^5$, $R^6$ and $R^7$ are independently of each other hydrogen or a substituent, or
$R^1$ and $R^8$, $R^3$ and $R^4$, or $R^3$ and $R^6$ together with the carbon atoms to which they are attached form an optionally substituted ring, optionally containing a heteroatom, or
$R^3$ and $R^4$ together with the carbon atoms to which they are attached form a keto, imino or alkenyl unit, or
$R^3$ and $R^6$ together form a bond,
G is hydrogen or an alkali metal, alkaline earth metal, sulfonium, ammonium or a latentiating group,
Het is an optionally substituted monocyclic or bicyclic heteroaromatic ring, and agronomically acceptable salts thereof.

In the substituent definitions of the compounds of the formula (I), each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neopentyl. The alkyl groups are suitably $C_1$ to $C_6$ alkyl groups, but are preferably $C_1$-$C_4$ alkyl groups.

Ring forming alkylene, and alkenylene groups can optionally be further substituted by one or more halogen, $C_1$-$C_3$alkyl and/or $C_1$-$C_3$alkoxy groups. When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, $C_3$-$C_7$ cycloalkyl (itself optionally substituted with $C_1$-$C_6$ alkyl or halogen), $C_5$-$C_7$ cycloalkenyl (itself optionally substituted with $C_1$-$C_6$ alkyl or halogen), hydroxy, $C_1$-$C_{10}$ alkoxy, $C_1$-$C_{10}$ alkoxy($C_1$-$C_{10}$) alkoxy, tri($C_1$-$C_4$)alkylsilyl($C_1$-$C_6$)alkoxy, $C_1$-$C_6$ alkoxycarbonyl($C_1$-$C_{10}$)alkoxy, $C_1$-$C_{10}$ haloalkoxy, aryl($C_1$-$C_4$)alkoxy (where the aryl group is optionally substituted), $C_3$-$C_7$ cycloalkyloxy (where the cycloalkyl group is optionally substituted with $C_1$-$C_6$ alkyl or halogen), $C_3$-$C_{10}$ alkenyloxy, $C_3$-$C_{10}$ alkynyloxy, mercapto, $C_1$-$C_{10}$ alkylthio, $C_1$-$C_{10}$ haloalkylthio, aryl($C_1$-$C_4$)alkylthio (where the aryl group is optionally substituted), $C_3$-$C_7$ cycloalkylthio (where the cycloalkyl group is optionally substituted with $C_1$-$C_6$ alkyl or halogen), tri($C_1$-$C_4$)alkylsilyl($C_1$-$C_6$)alkylthio, arylthio (where the aryl group is optionally substituted), $C_1$-$C_6$ alkylsulfonyl, $C_1$-$C_6$ haloalkylsulfonyl, $C_1$-$C_6$ alkylsulfinyl, $C_1$-$C_6$ haloalkylsulfinyl, arylsulfonyl (where the aryl group may be optionally substituted), tri($C_1$-$C_4$)alkylsilyl, aryldi($C_1$-$C_4$) alkylsilyl, ($C_1$-$C_4$)alkyldiarylsilyl, triarylsilyl, aryl($C_1$-$C_4$) alkylthio($C_1$-$C_4$)alkyl, aryloxy($C_1$-$C_4$)alkyl, formyl, $C_1$-$C_{10}$ alkylcarbonyl, $HO_2C$, $C_1$-$C_{10}$ alkoxycarbonyl, aminocarbonyl, $C_1$-$C_6$ alkylaminocarbonyl, di($C_1$-$C_6$ alkyl)aminocarbonyl, N—($C_1$-$C_3$ alkyl)-N—($C_1$-$C_3$ alkoxy)aminocarbonyl, $C_1$-$C_6$ alkylcarbonyloxy, arylcarbonyloxy (where the aryl group is optionally substituted), di($C_1$-$C_6$)alkylaminocarbonyloxy, $C_1$-$C_6$alkyliminooxy, $C_3$-$C_6$alkenyloxyimino, aryloxyimino, aryl (itself optionally substituted), heteroaryl (itself optionally substituted), heterocyclyl (itself optionally substituted with $C_1$-$C_6$ alkyl or halogen), aryloxy (where the aryl group is optionally substituted), heteroaryloxy, (where the heteroaryl group is optionally substituted), heterocyclyloxy (where the heterocyclyl group is optionally substituted with $C_1$-$C_6$ alkyl or halogen), amino, $C_1$-$C_6$ alkylamino, di($C_1$-$C_6$)alkylamino, $C_1$-$C_6$ alkylcarbonylamino, N—($C_1$-$C_6$)alkylcarbonyl-N—($C_1$-$C_6$)alkylamino, $C_2$-$C_6$ alkenylcarbonyl, $C_2$-$C_6$ alkynylcarbonyl, $C_3$-$C_6$ alkenyloxycarbonyl, $C_3$-$C_6$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. It is understood, that allenyl and alkylinylalkenyl are included in these terms.

When present, the optional substituents on alkenyl or alkynyl include those optional substituents given above for an alkyl moiety.

Halogen is fluorine, chlorine, bromine or iodine.

Haloalkyl groups are alkyl groups which are substituted with one or more of the same or different halogen atoms and are, for example, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

In the context of the present specification the terms "aryl", "aromatic ring" and "aromatic ring system" refer to ring systems which may be mono-, bi- or tricyclic. Examples of such rings include phenyl, naphthalenyl, anthracenyl, indenyl or phenanthrenyl. A preferred aryl group is phenyl. In addition, the terms "heteroaryl", "heteroaromatic ring" or "heteroaromatic ring system" refer to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Suitable examples of heteroaromatic rings are, for example, thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, pyridazinyl, triazinyl, oxadiazolyl and thiadiazolyl, and, where appropriate, N-oxides and salts thereof.

The terms heterocycle and heterocyclyl preferably refer to a non-aromatic preferably monocyclic or bicyclic ring systems containing up to 7 atoms including one or more (preferably one or two) heteroatoms selected from O, S and N. Examples of such rings include 1,3-dioxolane, oxetane, tetrahydrofuran, morpholine, thiomorpholin and piperazine.

When present, the optional substituents on heterocyclyl include $C_1$-$C_6$ alkyl and $C_1$-$C_6$ haloalkyl as well as those optional substituents given above for an alkyl moiety.

Cycloalkyl includes preferably cyclopropyl, cyclobutyl, cyclopentyl and cyclohexyl. Cycloalkylalkyl is preferentially cyclopropylmethyl. Cycloalkenyl includes cyclopentenyl and cyclohexenyl.

When present, the optional substituents on cycloalkyl or cycloalkenyl include $C_1$-$C_3$ alkyl as well as those optional substituents given above for an alkyl moiety.

Carbocyclic rings include aryl, cycloalkyl and cycloalkenyl groups.

When present, the optional substituents on aryl or heteroaryl are selected independently, from halogen, nitro, cyano, rhodano, isothiocyanato, $C_1$-$C_6$ alkyl, $C_1$-$C_6$ haloalkyl, $C_1$-$C_6$ alkoxy-($C_1$-$C_6$)alkyl, $C_2$-$C_6$ alkenyl, $C_2$-$C_6$ haloalkenyl, $C_2$-$C_6$ alkynyl, $C_3$-$C_7$ cycloalkyl (itself optionally substituted with $C_1$-$C_6$ alkyl or halogen), $C_5$-$C_7$ cycloalkenyl (itself optionally substituted with $C_1$-$C_6$ alkyl or halogen), hydroxy, $C_1$-$C_{10}$ alkoxy, $C_1$-$C_{10}$ alkoxy($C_1$-$C_{10}$)alkoxy, tri($C_1$-$C_4$)alkylsilyl($C_1$-$C_6$)alkoxy, $C_1$-$C_6$ alkoxycarbonyl($C_1$-$C_{10}$)alkoxy, $C_1$-$C_{10}$ haloalkoxy, aryl($C_1$-$C_4$)alkoxy (where the aryl group is optionally substituted with halogen or $C_1$-$C_6$ alkyl), $C_3$-$C_7$ cycloalkyloxy (where the cycloalkyl group is optionally substituted with $C_1$-$C_6$ alkyl or halogen), $C_3$-$C_{10}$ alkenyloxy, $C_3$-$C_{10}$ alkynyloxy, mercapto, $C_1$-$C_{10}$ alkylthio, $C_1$-$C_{10}$ haloalkylthio, aryl($C_1$-$C_4$)alkylthio, $C_3$-$C_7$ cycloalkylthio (where the cycloalkyl group is optionally substituted with $C_1$-$C_6$ alkyl or halogen), tri($C_1$-$C_4$)-alkylsilyl($C_1$-$C_6$)alkylthio, arylthio, $C_1$-$C_6$ alkylsulfonyl, $C_1$-$C_6$ haloalkylsulfonyl, $C_1$-$C_6$ alkylsulfinyl, $C_1$-$C_6$ haloalkylsulfinyl, arylsulfonyl, tri($C_1$-$C_4$)alkylsilyl, aryldi($C_1$-$C_4$)-alkylsilyl, ($C_1$-$C_4$)alkyldiarylsilyl, triarylsilyl, $C_1$-$C_{10}$ alkylcarbonyl, $HO_2C$, $C_1$-$C_{10}$ alkoxycarbonyl, aminocarbonyl, $C_1$-$C_6$ alkylaminocarbonyl, di($C_1$-$C_6$ alkyl)-aminocarbonyl, N—($C_1$-$C_3$ alkyl)-N—($C_1$-$C_3$ alkoxy)aminocarbonyl, $C_1$-$C_6$ alkylcarbonyloxy, arylcarbonyloxy, di($C_1$-$C_6$)alkylaminocarbonyloxy, aryl (itself optionally substituted with $C_1$-$C_6$ alkyl or halogen), heteroaryl (itself optionally substituted with $C_1$-$C_6$ alkyl or halogen), heterocyclyl (itself optionally substituted with $C_1$-$C_6$ alkyl or halogen), aryloxy (where the aryl group is optionally substituted with $C_1$-$C_6$ alkyl or halogen), heteroaryloxy (where the heteroaryl group is optionally substituted with $C_1$-$C_6$ alkyl or halogen), heterocyclyloxy (where the heterocyclyl group is optionally substituted with $C_1$-$C_6$ alkyl or halogen), amino, $C_1$-$C_6$ alkylamino, di($C_1$-$C_6$) alkylamino, $C_1$-$C_6$ alkylcarbonylamino, N—($C_1$-$C_6$)alkylcarbonyl-N—($C_1$-$C_6$)alkylamino, arylcarbonyl, (where the aryl group is itself optionally substituted with halogen or $C_1$-$C_6$ alkyl) or two adjacent positions on an aryl or heteroaryl system may be cyclised to form a 5, 6 or 7-membered carbocyclic or heterocyclic ring, itself optionally substituted with halogen or $C_1$-$C_6$ alkyl. Further substituents for aryl or heteroaryl include arylcarbonylamino (where the aryl group is substituted by $C_1$-$C_6$ alkyl or halogen), ($C_1$-$C_6$)alkoxycarbonylamino($C_1$-$C_6$)alkoxycarbonyl-N—($C_1$-$C_6$)alkylamino, aryloxycarbonylamino (where the aryl group is substituted by $C_1$-$C_6$ alkyl or halogen), aryloxycarbonyl-N—($C_1$-$C_6$)alkylamino, (where the aryl group is substituted by $C_1$-$C_6$ alkyl or halogen), arylsulphonylamino (where the aryl group is substituted by $C_1$-$C_6$ alkyl or halogen), arylsulphonyl-N—($C_1$-$C_6$)alkylamino (where the aryl group is substituted by $C_1$-$C_6$ alkyl or halogen), aryl-N—($C_1$-$C_6$)alkylamino (where the aryl group is substituted by $C_1$-$C_6$ alkyl or halogen), arylamino (where the aryl group is substituted by $C_1$-$C_6$ alkyl or halogen), heteroaryl amino (where the heteroaryl group is substituted by $C_1$-$C_6$ alkyl or halogen), heterocyclylamino (where the heterocyclyl group is substituted by $C_1$-$C_6$ alkyl or halogen), aminocarbonylamino, $C_1$-$C_6$ alkylaminocarbonylamino, di($C_1$-$C_6$)alkylaminocarbonylamino, arylaminocarbonylamino where the aryl group is substituted by $C_1$-$C_6$ alkyl or halogen), aryl-N—($C_1$-$C_6$)alkylamino-carbonylamino where the aryl group is substituted by $C_1$-$C_6$ alkyl or halogen), $C_1$-$C_6$alkylaminocarbonyl-N—($C_1$-$C_6$)alkylamino, di($C_1$-$C_6$)alkylaminocarbonyl-N—($C_1$-$C_6$)alkylamino, arylaminocarbonyl-N—($C_1$-$C_6$)alkylamino where the aryl group is substituted by $C_1$-$C_6$ alkyl or halogen) and aryl-N—($C_1$-$C_6$)alkylaminocarbonyl-N—($C_1$-$C_6$)alkylamino where the aryl group is substituted by $C_1$-$C_6$ alkyl or halogen).

For substituted phenyl moieties, heterocyclyl and heteroaryl groups it is preferred that one or more substituents are independently selected from halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, nitro and cyano. It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_1$-$C_6$)alkyl groups. When heterocyclic rings are formed by joining two groups on an N atom, the resulting rings are suitably pyrrolidine, piperidine, thiomorpholine and morpholine each of which may be substituted by one or two independently selected ($C_1$-$C_6$) alkyl groups.

The term "ring" includes corresponding aryls, heteroaryls, cycloalkyls, cycloalkenyls and heterocycles, optionally substituted as described above.

Preferably, in the compounds of the formula (I), $R^2$ and $R^7$ are independently of each other hydrogen, halogen, formyl, cyano or nitro or $R^2$ and $R^7$ are independently of each other $C_1$-$C_6$alkyl, $C_2$-$C_6$alkenyl, $C_2$-$C_6$alkynyl, $C_1$-$C_6$alkoxy, $C_3$-$C_7$ cycloalkyl, $C_3$-$C_7$ cycloalkenyl, phenyl, heteroaryl or a 3-7 membered heterocyclyl, where all these substituents are optionally substituted, or $R^2$ and $R^7$ are independently of each other a group $COR^9$, $CO_2R^{10}$ or $CONR^{11}R^{12}$, $CR^{13}$=$NOR^{14}$, $CR^{15}$=$NNR^{16}R^{17}$, $NHR^{18}$, $NR^{18}R^{19}$ or $OR^{20}$, wherein $R^9$ is $C_1$-$C_6$alkyl, $C_2$-$C_6$alkenyl, $C_2$-$C_6$alkynyl, $C_3$-$C_7$ cycloalkyl, $C_5$-$C_7$cycloalkenyl, phenyl, heteroaryl or a 3-7 membered heterocyclyl, where all these substituents are optionally substituted, $R^{10}$ is hydrogen, $C_1$-$C_6$alkyl, $C_3$-$C_6$alkenyl, $C_3$-$C_6$alkynyl, $C_3$-$C_7$ cycloalkyl, $C_5$-$C_7$cycloalkenyl, phenyl, heteroaryl or is 3-7 membered heterocyclyl, where all these substituents are optionally substituted, $R^{11}$ is hydrogen, $C_1$-$C_6$alkyl, $C_3$-$C_6$alkenyl, $C_3$-$C_6$alkynyl, $C_3$-$C_7$ cycloalkyl, $C_5$-$C_7$cycloalkenyl, phenyl, heteroaryl or a 3-7 membered heterocyclyl, where all these substituents are optionally substituted, $R^{12}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$cycloalkenyl, $C_1$-$C_6$alkylsulfonyl, phenylsulfonyl, heteroarylsulfonyl, amino, $C_1$-$C_6$alkylamino, di$C_1$-

$C_6$alkylamino, phenyl, heteroaryl or a 3-7 membered heterocyclyl, where all these substituents are optionally substituted, or $R^{11}$ and $R^{12}$ may be joined to form an optionally substituted 3-7 membered ring, optionally containing an oxygen, sulfur or nitrogen atom, $R^{13}$ and $R^{15}$ are independently of each other hydrogen, $C_1$-$C_3$alkyl or $C_3$-$C_6$cycloalkyl, $R^{14}$, $R^{16}$ and $R^{17}$ are independently of each other hydrogen, $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, aminocarbonyl, $C_1$-$C_6$alkylaminocarbonyl, di$C_1$-$C_6$alkylaminocarbonyl, phenyl or heteroaryl, where all these substituents are optionally substituted, $R^{18}$ is $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, phenylcarbonyl, phenoxycarbonyl, phenylaminocarbonyl, phenylthiocarbonyl, phenylsulfonyl, heteroarylcarbonyl, heteroaryloxycarbonyl, heteroarylaminocarbonyl, heteroarylthiocarbonyl or heteroarylsulfonyl, where all these substituents are optionally substituted, $R^{19}$ is $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, phenyl or heteroaryl, where all these substituents are optionally substituted, or $R^{18}$ and $R^{19}$ may be joined to form an optionally substituted 3-7 membered ring, optionally containing an oxygen, sulfur or nitrogen atom, where all these substituents are optionally substituted, and $R^{20}$ is $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, aminocarbonyl, $C_1$-$C_6$alkylaminocarbonyl, di$C_1$-$C_6$alkylaminocarbonyl, $C_1$-$C_6$alkylsulfonyl, tri($C_1$-$C_6$alkyl)silyl, phenyl or heteroaryl, where all these substituents are optionally substituted.

More preferably, $R^2$ and $R^7$ are independently of each other hydrogen, halogen, cyano, optionally substituted $C_1$-$C_6$alkyl or a group $COR^9$, $CO_2R^{10}$ or $CONR^{11}R^{12}$, $CR^{13}$=$NOR^{14}$ or $CR^{15}$=$NNR^{18}R^{17}$, wherein $R^9$, $R^{10}$, $R^{11}$ and $R^{12}$ are $C_1$-$C_6$alkyl, $R^{13}$ and $R^{15}$ are hydrogen or $C_1$-$C_3$ alkyl, $R^{14}$ is $C_1$-$C_3$ alkyl, and $R^{16}$ and $R^{17}$ are independently of each other hydrogen or $C_1$-$C_3$alkyl, where $R^2$ and $R^7$ being independently of each other hydrogen, methyl or methyl substituted by $C_1$-$C_3$alkoxy is particularly preferred.

Preference is given to compounds of formula (I) wherein $R^3$, $R^4$, $R^5$ and $R^6$ are independently of each other hydrogen, halogen, hydroxyl, formyl, amino, cyano or nitro, or $R^3$, $R^4$, $R^5$ and $R^6$ are independently of each other $C_1$-$C_6$alkyl, $C_2$-$C_6$alkenyl, $C_2$-$C_6$alkynyl, $C_1$-$C_6$alkoxy, $C_1$-$C_6$alkylthio, $C_1$-$C_6$alkylsulfinyl, $C_1$-$C_6$alkylsulfonyl, $C_3$-$C_7$ cycloalkyl, $C_4$-$C_7$cycloalkenyl, tri($C_1$-$C_6$alkyl)silyl, phenyl, heteroaryl or a 3-7 membered heterocyclyl, where all these substituents are optionally substituted, or $R^3$, $R^4$, $R^5$ and $R^6$ are independently of each other a group $COR^9$, $CO_2R^{10}$ or $CONR^{11}R^{12}$, $CR^{13}$=$NOR^{14}$, $CR^{15}$=$NNR^{16}R^{17}$, $NR^{18}R^{19}$ or $OR^{20}$, wherein $R^9$ is $C_1$-$C_6$alkyl, $C_2$-$C_6$alkenyl, $C_2$-$C_6$alkynyl, $C_3$-$C_7$ cycloalkyl, $C_5$-$C_7$cycloalkenyl, phenyl, heteroaryl or a 3-7 membered heterocyclyl, where all these substituents are optionally substituted, $R^{10}$ is hydrogen, $C_1$-$C_6$alkyl, $C_3$-$C_6$alkenyl, $C_3$-$C_6$alkynyl, $C_3$-$C_7$ cycloalkyl, $C_5$-$C_7$cycloalkenyl, phenyl, heteroaryl or is 3-7 membered heterocyclyl, where all these substituents are optionally substituted, $R^{11}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$cycloalkenyl, phenyl, heteroaryl or a 3-7 membered heterocyclyl, where all these substituents are optionally substituted, $R^{12}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$cycloalkenyl, $C_1$-$C_6$alkylsulfonyl, amino, $C_1$-$C_6$alkylamino, di$C_1$-$C_6$alkylamino, phenyl, heteroaryl or a 3-7 membered heterocyclyl, where all these substituents are optionally substituted, or $R^{11}$ and $R^{12}$ may be joined to form an optionally substituted 3-7 membered ring, optionally containing an oxygen, sulfur or nitrogen atom, $R^{13}$ and $R^{15}$ are independently of each other hydrogen, $C_1$-$C_3$alkyl or $C_3$-$C_6$cycloalkyl, $R^{14}$, $R^{16}$ and $R^{17}$ are independently of each other hydrogen, $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, phenyl or heteroaryl, where all these substituents are optionally substituted, $R^{18}$ and $R^{19}$ are independently of each other $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, phenyl or heteroaryl or $R^{18}$ and $R^{19}$ may be joined to form an optionally substituted 3-7 membered ring, optionally containing an oxygen, sulfur or nitrogen atom, where all these substituents are optionally substituted, and $R^{20}$ is $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, tri($C_1$-$C_6$alkyl)silyl, phenyl or heteroaryl, where all these substituents are optionally substituted.

More preferably, $R^3$, $R^4$, $R^5$ and $R^6$ are independently of each other hydrogen, cyano, $C_1$-$C_6$alkyl, $C_2$-$C_6$alkenyl, $C_1$-$C_6$alkoxy, $C_1$-$C_6$alkoxy$C_1$-$C_6$alkyl, 3-7 membered heterocyclyl or $CR^{13}$=$NOR^{14}$, wherein $R^{13}$ is hydrogen or $C_1$-$C_3$ alkyl and $R^{14}$ is $C_1$-$C_3$ alkyl.

In a group of preferred compounds of the formula (I) $R^3$ and $R^4$ together form a unit =O, or form a unit =$CR^{21}R^{22}$, or form a unit =$NR^{23}$, or form together with the carbon atom to which they are attached a 3-8 membered ring, optionally containing a heteroatom selected from O, S or N and optionally substituted by $C_1$-$C_3$alkyl, $C_1$-$C_3$alkoxy, $C_1$-$C_3$alkylthio, $C_1$-$C_3$alkylsulfinyl, $C_1$-$C_3$alkylsulfonyl, $C_1$-$C_3$haloalkyl, halogen, phenyl, phenyl substituted by $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylcarbonyl, $C_1$-$C_4$alkoxycarbonyl, aminocarbonyl, $C_1$-$C_6$alkylaminocarbonyl, di$C_1$-$C_6$alkylaminocarbonyl, halogen, cyano or by nitro, heteroaryl or heteroaryl substituted by $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylcarbonyl, halogen, cyano or by nitro, wherein $R^{21}$ and $R^{22}$ are independently of each other hydrogen, halogen, cyano or nitro, or $R^{21}$ and $R^{22}$ are independently of each other $C_1$-$C_6$alkyl, $C_1$-$C_6$alkoxy, $C_1$-$C_6$alkylamino, di$C_1$-$C_6$alkylamino, $C_1$-$C_6$alkylcarbonyl, $C_1$-$C_6$alkoxycarbonyl, $C_1$-$C_6$alkylaminocarbonyl, di$C_1$-$C_6$alkylaminocarbonyl, N-phenyl-N—$C_1$-$C_6$alkylaminocarbonyl, N-phenyl$C_1$-$C_6$alkyl-N—$C_1$-$C_6$alkylaminocarbonyl, N-heteroaryl-N—$C_1$-$C_6$alkylaminocarbonyl, N-heteroaryl$C_1$-$C_6$alkyl-N—$C_1$-$C_6$alkylaminocarbonyl, phenyl, heteroaryl, $C_3$-$C_8$cycloalkyl or 3-7 membered heterocyclyl, where all these substituents are optionally substituted, or $R^{21}$ and $R^{22}$ may be joined together to form a 5-8 membered ring optionally containing a heteroatom selected from O, S or N and optionally substituted by $C_1$-$C_2$alkyl or $C_1$-$C_2$alkoxy, $R^{23}$ is nitro or cyano, or $R^{23}$ is $C_1$-$C_6$alkylamino, di$C_1$-$C_6$alkylamino, $C_1$-$C_6$alkoxy, $C_3$-$C_6$alkenyloxy, $C_3$-$C_6$alkynyloxy, phenoxy, phenylamino, N-phenyl-N—$C_1$-$C_6$alkylamino, N-phenyl$C_1$-$C_6$alkyl-N—$C_1$-$C_6$alkylamino heteroaryloxy, heteroarylamino, N-heteroaryl-N—$C_1$-$C_6$alkylamino or N-heteroaryl$C_1$-$C_6$alkyl-N—$C_1$-$C_6$alkylamino, where all these substituents are optionally substituted, where It is particularly preferred, when $R^3$ and $R^4$ together form a unit =O or =NR$^{23}$, wherein $R^{23}$ is $C_1$-$C_3$alkoxy.

Preference is given to compounds of the formula (I), wherein $R^3$ and $R^6$ together with the carbon atoms to which they are attached form a saturated 3-4 membered ring, optionally containing a heteroatom or group selected from O, S or NR$^{24}$, and optionally substituted by $C_1$-$C_4$alkyl, $C_1$-$C_4$alkoxy, $C_1$-$C_4$alkylthio, halogen, $C_1$-$C_4$alkylcarbonyl or $C_1$-$C_4$alkoxycarbonyl, or $R^3$ and $R^6$ together with the carbon atoms to which they are attached form a 5-8 membered ring, optionally containing a heteroatom selected from O, S or N, and optionally substituted by $C_1$-$C_3$alkyl, $C_1$-$C_3$alkoxy, $C_1$-$C_3$alkylthio, $C_1$-$C_3$alkylsulfinyl, $C_1$-$C_3$alkylsulfonyl, $C_1$-$C_3$haloalkyl, halogen, phenyl, phenyl substituted by $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylcarbonyl, $C_1$-$C_4$alkoxycarbonyl, aminocarbonyl, $C_1$-$C_6$alkylaminocarbonyl, di$C_1$-$C_6$alkylaminocarbonyl, halogen, cyano or by nitro, heteroaryl or heteroaryl substituted by $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylcarbonyl, halogen, cyano or by nitro, or $R^3$ and $R^6$ together form a bond, wherein $R^{24}$ is hydrogen, $C_1$-$C_6$alkyl, $C_3$-$C_6$alkenyl, $C_3$-$C_6$alkynyl, $C_1$-$C_6$alkoxy, $C_1$-$C_6$alkylcarbonyl, $C_1$-$C_6$alkoxycarbonyl, $C_1$-$C_6$alkylaminocarbonyl, di$C_1$-$C_6$alkylaminocarbonyl, phenoxycarbonyl $C_1$-$C_6$alkylsulfonyl, phenylsulfonyl or heteroaryloxycarbonyl, where all these substituents are optionally substituted.

More preferably, $R^3$ and $R^6$ together form a bond.

In preferred compounds of the formula (I) $R^1$ and $R^8$ are independently of each other hydrogen or $C_1$-$C_3$alkyl, where, more preferably, $R^1$ and $R^8$ are hydrogen.

In another preferred group of compounds of formula (I), $R^1$ and $R^8$ together with the carbon atoms to which they are attached form a 3-7 membered ring, optionally containing an oxygen or sulphur atom.

The group G denotes hydrogen, an alkali metal cation such as sodium or potassium, alkaline earth metal cation such as calcium, sulfonium cation (preferably —S($C_1$-$C_6$alkyl$_3$)$^+$) or ammonium cation (preferably —NH$_4^+$ or —N($C_1$-$C_6$alkyl)$_4^+$), or $C_1$-$C_6$alkyl, $C_3$-$C_6$alkenyl or $C_3$-$C_6$alkynyl or a latentiating group. The latentiating group G is preferably selected from the groups were G is $C_1$-$C_8$ alkyl, $C_2$-$C_8$ haloalkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, C(X$^a$)—R$^a$, C(X$^b$)—X$^c$—R$^b$, C(X$^d$)—N(R$^c$)—R$^d$, —SO$_2$—R$^e$, —P(X$^e$)(R$^f$)—R$^g$ or CH$_2$—X$^f$—R$^h$ wherein X$^a$, X$^b$, X$^c$, X$^d$, X$^e$ and X$^f$ are independently of each other oxygen or sulfur;

R$^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_6$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_1$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, R$^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_6$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_8$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —$C(X^a)$—$R^a$ or —$C(X^b)$—$X^c$—$R^b$, and the meanings of $X^a$, $R^a$, $X^b$, $X^b$ and $R^b$ are as defined above.

It is preferred that G is hydrogen, an alkali metal or alkaline earth metal, where hydrogen is especially preferred.

Het is preferably an optionally substituted monocyclic 6-membered or, preferably, 5-membered sulfur or, preferably, nitrogen containing heteroaromatic ring. More preferably, Het is a monocyclic 5-membered sulfur and nitrogen containing heteroaromatic ring, and even more preferably, Het is a group of the formula $R_1$ to $R_{12}$

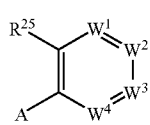
(R₁)

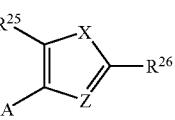
(R₂)

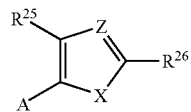
(R₃)

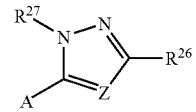
(R₄)

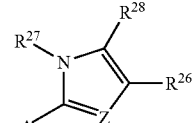
(R₅)

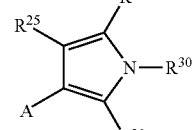
(R₆)

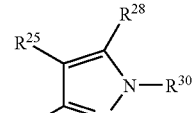
(R₇)

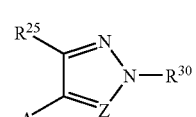
(R₈)

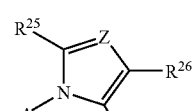
(R₉)

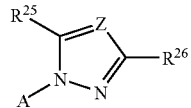
(R₁₀)

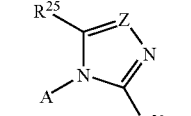
(R₁₁)

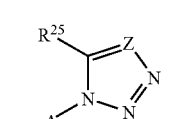
(R₁₂)

wherein
A designates the point of attachment to the ketoenol moiety,
$W^1$ is N or $CR^{28}$,
$W^2$ and $W^3$ are independently of each other N or $CR^{26}$,
$W^4$ is N or $CR^{29}$,
with the proviso that at least one of $W^1$, $W^2$, $W^3$ or $W^4$ is N,
X is O, S, Se, or $NR^{31}$,
Z is N or $CR^{32}$,
wherein
$R^{25}$ is hydrogen, halogen, $C_1$-$C_4$alkyl, $C_1$-$C_4$haloalkyl, $C_3$-$C_6$-cycloalkyl, $C_3$-$C_6$-halocycloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, nitro or cyano, preferably halogen, $C_1$-$C_2$alkyl, $C_1$-$C_2$haloalkyl, vinyl, ethynyl, or methoxy, and even more preferably methyl or ethyl, $R^{26}$ is hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_3$-$C_6$ cycloalkyl, $C_5$-$C_6$cycloalkenyl, halogen, $C_1$-$C_6$alkoxy, $C_1$-$C_6$alkoxy-$C_1$-$C_6$alkyl, $C_1$-$C_6$haloalkoxy, optionally substituted aryl, optionally substituted aryloxy, optionally substituted heteroaryl or optionally substituted heteroaryloxy, preferably optionally substituted aryl or optionally substituted heteroaryl wherein the substituents are selected from halogen, $C_1$-$C_2$-alkyl, $C_1$-$C_2$-alkoxy, $C_1$-$C_2$ haloalkyl, $C_1$-$C_2$ haloalkoxy, cyano or nitro, and even more preferably phenyl, substituted once, twice or three times, by halogen, $C_1$-$C_2$-alkyl, $C_1$-$C_2$-alkoxy, $C_1$-$C_2$ haloalkyl, $C_1$-$C_2$ haloalkoxy or cyano, $R^{27}$ is hydrogen, $C_1$-$C_4$ alkyl, $C_1$-$C_4$ haloalkyl, $C_3$-$C_6$-cycloalkyl, $C_3$-$C_6$-halocycloalkyl, $C_2$-$C_3$alkenyl, $C_2$-$C_3$alkynyl, $C_1$-$C_4$ haloalkyl or $C_2$-$C_3$ haloalkenyl, preferably methyl or ethyl, $R^{28}$ is hydrogen, methyl, halomethyl or halogen, preferably hydrogen, $R^{29}$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl or cyano, preferably hydrogen, halogen, methyl or ethyl, $R^{30}$ is hydrogen, methyl, ethyl, halomethyl, haloethyl, optionally substituted aryl or optionally substituted heteroaryl, preferably optionally substituted aryl or optionally substituted heteroaryl wherein the substituents are selected from halogen, $C_1$-$C_2$-alkyl, $C_1$-$C_2$-alkoxy, $C_1$-$C_2$ haloalkyl, $C_1$-$C_2$ haloalkoxy, cyano or nitro, even more preferably phenyl, substituted once, twice or three times, by halogen, $C_1$-$C_2$-alkyl, $C_1$-$C_2$-alkoxy, $C_1$-$C_2$ haloalkyl, $C_1$-$C_2$ haloalkoxy or cyano, $R^{31}$ is hydrogen, methyl, ethyl or halomethyl, and $R^{32}$ is hydrogen, methyl, ethyl, halomethyl, haloethyl, halogen, cyano or nitro.

More preferably, Het is a group of the formula ($R_2$), wherein X is S and Z is N and $R^{25}$ and $R^{26}$ are as defined above.

It is also preferred that Het is a group of the formula ($R_2$), wherein X is S and Z is $CR^{32}$ and $R^{25}$, $R^{26}$ and $R^{32}$ are as defined above.

Those compounds of the formula (I) are particularly preferred, wherein $R^1$ to $R^8$ and G are hydrogen, Het is a group $R_2$

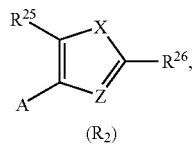

($R_2$)

wherein X is S, Z is N, $R^{25}$ is methyl or ethyl and $R^{26}$ is 4-chlorophenyl or 4-bromophenyl.

The invention relates also to the agronomically acceptable salts which the compounds of formula (I) preferably are able to form with amines, alkali metal and alkaline earth metal bases or quaternary ammonium bases.

Among the alkali metal and alkaline earth metal hydroxides as salt formers, special mention should be made of the hydroxides of lithium, sodium, potassium, magnesium and calcium, but especially the hydroxides of sodium and potassium. The compounds of formula (I) according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$-alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R'_aR'_bR'_cR'_d)]OH$ wherein $R'_a$, $R'_b$, $R'_c$ and $R'_d$ are each independently of the others $C_1$-$C_4$alkyl. Further suitable tetraalkylammonium bases with other anions can be obtained, for example, by anion exchange reactions.

Depending on the nature of the substituents, compounds of formula (I) may exist in different isomeric forms. When G is hydrogen, for example, compounds of formula (I) may exist in different tautomeric forms. This invention covers all such isomers and tautomers and mixtures thereof in all proportions. Also, when substituents contain double bonds, cis- and trans-isomers can exist. These isomers, too, are within the scope of the claimed compounds of the formula (I).

Compounds of formula (I) wherein G is $C_1$-$C_8$ alkyl, $C_2$-$C_8$ haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating compounds of formula (A), which are compounds of formula (I) wherein G is H, with a reagent G-Z, wherein G-Z is alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—CH$_2$—X$^f$—R$^h$, wherein X$^f$ is sulfur), a C$_1$-C$_8$ alkyl sulfonate, or a di-C$_1$-C$_8$-alkyl sulfate, or with a C$_3$-C$_8$ alkenyl halide, or with a C$_3$-C$_8$ alkynyl halide, or with an acylating agent such as a carboxylic acid, HO—C(X$^a$)R$^a$, wherein X$^a$ is oxygen, an acid chloride, Cl—C(X$^a$)R$^a$, wherein X$^a$ is oxygen, or acid anhydride, [R$^a$C(X$^a$)]$_2$O, wherein X$^a$ is oxygen, or an isocyanate, R$^c$N═C═O, or a carbamoyl chloride, Cl—C(X$^d$)—N(R$^c$)—R$^d$ (wherein X$^d$ is oxygen and with the proviso that neither R$^c$ or R$^d$ is hydrogen), or a thiocarbamoyl chloride Cl—C(X$^d$)—N(R$^c$)—R$^d$ (wherein X$^d$ is sulfur and with the proviso that neither R$^c$ or R$^d$ is hydrogen) or a chloroformate, Cl—C(X$^b$)—X$^c$—R$^b$, (wherein X$^b$ and X$^c$ are oxygen), or a chlorothioformate Cl—C(X$^b$)—X$^c$—R$^b$ (wherein X$^b$ is oxygen and X$^c$ is sulfur), or a chlorodithioformate Cl—C(X$^b$)—X$^c$—R$^b$, (wherein X$^b$ and X$^c$ are sulfur), or an isothiocyanate, R$^c$N═C═S, or by sequential treatment with carbon disulfide and an alkylating agent, or with a phosphorylating agent such as a phosphoryl chloride, Cl—P(X$^e$)(R$^f$)—R$^g$ or with a sulfonylating agent such as a sulfonyl chloride Cl—SO$_2$—R$^e$, preferably in the presence of at least one equivalent of base.

Depending on the nature of the substituents R$^1$ to R$^8$, and of the group G, isomeric compounds of formula (I) may be formed. For example, compounds of formula (A) wherein R$^1$ and R$^8$ are different may give rise to compounds of formula (I) or to compounds of formula (IA), or to a mixture of compounds of formula (I) and formula (IA). This invention covers both compounds of formula (I) and compounds of formula (IA), together with mixtures of these compounds in any ratio.

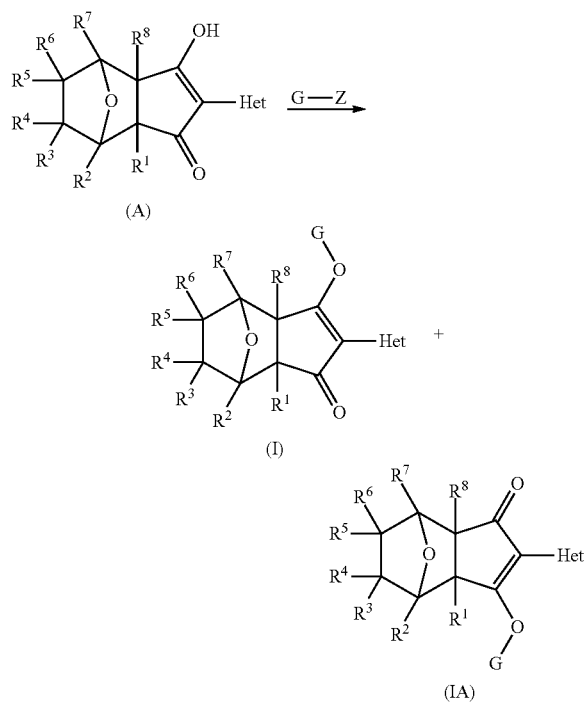

The O-alkylation of cyclic 1,3-diones is known; suitable methods are described, for example, in U.S. Pat. No. 4,436, 666. Alternative procedures have been reported by M. T. Pizzorno and S. M. Albonico, Chem. Ind. (London) (1972), 425; H. Born et al., J. Chem. Soc. (1953), 1779; M. G. Constantino et al., Synth. Commun., (1992), 22 (19), 2859; Y. Tian et al., Synth. Commun. (1997), 27 (9), 1577; S. Chandra Roy et al., Chem. Lett. (2006), 35 (1), 16; P. K. Zubaidha et al., Tetrahedron Lett. (2004), 45, 7187 and by B. Zwanenburg et al., Tetrahedron (2005), 45 (22), 7109.

The acylation of cyclic 1,3-diones may be effected by procedures similar to those described, for example, in U.S. Pat. No. 4,551,547, U.S. Pat. No. 4,175,135, U.S. Pat. No. 4,422,870, U.S. Pat. No. 4,659,372 and U.S. Pat. No. 4,436, 666. Typically diones of formula (A) may be treated with the acylating agent in the presence of at least one equivalent of a suitable base, optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a coupling agent such as 2-chloro-1-methylpyridinium iodide, N,N-dicyclohexycarbodiimide, 1-(3-dimethylaminopropyl)-3-ethylcarbodiimide and N,N'-carbodiimidazole, and optionally a base such as triethylamine or pyridine in a suitable solvent such as tetrahydrofuran, dichloromethane or acetonitrile. Suitable procedures are described, for example, by W. Zhang and G. Pugh, Tetrahedron Lett. (1999), 40 (43), 7595 and T. Isobe and T. Ishikawa, J. Org. Chem. (1999), 64 (19) 6984.

Phosphorylation of cyclic-1,3-diones may be effected using a phosphoryl halide or thiophosphoryl halide and a base by procedures analogous to those described in U.S. Pat. No. 4,409,153.

Sulfonylation of compounds of formula (A) may be achieved using an alkyl or aryl sulfonyl halide, preferably in the presence of at least one equivalent of base, for example by the procedure of C. J. Kowalski and K. W. Fields, J. Org. Chem. (1981), 46, 197.

Certain compounds of formula (I) are alkenes, and as such undergo further reactions typical of alkenes to give additional compounds of formula (I) according to known procedures. Examples of such reactions include, but are not restricted to, halogenation, epoxidation, cyclopropanation, dihydroxylation and hydration of alkenes. In turn, these products may be transformed into additional compounds of formula (I) by methods described, for example, by Michael B. Smith and Jerry March, March's Advanced Organic Chemistry (Sixth Edition), John Wiley and Sons. Compounds of formula (I) wherein R$^3$ and R$^6$ form a bond and R$^4$ or R$^5$ are C$_1$-C$_6$alkoxy are enol ethers, and these may be hydrolysed to the corresponding ketone using standard procedures to give additional compounds of formula (I). Compounds of formula (I) wherein R$^3$ and R$^6$ form a bond and R$^4$ or R$^5$ are halogen, preferably chloride or bromide, may undergo a cross-coupling reaction with a suitable coupling partner under conditions described in the literature for Suzuki-Miyaura, Sonogashira, Stille and related cross-coupling reactions to give additional compounds of formula (I) (see, for example, C. J. O'Brien, M. G. Organ Angew. Chem. Int. Ed. 2007, 46, 2768-2813; A. Suzuki, Journal of Organometallic Chemistry (2002), 653, 83; N. Miyaura and A. Suzuki Chem. Rev. (1995), 95, 2457-2483).

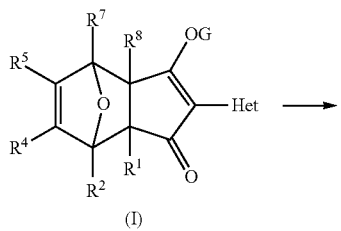

(I)

where $R^3$ and $R^6$ form a bond

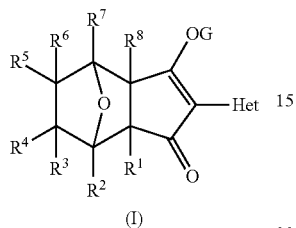

(I)

Compounds of formula (A) may be prepared via the cyclisation of compounds of formula (B), preferably in the presence of an acid or base, and optionally in the presence of a suitable solvent, by analogous methods to those described in U.S. Pat. No. 4,209,532. The compounds of the formula (B) have been particularly designed as intermediates in the synthesis of the compounds of the formula (I). Compounds of formula (B) wherein R is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

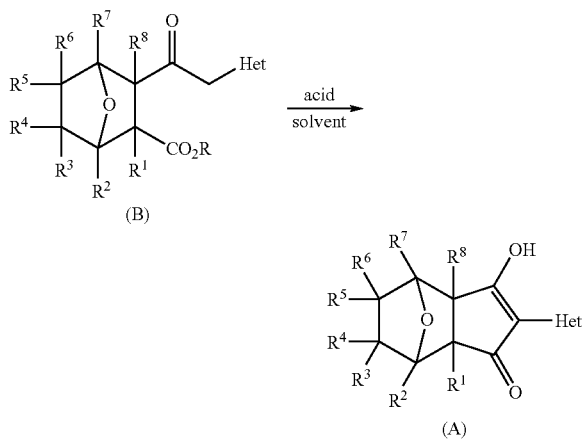

Compounds of formula (B) wherein R is alkyl (preferably methyl or ethyl), may be cyclised under acidic or basic conditions, preferably in the presence of at least one equivalent of a strong base such as potassium tert-butoxide, lithium diisopropylamide or sodium hydride and in a solvent such as tetrahydrofuran, dimethylsulfoxide or N,N-dimethylformamide.

Compounds of formula (B), wherein R is H, may be prepared by saponification of compounds of formula (C) wherein R' is alkyl (preferably methyl or ethyl), under standard conditions, followed by acidification of the reaction mixture to effect decarboxylation, by similar processes to those described, for example, in U.S. Pat. No. 4,209,532.

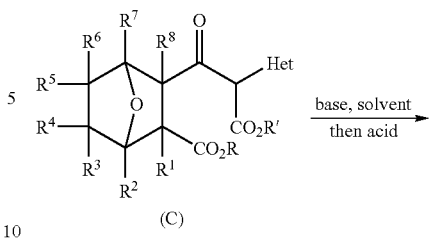

(C)

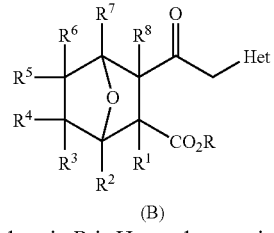

(B)

Compounds of formula (B), wherein R is H may be esterified to compounds of formula (B), wherein R is alkyl, under standard conditions.

Compounds of formula (C) wherein R is alkyl may be prepared by treating compounds of formula (D) with suitable carboxylic acid chlorides of formula (E) wherein R is alkyl under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between −80° C. and 30° C.:

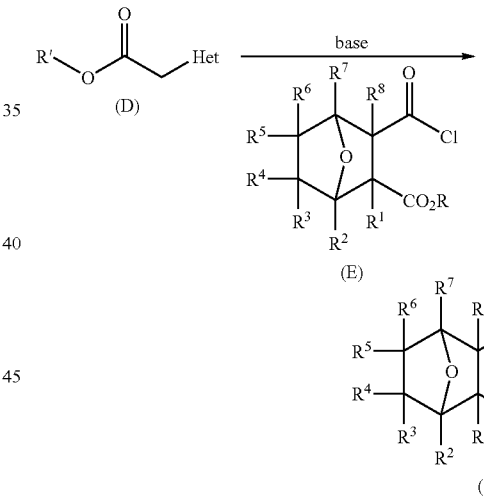

Alternatively, compounds of formula (C), wherein R is H, may be prepared by treating compounds of formula (D) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 0° C.) and reacting the resulting anion with a suitable anhydride of formula (F):

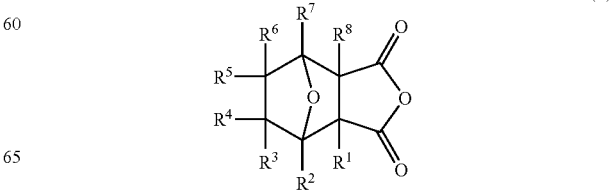

(F)

Compounds of formula (D) are known, or may be made by known methods from known compounds (see, for example, E. Bellur and P. Langer, Synthesis (2006), 3, 480-488; E. Bellur and P. Langer, Eur. J. Org. Chem. (2005), 10, 2074-2090; G. Bartolo et al., J. Org. Chem. (1999), 64 (21), 7693-7699; R. Kranich et al., J. Med. Chem. (2007), 50 (6), 1101-1115; I. Freifeld et al., J. Org. Chem. (2006), 71 (13), 4965-4968; S. Hermann et al., WO2006/087120; R. Fischer et al. WO96/16061; H. A. Staab and G. A. Schwalbach, Justus Liebigs Annalen der Chemie (1968), 715, 128-34; J-L Brayer et al., EP402246; P. Chemla et al., WO99/32464; A. Dornow and G. Petsch, Chem. Ber. (1953), 86, 1404-1407; E. Y-H Chao et al., WO2001/000603; D. B. Lowe et al., WO2003/011842; R. Fischer et al., WO2001/096333; J. Ackermann et al., WO2005/049572; B. Li et al., Bioorg. Med. Chem. Lett. (2002), 12, 2141-2144, G. P. Rizzi, J. Org. Chem. (1968), 33 (4) 13333-13337; M. Okitsu and K. Yoshid, JP63230670; F. Bohlmann et al., Chem. Ber. (1955), 88, 1831-1838; R. Fischer et al., WO2003/035463; R. Fischer er al., WO2005/005428; D O'Mant, GB1226981).

Compounds of formula (E) may be prepared from compounds of formula (F) by treatment with an alkyl alcohol, R—OH, in the presence of a base, such as an alkaline metal alkoxide (see, for example, S. Buser and A. Vasella, Helv. Chim. Acta (2005), 88, 3151; M. E. Hart et al., Bioorg. Med. Chem. Lett. (2004), 14, 1969), followed by treatment of the resulting acid with a chlorinating reagent such as oxalyl chloride or thionyl chloride under known conditions (see, for example, C. Santelli-Rouvier. Tetrahedron Lett. (1984), 25 (39), 4371; D. M. Walba and M. D. Wand, Tetrahedron Lett. (1982), 23 (48), 4995; J. Cason, Org. Synth. Coll. Vol. III, (1955), 169).

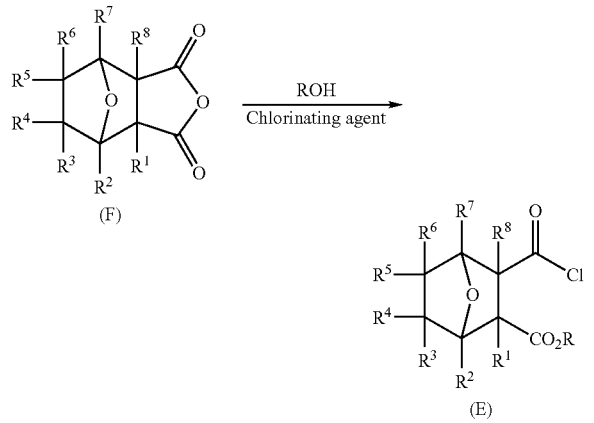

Compounds of formula (F) wherein $R^3$ and $R^6$ are hydrogen may be prepared by the reduction of compounds of formula (G) under known conditions (see, for example, Y. Baba, N. Hirukawa and M. Sodeoka, Bioorg. Med. Chem. (2005), 13 (17), 5164; M. E. Hart et al., Bioorg. Med. Chem. Lett. (2004), 14 (18), 1969; Y. Baba, N. Hirukawa, N. Tanohira and M. Sodeoka, J. Am. Chem. Soc. (2003), 125, 9740).

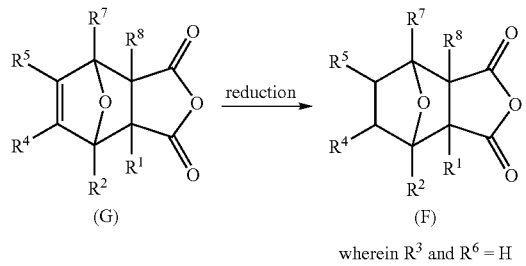

wherein $R^3$ and $R^6$ = H

Compounds of formula (G) may be prepared by reacting compounds of formula (H) with maleic anhydrides of formula (J), optionally in the presence of a Lewis acid catalyst, and according to procedures described, for example, by O. Diels and K. Alder, Liebigs Ann. Chem. (1931), 490, 257; K. T. Potts and E. B. Walsh, J. Org. Chem. (1984), 49 (21), 4099; J. Jurczak, T. Kozluk, S. Filipek and S. Eugster, Helv. Chim. Acta (1982), 65, 1021; W. G. Dauben, C. R. Kessel and K. H. Takemura, J. Am. Chem. Soc. (1980), 102, 6893; A. Pelter and B. Singaram, Tetrahedron Lett. (1982), 23, 245; M. W. Lee and C. W. Herndon, J. Org. Chem. (1978), 43, 518; B. E. Fisher and J. E. Hodge, J. Org. Chem. (1964), 29, 776; G. F. D'Alelio, C. J. Williams and C. L. Wilson, J. Org. Chem. (1960), 25, 1028; Z. Z Song, M. S. Ho and H. N. C. Wong, J. Org. Chem. (1994), 59 (14) 3917-3926; W. Tochtermann, S. Bruhn and C. Wolff, Tetrahedron Lett. (1994), 35(8) 1165-1168; W. G. Dauben, J. Y. L. Lam and Z. R. Guo, J. Org. Chem. (1996), 61(14) 4816-4819; M. Sodeoka, Y. Baba, S. Kobayashi and N. Hirukawa, Bioorg. Med. Chem. Lett. (1997), 7(14), 1833; M. Avalos, R. Babiano, J. L. Bravo, P. Cintas, J. L. Jimenez and J. C. Palacios, Tetrahedron Lett. (1998), 39(50), 9301; J. Auge, R. Gil, S. Kalsey and N. Lubin-Germain, Synlett (2000), 6, 877; I. Hemeon, C. Deamicis, H. Jenkins, P. Scammells and R. D. Singer, Synlett (2002), 11, 1815; M. Essers, B. Wibbeling and G. Haufe, Tetrahedron Lett. (2001), 42 (32), 5429; P. Vogel et al., Tetrahedron: Asymmetry (1996), 7 (11), 3153; Y. Baba, N. Hirukawa, N. Tanohira and M. Sodeoka, J. Am. Chem. Soc. (2003), 125, 9740; L. Ghosez et al., Tetrahedron Lett. (1988), 29 (36), 4573 (and references therein); H. Kotsuki, S. Kitagawa and H. Nishizawa, J. Org. Chem. (1978), 43 (7) 1471; Y. Li et al., J. Org. Chem. (1997), 62 (23), 7926; M. Drew et al., J. Chem. Soc. Perkin Trans. 1 (1985), 1277; R. N. McDonald and C. E. Reineke, J. Org. Chem. (1967), 32, 1878; R. H. Fleming and B. M. Murray, J. Org. Chem. (1979), 44 (13), 2280; M. J. Goldstein and G. L. Thayer Jr. J. Am. Chem. Soc. (1965), 87(9), 1925 and G. Keglevich et al., J. Organomet. Chem. (1999), 579, 182 and references therein.

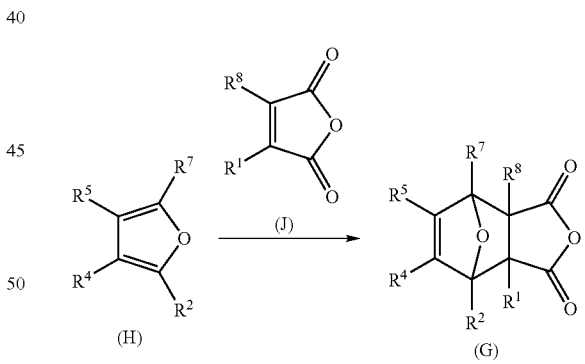

Compounds of formula (H) and formula (J) are known compounds, or may be made from known compounds by known methods.

Certain compounds of formula (G) are alkenes, and as such undergo further reactions typical of alkenes to give additional compounds of formula (F) according to known procedures. Examples of such reactions include, but are not restricted to, halogenation, epoxidation, cyclopropanation, dihydroxylation and hydration of alkenes. In turn, these products may be transformed into additional compounds of formula (F) by methods described, for example, by Michael B. Smith and Jerry March, March's Advanced Organic Chemistry (Sixth Edition), John Wiley and Sons.

Compounds of formula (G) may also be prepared by reacting compounds of formula (H) with compounds of formula (K), wherein R" is hydrogen or an alkyl group, to give compounds of formula (L) and cyclising compounds of formula (L) under known conditions (see, for example, P. W. Sprague et al., J. Med. Chem. (1985), 28, 1580; A. P. Guzaev and M Manoharan, J. Am. Chem. Soc. (2003), 125, 2380; and A. P. Marchand and R. W. Allen, J. Org. Chem. (1975), 40 (17), 2551.

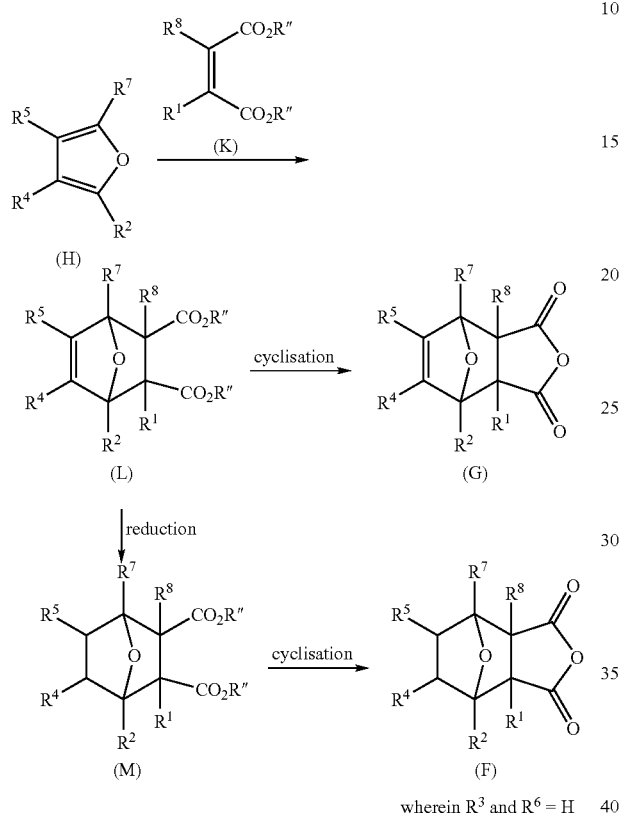

wherein $R^3$ and $R^6 = H$

Compounds of formula (L) may also be reduced to compounds of formula (M), and compounds of formula (M) cyclised to compounds of formula (F) wherein $R^3$ and $R^6$ are hydrogen, under conditions similar to those described previously.

Compounds of formula (K) are known compounds, or may be prepared from known compounds by known methods.

In a further approach to compounds of formula (A), compounds of formula (N), which are compounds of formula (A) wherein Het is ($R_2$) when $R^{25}$ is $CH_2R'''$ and R''' is hydrogen, alkyl or halogenoalkyl (preferably hydrogen, methyl or trifluoromethyl), may be prepared by thermal rearrangement of compounds of formula (O), optionally in the presence of a suitable solvent and optionally under microwave irradiation.

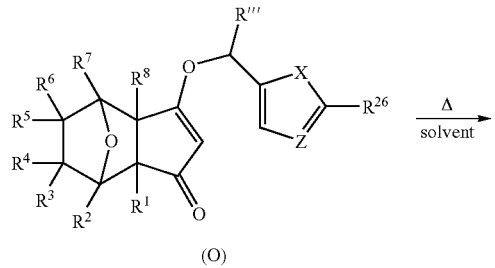

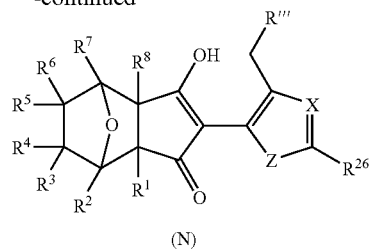

Preferably, the rearrangement is effected by heating compounds of formula (O) at temperatures of between 120-250° C., optionally in a suitable solvent such as 1,2-dimethoxyethane, diethylene glycol methyl ether, triglyme, tetraglyme, xylene, mesitylene or Dowtherm®, and optionally under microwave irradiation.

Similarly, compounds of formula (P), which are compounds of formula (A) wherein Het is ($R_3$) when $R^{25}$ is $CH_2R'''$ and R''' is hydrogen, alkyl or halogenoalkyl (preferably hydrogen, methyl or trifluoromethyl), may be prepared from compounds of formula (Q) using similar methods.

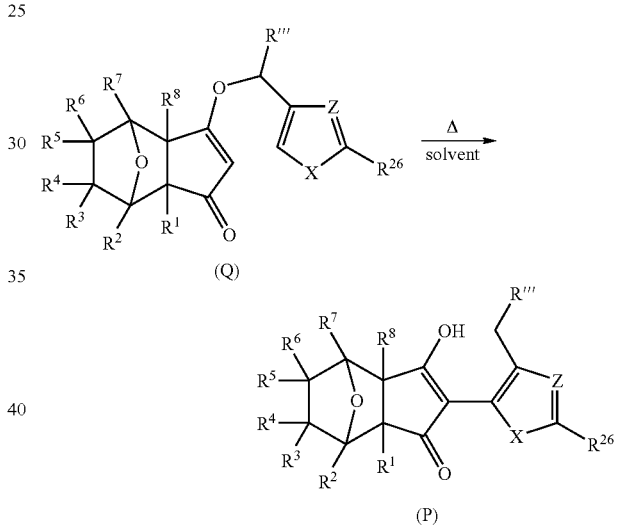

Compounds of formula (O) may be prepared from compounds of formula (R) by alkylation with compounds of formula (S), wherein L is a suitable leaving group such as a halogen or an alkyl- or aryl-sulfonate, optionally in the presence of a suitable base and optionally in a suitable solvent as described above for the alkylation of compounds of formula (A)

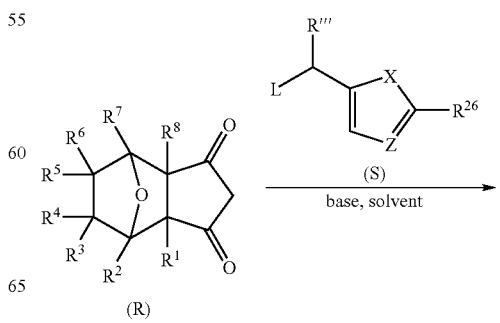

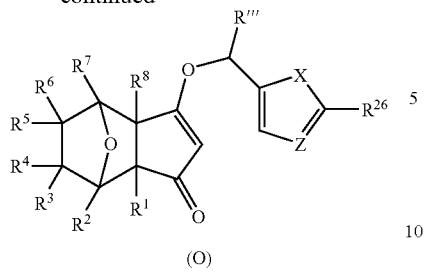

(O)

Similarly, compounds of formula (Q) may be prepared from compounds of formula (R) by alkylation with compounds of formula (T), wherein L is a suitable leaving group such as a halogen or an alkyl- or aryl-sulfonate, under similar conditions.

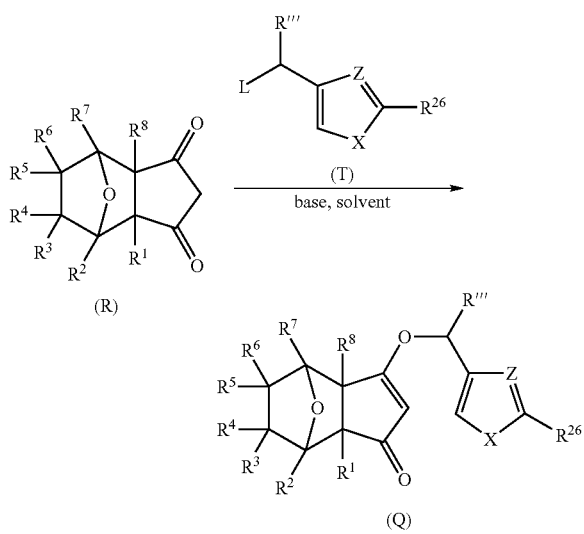

In an alternative approach, compounds of formula (O) may be prepared from compounds of formula (R) by condensation with alcohols of formula (U), optionally in the presence of a suitable acid catalyst such as p-toluenesulfonic acid, or a Lewis acid catalyst, for example, ytterbium (III) trifluoromethanesulfonate, lanthanum (III) trifluoromethanesulfonate, sodium tetrachloroaurate (III) dihydrate, titanium (IV) chloride, indium (III) chloride or aluminium chloride, and optionally in a suitable solvent. Suitable solvents are selected to be compatible with the reagents used, and include, for example, toluene, ethanol or acetonitrile. Similar approaches have been described by, for example, M. Curini, F. Epifano, S. Genovese, Tetrahedron Lett. (2006), 47, 4697-700 and A. Arcadi, G. Bianchi, S. Di Giuseppe, F. Marinelli, Green Chemistry (2003), 5, 64-7.

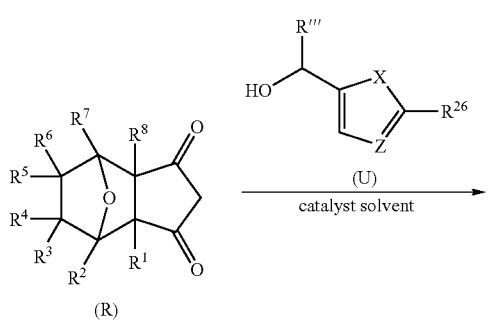

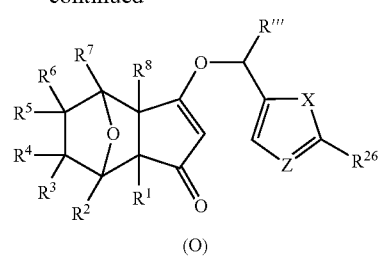

(O)

Alternatively, the condensation may be effected in the presence of suitable coupling agents such as 2-chloro-1-methylpyridinium iodide, N,N'-dicyclohexylcarbodiimide, 1,(3-dimethylaminopropyl)-3-ethylcarbodiimimde and N,N-carbodiimidazole and optionally a suitable base such a triethylamine or pyridine in a suitable solvent such as tetrahydrofuran, acetonitrile or dichloromethane, or in the presence of a triarylphosphine (such as triphenylphosphine) and a dialkyl azidodicarboxylate (preferably diethyl azidodicarboxylate or diisopropyl azidodicarboxylate) and in a suitable solvent such as diethyl ether, tetrahydrofuran or 1,4-dioxane as described, for example, by O. Mitsunobu, Synthesis (1981), 1, 1-28.

Using similar processes, compounds of formula (Q) may be prepared by reaction of compounds of formula (R) with compounds of formula (V).

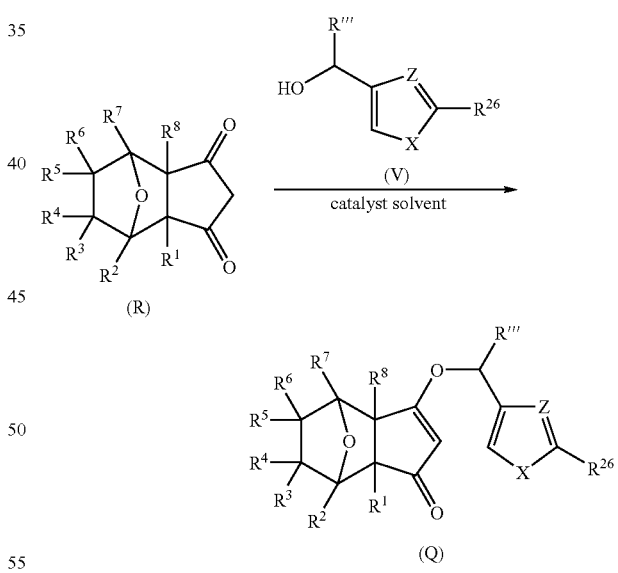

Additional compounds of formula (O) wherein $R^{26}$ is an aromatic or heteroaromatic moiety, or is an alkyl, alkenyl or alkynyl group, may be prepared by the reaction of compounds of formula (W), wherein Q is an atom or group suitable for undergoing cross-coupling reactions (for example Q is chlorine, bromine or iodine, or a haloalkylsulfonate such as trifluoromethanesulfonate), and R''' is as defined for compound of formula (N), with a suitable coupling partner under conditions described in the literature for Suzuki-Miyaura, Sonogashira, Stille and related cross-coupling reactions.

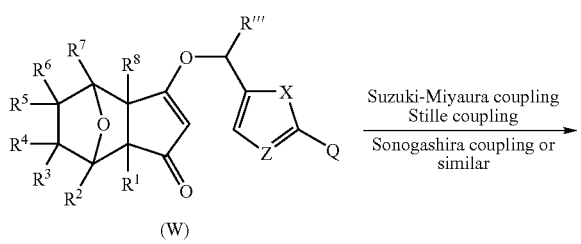

(W)

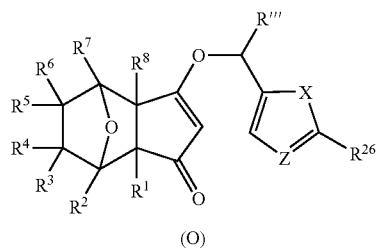

(O)

For example, compounds of formula (W) may be treated with aryl-, heteroaryl-, alkyl-, alkenyl- or alkynylboronic acids, $R^{26}$—$B(OH)_2$, boronate esters, $R^{26}$—$B(OR'''')_2$, wherein $R''''$ is $C_1$-$C_6$alkyl or $R^{26}$—$B(OR'''')_2$ represents cyclic boronate esters derived from a $C_1$-$C_6$diol (especially preferred are cyclic boronate esters derived from pinacol), or a metal (especially potassium) aryl-, heteroaryl, alkyl-, alkenyl- and alkynyltrifluoroborate salts, $M^+[R^{26}$—$BF_3]^-$ in the presence of a suitable palladium catalyst, a suitable ligand and a suitable base in the presence of a suitable solvent, under Suzuki-Miyaura conditions (see, for example K. Billingsley and S. Buchwald, J. Am. Chem. Soc. (2007), 129, 3358-3366; H. Stefani, R. Cella and A. Vieira, Tetrahedron (2007), 63, 3623-3658; N. Kudo, M. Perseghini and G. Fu, Angew. Chem. Int. Ed. (2006), 45, 1282-1284; A. Roglans, A. Pla-Quintana and M. Moreno-Mañas, Chem. Rev. (2006), 106, 4622-4643; J-H Li, Q-M Zhu and Y-X Xie, Tetrahedron (2006), 10888-10895; S. Nolan et al., J. Org. Chem. (2006), 71, 685-692; M. Lysén and K. Köhler, Synthesis (2006), 4, 692-698; K. Anderson and S. Buchwald, Angew. Chem. Int. Ed. (2005), 44, 6173-6177; Y. Wang and D. Sauer, Org. Lett. (2004), 6 (16), 2793-2796; I. Kondolff, H. Doucet and M, Santelli, Tetrahedron, (2004), 60, 3813-3818; F. Bellina, A. Carpita and R. Rossi, Synthesis (2004), 15, 2419-2440; H. Stefani, G. Molander, C-S Yun, M. Ribagorda and B. Biolatto, J. Org. Chem. (2003), 68, 5534-5539; A. Suzuki, Journal of Organometallic Chemistry (2002), 653, 83; G. Molander and C-S Yun, Tetrahedron (2002), 58, 1465-1470; G. Zou, Y. K. Reddy and J. Falck, Tetrahedron Lett. (2001), 42, 4213-7215; S. Darses, G. Michaud and J-P, Genêt, Eur. J. Org. Chem. (1999), 1877-1883).

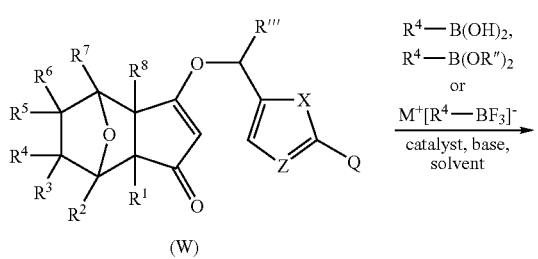

(W)

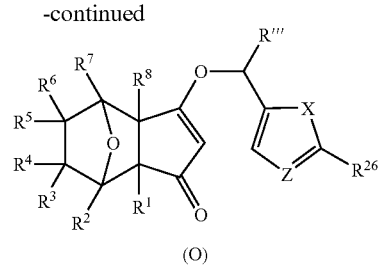

(O)

Alternatively, compounds of formula (O), wherein $R^{26}$ is an optionally substituted acetylene, may be prepared from compounds of formula (W) by reacting with a terminal alkyne, $R^{26}$—H, in the presence of a suitable palladium catalyst and optionally in the presence of a suitable copper co-catalyst, a suitable ligand, a suitable base and a suitable additive under conditions known to effect the Sonogashira coupling (see, for example, U. Sorenson and E Pombo-Villar, Tetrahedron (2005), 2697-2703; N. Leadbeater and B. Tominack, Tetrahedron Lett. (2003), 44, 8653-8656; K. Sonogashira, J. Organomet. Chem. (2002), 653, 46-49).

In a further approach, compounds of formula (O), wherein $R^{26}$ is alkyl, optionally substituted vinyl, optionally substituted ethynyl, optionally substituted aryl or optionally substituted heteroaryl, may be prepared from compounds of formula (W) by reaction with a suitable organnostannane under Stille conditions (see, for example, R. Bedford, C. Cazin and S. Hazlewood (2002), 22, 2608-2609; S. Ley et al., Chem. Commun. (2002), 10, 1134-1135; G. Grasa and S. Nolan, Org. Lett. (2001), 3 (1), 119-122; T. Weskamp, V. Boehm, J. Organomet. Chem. (1999), 585 (2), 348-352; A. Littke and G. Fu, Angew. Chem. Int. Ed. (1999), 38 (16), 2411-2413; J. Stille et al., Org. Synth. (1992), 71, 97).

Compounds of formula (Q) may be prepared from compounds of formula (X), wherein Q and R''' are as defined for compounds of formula (W), by analogous methods using appropriate starting materials.

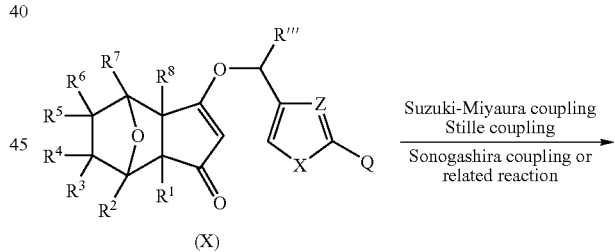

(X)

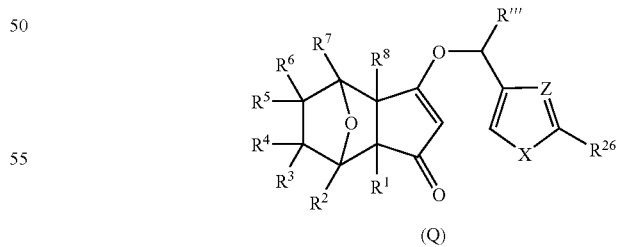

(Q)

Compounds of formula (W) may be prepared from compounds of formula (R), by reaction with compounds of formula (Y) wherein L is a suitable leaving group such as a halogen or an alkyl- or aryl-sulfonate, by processes analogous to those described above for the preparation of compounds of formula (O) from compounds of formula (R). Alternatively, compounds of formula (W) may be prepared by reaction of compounds of formula (R) with compounds of formula (Z) by processes analogous to those described above for the preparation of compounds of formula (O) from compounds of formula (R).

abromide, phosphorus oxybromide, oxalyl chloride or oxalyl bromide, optionally in a suitable solvent such as toluene, chloroform, dichloromethane with optionally the presence of

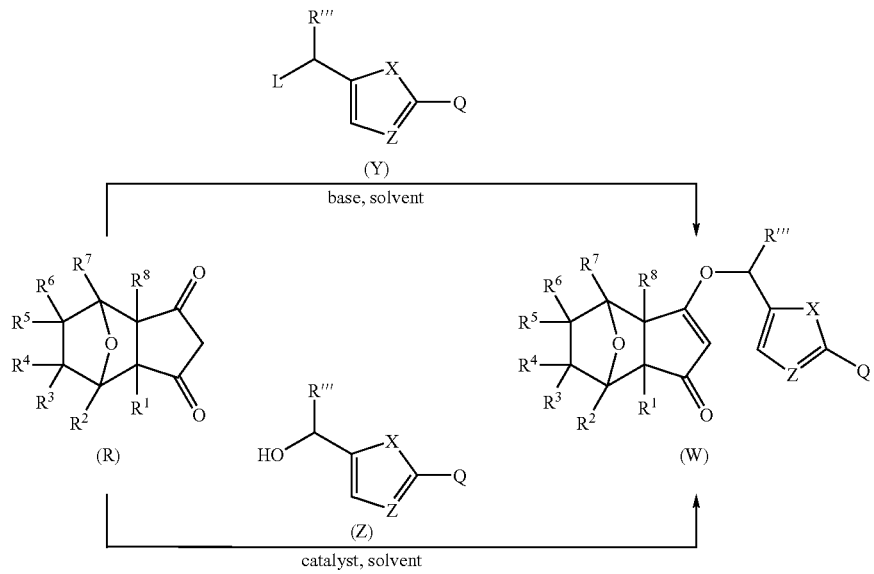

By analogous processes to those described above, compounds of formula (X) may be prepared from compounds of formula (R) by alkylation with compounds of formula (AA), wherein L is a suitable leaving group such as a halogen or an alkyl- or aryl-sulfonate, or by alkylation with compounds of formula (AB).

dimethylformamide, and the resulting vinyl halides of formula (AC), wherein Hal is chlorine or bromine may be converted by reaction with alcohols of formula (U), or of formula (V), or of formula (Z) or of formula (AB) optionally in the presence of a suitable base such as sodium hydride, sodium tert-butoxide, potassium tert-butoxide and a suitable solvent

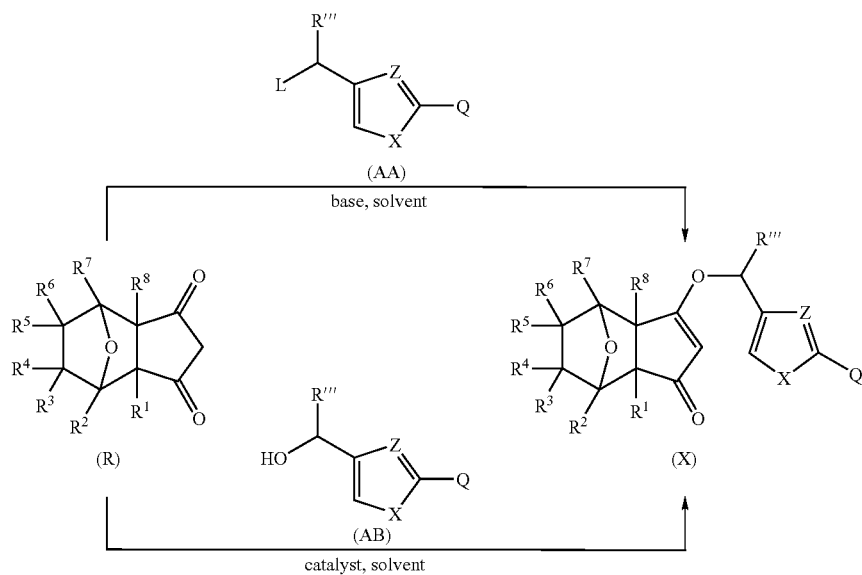

In an alternative approach, compounds of formula (R) may be treated with a halogenating agent such as phosphorus oxychloride, phosphorus pentachloride, phosphorus pentsuch as tetrahydrofuran, 1,4-dioxane, diethylene glycol dimethyl ether to give compounds of formula (O), formula (Q), formula (W) and formula (X) respectively:

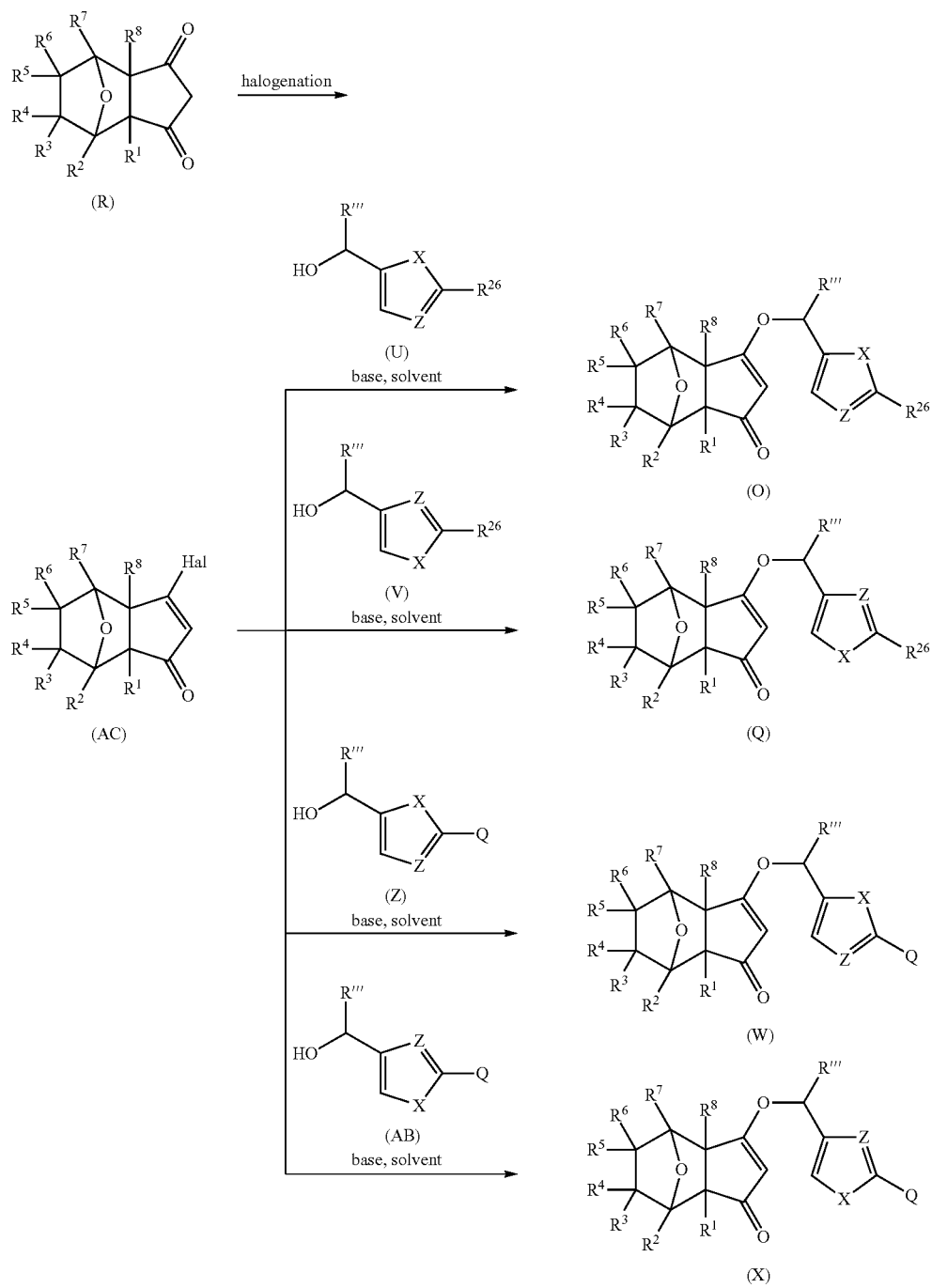

Compound of formula (R) wherein $R^3$ and $R^6$ are hydrogen may be prepared by reduction of compounds of formula (AD) under known conditions.

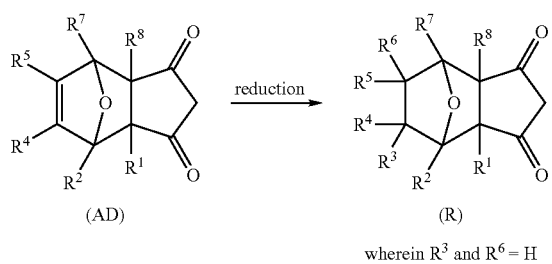

wherein $R^3$ and $R^6$ = H

Certain compounds of formula (AD) are alkenes, and as such undergo further reactions typical of alkenes to give additional compounds of formula (R) according to known procedures. Examples of such reactions include, but are not restricted to, halogenation, epoxidation, cyclopropanation, dihydroxylation and hydration of alkenes. In turn, these products may be transformed into additional compounds of formula (R) by methods described, for example, by Michael B. Smith and Jerry March, March's Advanced Organic Chemistry (Sixth Edition), John Wiley and Sons. Compounds of formula (R) wherein $R^4$ or $R^5$ are $C_1$-$C_6$alkoxy are enol ethers, and these may be hydrolysed to the corresponding ketone using standard procedures. In turn, the ketone may be further transformed, for example by ketalisation, oximation, reduction and the like under known conditions to give additional compounds of formula (R). Compounds of formula (AD) wherein $R^4$ or $R^5$ are halogen, preferably chloride or bromide, may undergo a cross-coupling reaction with a suitable coupling partner under conditions described in the literature for Suzuki-Miyaura, Sonogashira, Stille and related cross-coupling reactions to give additional compounds of formula (AD) (see, for example, C. J. O'Brien, M. G. Organ Angew. Chem. Int Ed. 2007, 46, 2768-2813; A. Suzuki, Journal of Organometallic Chemistry (2002), 653, 83; N. Miyaura and A Suzuki Chem. Rev. (1995), 95, 2457-2483).

Compounds of formula (AD) may be prepared by reacting compounds of formula (AE) with a cyclopentenediones of formula (AF), optionally in the presence of a Lewis acid catalyst, according to procedures described, for example by B. Zwanenburg et al., Tetrahedron (1989), 45 (22), 7109 and by M. Oda et al., Chem. Lett. (1977), 307.

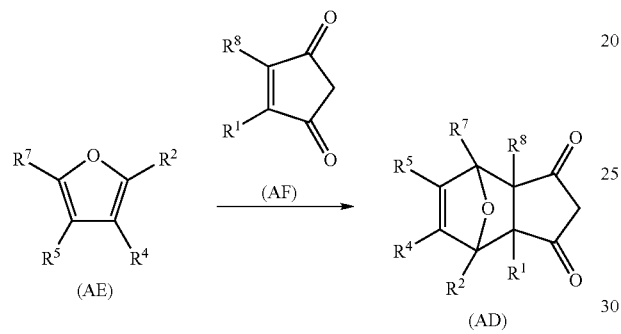

Compounds of formula (AE) and formula (AF) are known compounds or may be made from known compounds by known methods.

Compounds of formula (S), formula (T), formula (U), formula (V), formula (Y), formula (Z), formula (AA) and formula (AB) are known or may be prepared by known methods from known compounds (see, for example T. T. Denton, X. Zhang, J. R. Cashman, J. Med. Chem. (2005), 48, 224-239; J. Reinhard, W. E. Hull, C.-W. von der Lieth, U. Eichhorn, H.-C. Kliem, J. Med. Chem. (2001), 44, 4050-4061; H. Kraus and H. Fiege, DE19547076; M. L. Boys, L. A. Schretzman, N. S. Chandrakumar, M. B. Tollefson, S. B. Mohler, V. L. Downs, T. D. Penning, M. A. Russell, J. A. Wendt, B. B. Chen, H. G. Stenmark, H. Wu, D. P. Spangler, M. Clare, B. N. Desai, I. K. Khanna, M. N. Nguyen, T. Duffin, V. W. Engleman, M. B. Finn, S. K. Freeman, M. L. Hanneke, J. L. Keene, J. A. Klover, G. A. Nickols, M. A. Nickols, C. N. Steininger, M. Westlin, W. Westlin, Y. X. Yu, Y. Wang, C. R. Dalton, S. A. Norring, Bioorg. Med. Chem. Lett. (2006), 16, 839-844; A. Silberg, A. Benko, G. Csavassy, Chem. Ber. (1964), 97, 1684-1687; K. Brown and R. Newbury, Tetrahedron Lett. (1969), 2797; A. Jansen and M. Szelke, J. Chem. Soc. (1961), 405; R. Diaz-Cortes, A. Silva and L. Maldonado, Tetrahedron Lett. (1997), 38(13), 2007-2210; M. Friedrich, A. Waechtler and A De Meijure, Synlett. (2002), 4, 619-621; F. Kerdesky and L. Seif, Synth. Commun. (1995), 25 (17), 2639-2645; Z. Zhao, G. Scarlato and R. Armstrong., Tetrahedron Lett. (1991), 32 (13), 1609-1612; K-T. Kang and S. Jong, Synth. Commun. (1995), 25 (17), 2647-2653; M. Altamura and E. Perrotta, J. Org. Chem. (1993), 58 (1), 272-274).

Furthermore, compounds of formula (AG) wherein Q is an atom or group suitable for cross-coupling chemistry (such as a halogen or a haloalkylsulfonate) may undergo Suzuki-Miyaura, Stille, Sonogashira and related reactions under known conditions to give additional compounds of formula N. Compounds of formula (AG) may be prepared by rearranging compounds of formula (W) under conditions similar to those used to convert compounds of formula (O) to compounds of formula (N):

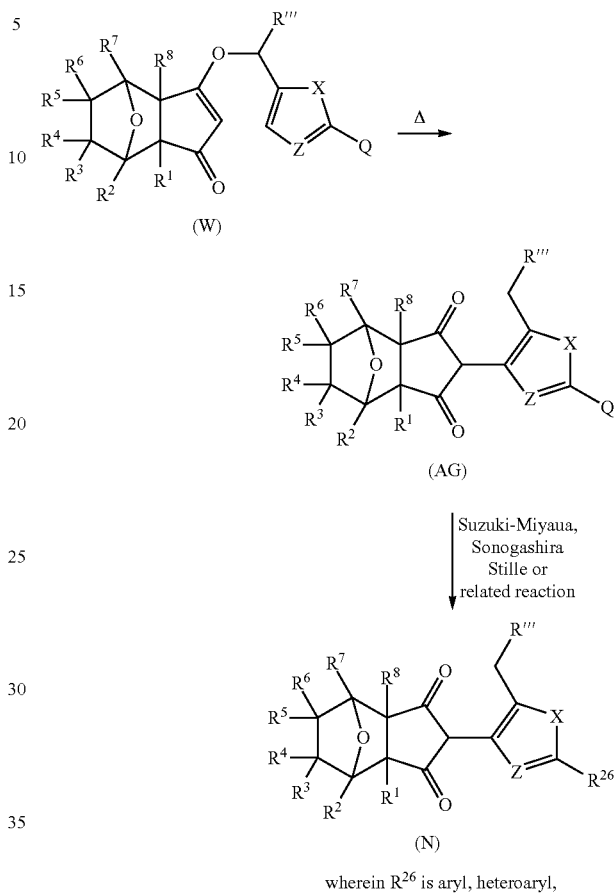

wherein $R^{26}$ is aryl, heteroaryl, alkenyl, alkynyl or similar

Those skilled in the art will appreciate that transformations of this type are not restricted to compounds of formula (AG), but may in general be applied to any compound of formula (I) where Het is a heterocycle substituted by an atom or group suitable for further derivatisation.

Those skilled in the art will appreciate that compounds of formula (I) may contain a heteroaromatic moiety bearing one or more substituents capable of being transformed into alternative substituents under known conditions, and that these compounds may themselves serve as intermediates in the preparation of additional compounds of formula (I). For example, a heterocycle of formula (N) wherein $R^{26}$ is alkenyl or alkynyl, may be reduced to compounds of formula (N) wherein $R^{26}$ is alkyl under known conditions.

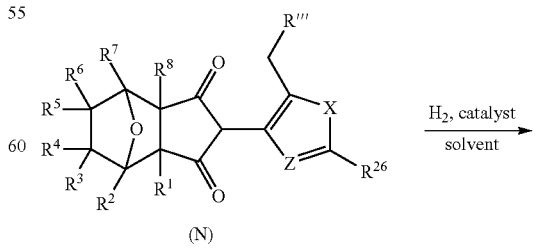

wherein $R^{26}$ is alkyl or alkenyl

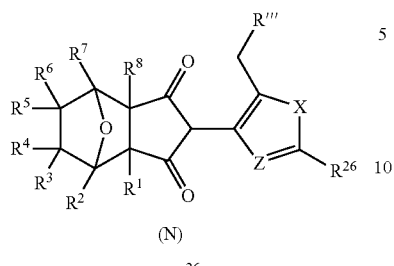

(N)

wherein R²⁶ is alkyl

In a further approach to compounds of formula (A), wherein Het is a group of formula (R₂), X is S, and Y is N, compounds of formula (AH) wherein L is a suitable leaving group such as a halogen or an alkyl- or haloalkylsulfonate, may be treated with compounds of formula (AJ) in the presence of a suitable base (such as triethylamine or pyridine), and optionally in a suitable solvent (such as water, acetone, ethanol or isopropanol) according to known procedures, (see, for example, E. Knott, J. Chem. Soc. (1945), 455; H. Brederick, R. Gompper, Chem. Ber. (1960), 93, 723; B. Friedman, M. Sparks and R. Adams, J. Am. Chem. Soc. (1937), 59, 2262).

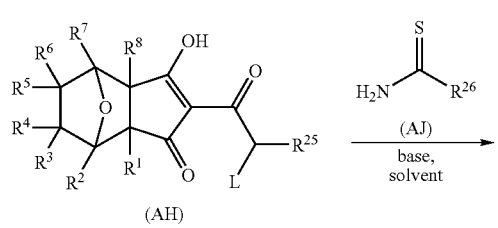

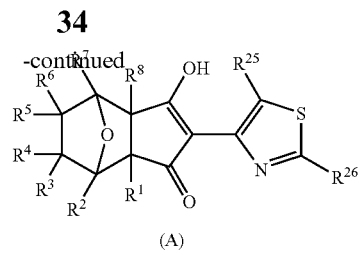

(A)

where Het is (R²)
X is S and Z is N

Alternatively, compounds of formula (AH) may be treated with thiourea, by known procedures (see, for example, V. Pshenichniya, O. Gulyakevich and V. Kripach, Chemistry of Heterocyclic Compounds (1990), 10, 1409-1412), and the resulting products of formula (AK) may be converted into additional compounds of formula (A) by conversion to halides of formula (AL), wherein Hal is chlorine, bromine or iodine, under Sandmeyer conditions, and compounds of formula (AL) may be converted to compounds of formula (A) by cross-coupling under known conditions for the Suzuki-Miyaura, Sonogashira, Stille and related reactions, as described previously.

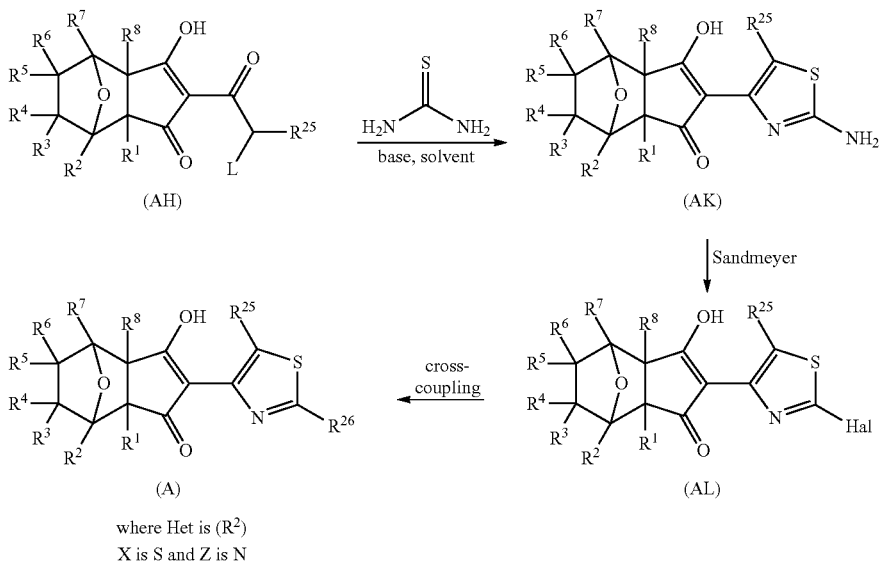

(A)

where Het is (R²)
X is S and Z is N

Compounds of formula (AH) may be prepared from compounds of formula (R) under known conditions (see, for example, V. Pshenichniya, O. Gulyakevich and V. Kripach, Chemistry of Heterocyclic Compounds (1990), 10, 1409-1412; V. Pshenichniya, O. Gulyakevich and V. Kripach, Russian Journal of Organic Chemistry (1989), 25 (9), 1882-1888).

In a further approach, compounds of formula (A) may be prepared by reaction of compounds of formula (R) with a heteroaryl lead tricarboxylates under conditions described in the literature (for example see, J. T. Pinhey, B. A. Rowe, Aust. J. Chem. (1979), 32, 1561-6; J. Morgan, J. T. Pinhey, J. Chem. Soc. Perkin Trans. 1 (1990), 3, 715-20 and J. T. Pinhey, Roche, E. G. J. Chem. Soc. Perkin Trans. 1 (1988), 2415-21). Preferably the heteroaryl lead tricarboxylates are heteroaryl triacetates of formula (AM) and the reaction is conducted in the presence of a suitable ligand (for example N,N-dimethylaminopyridine, pyridine, imidazole, bipyridine, and 1,10-phenanthroline, preferably one to ten equivalents of N,N-dimethylaminopyridine with respect to compound (R)) and in a suitable solvent (for example chloroform, dichloromethane and toluene, preferably chloroform and optionally in the presence of a co-solvent such as toluene) at 25° C. to 100° C. (preferably 60-90° C.).

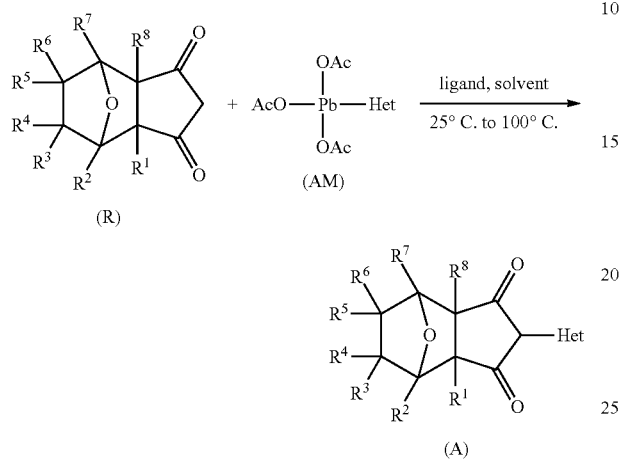

Compounds of formula (AM) may be prepared from compounds of formula (AN) by treatment with lead tetraacetate in a suitable solvent (for example chloroform) at 25° C. to 100° C. (preferably 25-50° C.), optionally in the presence of a catalyst such as mercury diacetate, according to procedures described in the literature (for example see, K. Shimi, G. Boyer, J-P. Finet and J-P. Galy, Letters in Organic Chemistry (2005), 2, 407-409; J. Morgan and J. T. Pinhey, J. Chem. Soc. Perkin Trans. 1 (1990), 3, 715-20).

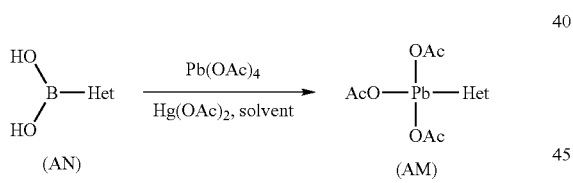

Preferred coupling partners include heteroarylboronic acids, ($AN_1$) to ($AN_8$), wherein $R^{25}$, $R^{26}$, $R^{27}$, $R^{28}$, $R^{29}$, $R^{30}$, X, $W^1$, $W^2$, $W^3$, $W_4$ and Z are as defined above.

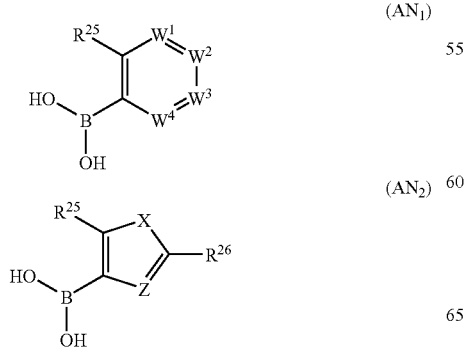

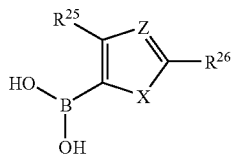

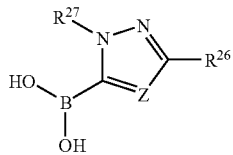

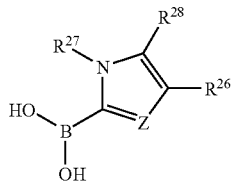

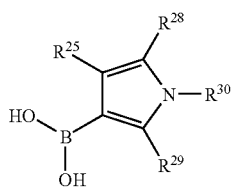

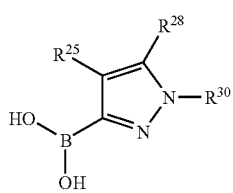

Heteroarylboronic acids of formula (AN) are known compounds, or may be prepared from known compounds by known methods (see for example A. Voisin et al., Tetrahedron (2005), 1417-1421; A. Thompson et al, Tetrahedron (2005), 61, 5131-5135; K. Billingsley and S. Buchwald, J. Am. Chem. Soc. (2007), 129, 3358-3366; N. Kudo, M. Pauro and G. Fu, Angew. Chem. Int. Ed. (2006), 45, 1282-1284; A. Ivachtchenko et al., J. Heterocyclic Chem. (2004), 41(6), 931-939; H. Matondo et al., Synth. Commun. (2003), 33 (5) 795-800; A. Bouillon et al., Tetrahedron (2003), 59, 10043-10049; W. Li et al., J. Org. Chem. (2002), 67, 5394-5397; C. Enguehard et al., J. Org. Chem. (2000), 65, 6572-6575; H—N Nguyen, X. Huang and S. Buchwald, J. Am. Chem. Soc. (2003), 125, 11818-11819, and references therein).

In a further approach, compounds of formula (A) may be prepared from compounds of formula (AO) by reaction with heteroaryl boronic acids of formula (AN), in the presence of a suitable palladium catalyst and a base, and preferably in a suitable solvent.

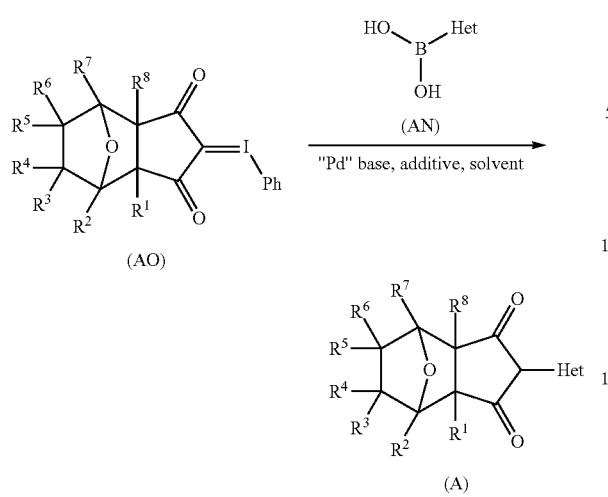

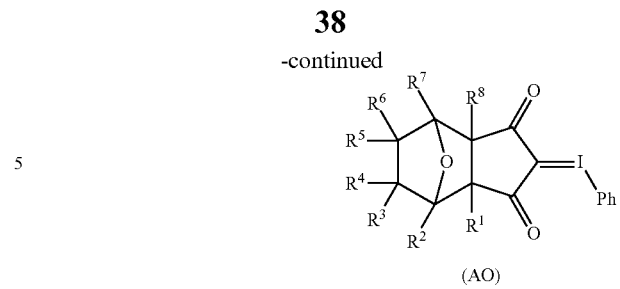

Suitable palladium catalysts are generally palladium(II) or palladium(0) complexes, for example palladium(II) dihalides, palladium(II) acetate, palladium(II) sulfate, bis(triphenylphosphine)palladium(II) dichloride, bis(tricyclopentylphosphine)palladium(II) dichloride, bis(tricyclohexylphosphine)palladium(II) dichloride, bis(dibenzylideneacetone)palladium(0) or tetrakis(triphenylphosphine)palladium(0). The palladium catalyst can also be prepared in situ from palladium(II) or palladium (0) compounds by complexing with the desired ligands, by, for example, combining the palladium(II) salt to be complexed, for example palladium(II) dichloride ($PdCl_2$) or palladium(II) acetate ($Pd(OAc)_2$), together with the desired ligand, for example triphenylphosphine ($PPh_3$), tricyclopentylphosphine or tricyclohexylphosphine and the selected solvent, with compounds of formula (AO), a heteroaromatic boronic acid of formula (AN) and a base. Also suitable are bidendate ligands, for example 1,1'-bis(diphenylphosphino)ferrocene or 1,2-bis(diphenylphosphino)ethane. By heating the reaction medium, the palladium(II) complex or palladium (0) complex desired for the C—C coupling reaction is thus formed "in situ", and then initiates the C—C coupling reaction. The palladium catalysts are used in an amount of from 0.001 to 50 mol %, preferably in an amount of from 0.1 to 15 mol %, based on the compound of formula (AO). More preferably the palladium source is palladium acetate, the base is lithium hydroxide and the solvent is a mixture of 1,2-dimethoxyethane and water in a ratio of 4:1 to 1:4. The reaction may also be carried out in the presence of other additives, such as tetralkylammonium salts, for example, tetrabutylammonium bromide:

Compounds of formula (AO) may be prepared from compounds of formula (R) by treatment with (diacetoxy)iodobenzene according to the procedures of K. Schank and C. Lick, Synthesis (1983), 392; or of Z Yana et al., Ora. Lett. (2002), 4 (19), 3333.

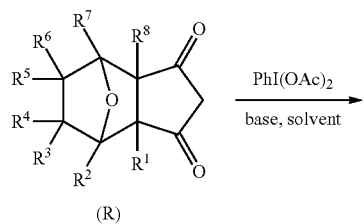

In a further approach, compounds of formula (A) may be prepared from compounds of formula (I) or IA (wherein G is $C_1$-$C_4$ alkyl) by hydrolysis, preferably in the presence of an acid catalyst such as hydrochloric acid and optionally in the presence of a suitable solvent such as tetrahydrofuran or 1,4-dioxane. Compounds of formula (I) (wherein G is $C_1$-$C_4$ alkyl) may be prepared by reacting compounds of formula (AP) (wherein G is $C_1$-$C_4$alkyl, and Hai is a halogen, preferably bromine or iodine), with a heteroaryl boronic acid, Het-$B(OH)_2$, of formula (AN) in the presence of a suitable palladium catalyst (for example 0.001-50% palladium(II) acetate with respect to compound (AP)) and a base (for example 1 to 10 equivalents potassium phosphate with respect to compound (AP)) and preferably in the presence of a suitable ligand (for example 0.001-50% (2-dicyclohexylphosphino)-2',6'-dimethoxybiphenyl with respect to compound (AP)), and in a suitable solvent (for example toluene), preferably between 25° C. and 200° C. Similar couplings are known in the literature (see for example, Y. S. Song, B. T. Kim and J.-N. Heo, Tetrahedron Letters (2005), 46 (36), 5987-5990).

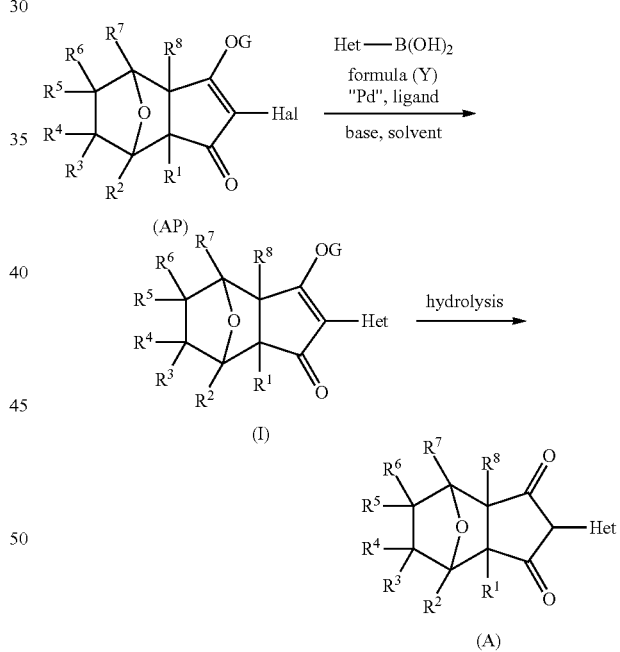

Compounds of formula (AP) may be prepared by halogenating compound of formula (R), followed by alkylation of the resulting halides of formula (AQ) with a $C_1$-$C_4$alkyl halide or tri-$C_1$-$C_4$-alkylorthoformate under known conditions, for example by the procedures of R. G. Shepherd and A. C. White (J. Chem. Soc. Perkin Trans. 1 (1987), 2153-2155) and Y.-L. Lin et al. (Bioorg. Med. Chem. (2002), 10, 685-690). Alternatively, compounds of formula (AP) may be prepared by alkylating compounds of formula (R) with a $C_1$-$C_4$ alkyl halide or a tri-$C_1$-$C_4$-alkylorthoformate, and halogenating the resulting enone of formula (AR) under known conditions (see for example Y. S. Song, B. T. Kim and J.-N. Heo, Tetrahedron Letters (2005), 46 (36), 5987-5990).

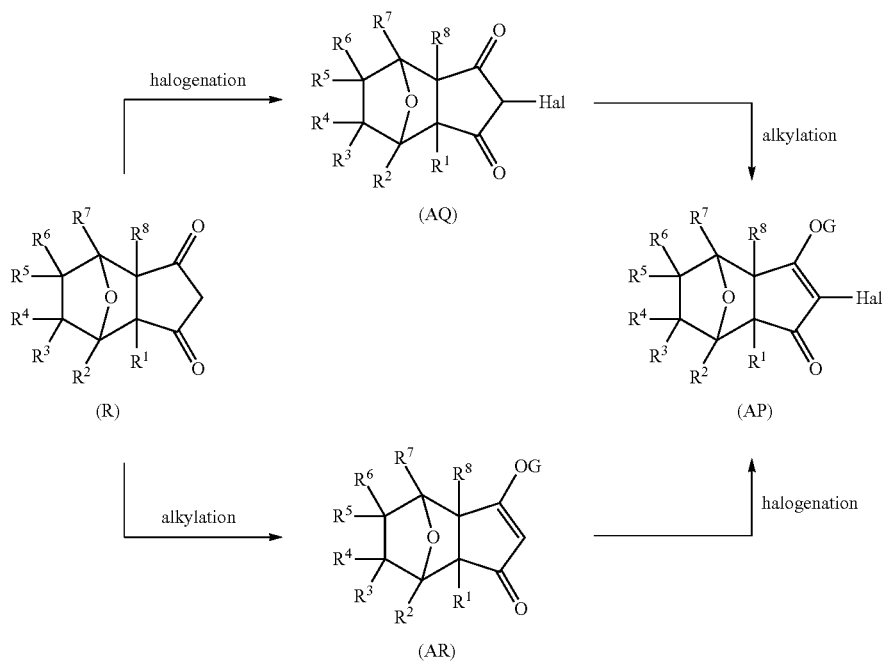

In a further approach, compounds of formula (A) may be prepared by reacting compounds of formula (R) with suitable heteroaryl halides (Het-Hal where Hal is, for example, an iodide or bromide), in the presence of a suitable palladium catalyst (for example 0.001-50% palladium(II) acetate with respect to compound (R)) and a base (for example 1 to 10 equivalents potassium phosphate with respect to compound (R)) and preferably in the presence of a suitable ligand (for example 0.001-50% (2-dicyclohexylphosphino)-2',4',6'-thisopropylbiphenyl with respect to compound (R)), and in a suitable solvent (for example 1,4-dioxane), preferably between 25° C. and 200° C. Similar couplings are known in the literature (see for example, J. M. Fox, X. Huang, A. Chieffi, and S. L. Buchwald, J. Am. Chem. Soc. (2000), 122, 1360-1370; B. Hong et al. WO 2005/000233). Alternatively, compounds of formula (A) may be prepared by reacting compounds of formula (R) with suitable heteroaryl halides (Het-Hal where Hal is, for example, an iodide or bromide) in the presence of a suitable copper catalyst (for example 0.001-50% copper(I) iodide with respect to compound (R)) and a base (for example 1 to 10 equivalents potassium carbonate with respect to compound (R)) and preferably in the presence of a suitable ligand (for example 0.001-50% L-proline with respect to compound (R)), and in a suitable solvent (for example dimethylsulfoxide), preferably between 25° C. and 200° C. Similar couplings are known in the literature for aryl halides (see for example, Y. Jiang, N. Wu, H. Wu, and M. He, Synlett (2005), 18, 2731-2734).

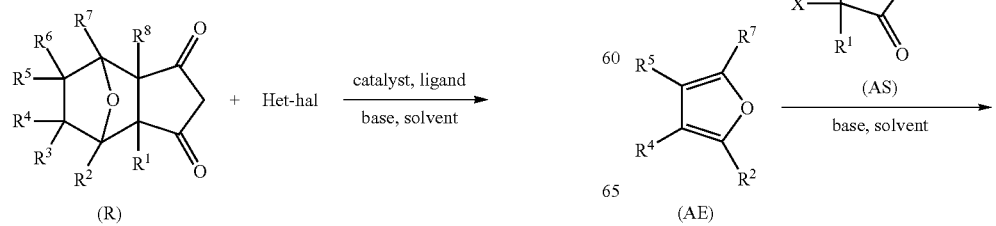

-continued

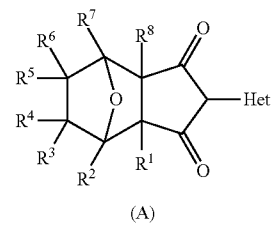

Additional compounds of formula (A) may be prepared by hydrolysing compounds of formula (I), wherein G is $C_1$-$C_6$ alkyl under aqueous acidic conditions. Compounds of formula (I), wherein G is $C_1$-$C_6$ alkyl and $R^3$ and $R^6$ form a bond, may be prepared by reacting compounds of formula (AS), wherein G is $C_1$-$C_6$ alkyl, X is halogen or other suitable leaving group (such as an alkyl or arylsulfonate, or an arylselenoxide), with compounds of formula (AE), neat or in a suitable solvent, and optionally in the presence of a suitable base.

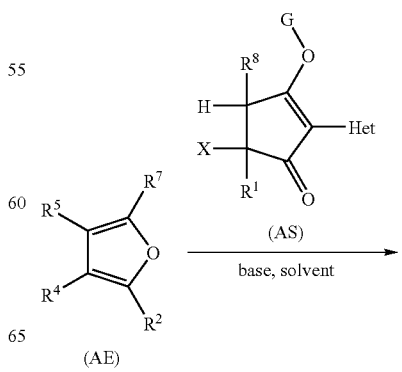

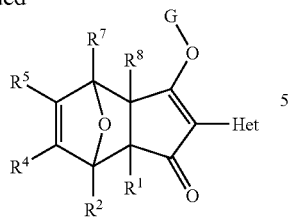

(I) wherein G is $C_1$-$C_6$ alkyl
and $R^3$ and $R^6$ form a bond

Suitable solvents include toluene, and suitable bases include organic bases such as 1,8-diazabicyclo[5.4.0]undec-7-ene.

Compounds of formula (AS), wherein G is $C_1$-$C_6$alkyl and X is halogen may be prepared from compounds of formula (AT), wherein G is $C_1$-$C_6$alkyl, under known conditions.

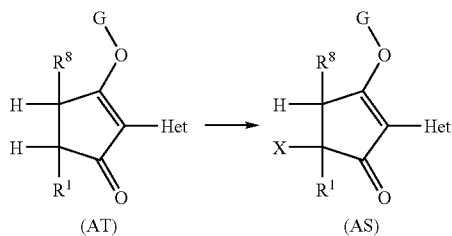

For example, compounds of formula (AS) wherein X is chlorine may be prepared by reacting compounds of formula (AT) with copper(II) chloride and lithium chloride according to the procedure of E. M. Kosower et al., J. Org. Chem. (1963), 28, 630-633.

Compounds of formula (AT) are known compounds or may be made from known compounds by known methods (see, for example, Y. S. S. Song, B. T. Kim and J-N Heo, Tetrahedron Lett., 46 (2005) 5977-5990). Alternatively, compounds of formula (AT) wherein G is $C_1$-$C_6$alkyl may be prepared by alkylation of compounds of formula (AT), wherein G is hydrogen under known conditions. Compounds of formula (AT), wherein G is hydrogen, are known, or may be prepared from known compounds by known methods (see, for example, DE10118310).

Alternatively, in a further approach to compounds of formula (AT), compounds of formula (AU), which are compounds of formula (AT) wherein G is hydrogen and Het is ($R_2$) when $R^{25}$ is $CH_2R'''$ and $R'''$ is hydrogen, alkyl or halogenoalkyl (preferably hydrogen, methyl or trifluoromethyl), may be prepared by thermal rearrangement of compounds of formula (AV), optionally in the presence of a suitable solvent and optionally under microwave irradiation.

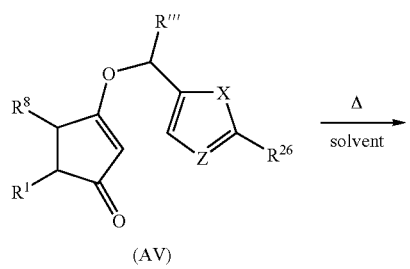

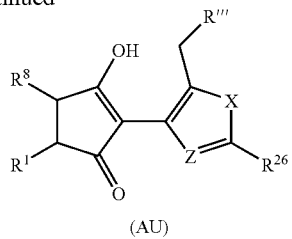

Preferably, the rearrangement is effected by heating compounds of formula (AV) at temperatures of between 120-300° C., optionally in a suitable solvent such as 1,2-dimethoxyethane, diethylene glycol methyl ether, triglyme, tetraglyme, xylene, mesitylene or Dowtherm®, and optionally under microwave irradiation.

Similarly, compounds of formula (AW), which are compounds of formula (AT) wherein G is hydrogen and Het is ($R_3$) when $R^{25}$ is $CH_2R'''$ and $R'''$ is hydrogen, alkyl or halogenoalkyl (preferably hydrogen, methyl or trifluoromethyl), may be prepared from compounds of formula (AX) using similar methods.

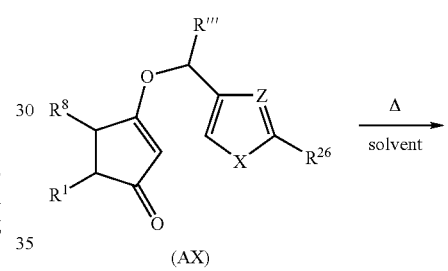

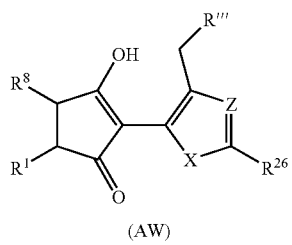

Compounds of formula (AV) may be prepared from compounds of formula (AY) by alkylation with compounds of formula (S), wherein L is a suitable leaving group such as a halogen or an alkyl- or aryl-sulfonate, optionally in the presence of a suitable base and optionally in a suitable solvent as described above for the alkylation of compounds of formula (A)

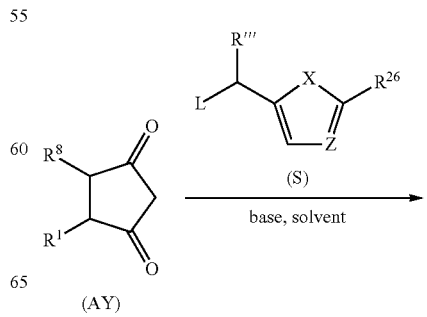

-continued

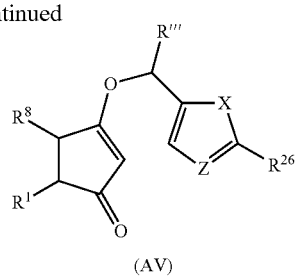

(AV)

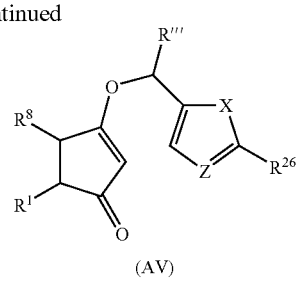

(AV)

Similarly, compounds of formula (AX) may be prepared from compounds of formula (AY) by alkylation with compounds of formula (T), wherein L is a suitable leaving group such as a halogen or an alkyl- or aryl-sulfonate, under similar conditions.

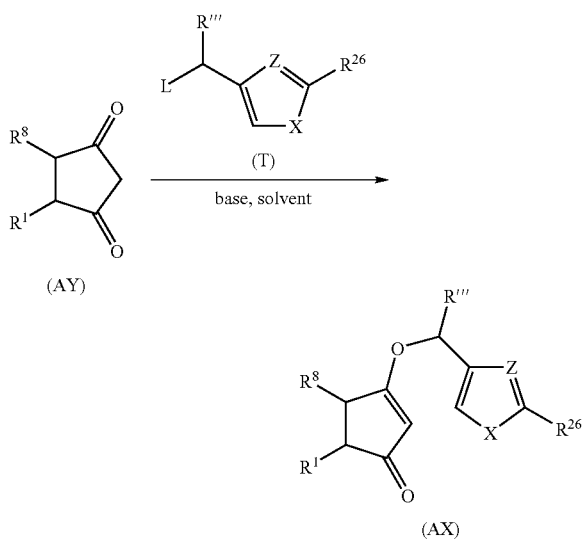

In an alternative approach, compounds of formula (AV) may be prepared from compounds of formula (AY) by condensation with alcohols of formula (U), optionally in the presence of a suitable acid catalyst such as p-toluenesulfonic acid, or a Lewis acid catalyst, for example, ytterbium (III) trifluoromethanesulfonate, lanthanum (III) trifluoromethanesulfonate, sodium tetrachloroaurate (III) dihydrate, titanium (IV) chloride, indium (III) chloride or aluminium chloride, and optionally in a suitable solvent. Suitable solvents are selected to be compatible with the reagents used, and include, for example, toluene, ethanol or acetonitrile. Similar approaches have been described by, for example, M. Curini; F. Epifano, S. Genovese, Tetrahedron Lett. (2006), 47, 4697-700 and A. Arcadi, G. Bianchi, S. Di Giuseppe, F. Marinelli, Green Chemistry (2003), 5, 64-7.

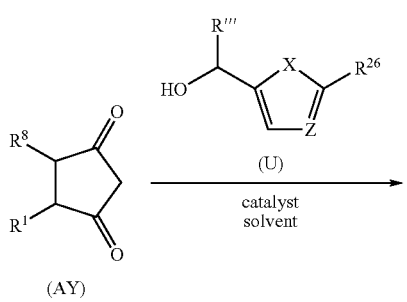

Alternatively, the condensation may be effected in the presence of suitable coupling agents such as 2-chloro-1-methylpyridinium iodide, N,N'-dicyclohexylcarbodiimide, 1,(3-dimethylaminopropyl)-3-ethylcarbodiimimde and N,N-carbodiimidazole and optionally a suitable base such a triethylamine or pyridine in a suitable solvent such as tetrahydrofuran, acetonitrile or dichloromethane, or in the presence of a triarylphosphine (such as triphenylphosphine) and a dialkyl azidodicarboxylate (preferably diethyl azidodicarboxylate or diisopropyl azidodicarboxylate) and in a suitable solvent such as diethyl ether, tetrahydrofuran or 1,4-dioxane as described, for example, by O. Mitsunobu, Synthesis (1981), 1, 1-28.

Using similar processes, compounds of formula (AX) may be prepared by reaction of compounds of formula (AY) with compounds of formula (V).

Additional compounds of formula (AV) wherein $R^{26}$ is an aromatic or heteroaromatic moiety, or is an alkyl, alkenyl or alkynyl group, may be prepared by the reaction of compounds of formula (AZ), wherein Q is an atom or group suitable for undergoing cross-coupling reactions (for example Q is chlorine, bromine or iodine, or a haloalkylsulfonate such as trifluoromethanesulfonate), and R''' is as defined for compound of formula (AW), with a suitable coupling partner under conditions described in the literature for Suzuki-Miyaura, Sonogashira, Stille and related cross-coupling reactions.

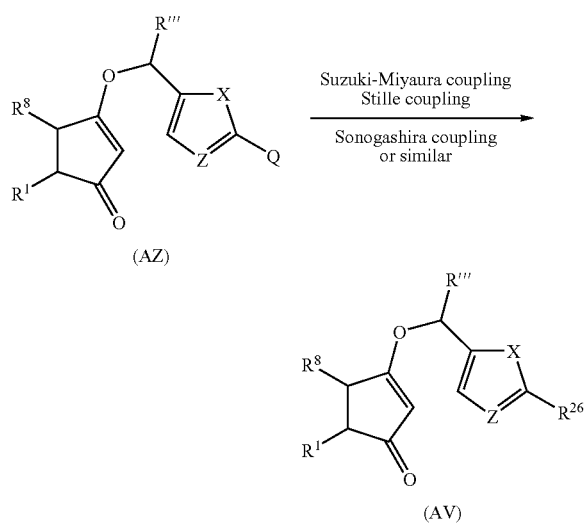

(AZ) → (AV)   Suzuki-Miyaura coupling / Stille coupling / Sonogashira coupling or similar

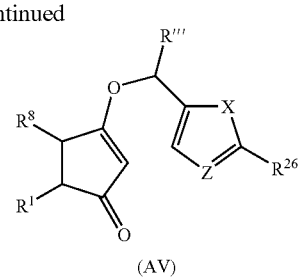

(AV)

For example, compounds of formula (AZ) may be treated with aryl-, heteroaryl-, alkyl-, alkenyl- or alkynylboronic acids, $R^{26}$—$B(OH)_2$, boronate esters, $R^{26}$—$B(OR'''')_2$, wherein R'''' is $C_1$-$C_6$alkyl or $R^{26}$—$B(OR'''')_2$ represents cyclic boronate esters derived from a $C_1$-$C_6$diol (especially preferred are cyclic boronate esters derived from pinacol), or a metal (especially potassium) aryl-, heteroaryl, alkyl-, alkenyl- and alkynyltrifluoroborate salts, $M^+[R^{26}$—$BF_3]^-$ in the presence of a suitable palladium catalyst, a suitable ligand and a suitable base in the presence of a suitable solvent, under Suzuki-Miyaura conditions
(see, for example K. Billingsley and S. Buchwald, J. Am. Chem. Soc. (2007), 129, 3358-3366; H. Stefani, R. Cella and A. Vieira, Tetrahedron (2007), 63, 3623-3658; N. Kudo, M. Perseghini and G. Fu, Angew. Chem. Int. Ed. (2006), 45, 1282-1284; A. Roglans, A. Pla-Quintana and M. Moreno-Mañas, Chem. Rev. (2006), 106, 4622-4643; J-H Li, Q-M Zhu and Y-X Xie, Tetrahedron (2006), 10888-10895; S. Nolan et al., J. Org. Chem. (2006), 71, 685-692; M. Lysén and K. Köhler, Synthesis (2006), 4, 692-698; K. Anderson and S. Buchwald, Angew. Chem. Int. Ed. (2005), 44, 6173-6177; Y. Wang and D. Sauer, Org. Lett. (2004), 6 (16), 2793-2796; I. Kondolff, H. Doucet and M, Santelli, Tetrahedron, (2004), 60, 3813-3818; F. Bellina, A. Carpita and R. Rossi, Synthesis (2004), 15, 2419-2440; H. Stefani, G. Molander, C-S Yun, M. Ribagorda and B. Biolatto, J. Org. Chem. (2003), 68, 5534-5539; A. Suzuki, Journal of Organometallic Chemistry (2002), 653, 83; G. Molander and C-S Yun, Tetrahedron (2002), 58, 1465-1470; G. Zou, Y. K. Reddy and J. Falck, Tetrahedron Lett. (2001), 42, 4213-7215; S. Darses, G. Michaud and J-P, Genêt, Eur. J. Org. Chem. (1999), 1877-1883).

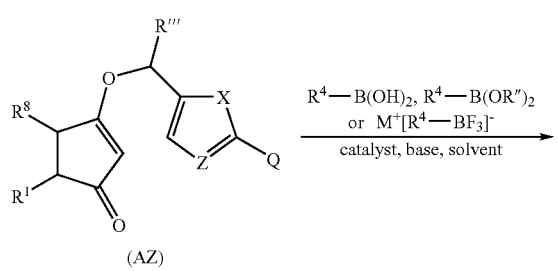

(AZ) + $R^4$—$B(OH)_2$, $R^4$—$B(OR'')_2$ or $M^+[R^4$—$BF_3]^-$, catalyst, base, solvent Alternatively, compounds of formula (AV), wherein $R^{26}$ is an optionally substituted acetylene, may be prepared from compounds of formula (AZ) by reacting with a terminal alkyne, $R^{26}$—H, in the presence of a suitable palladium catalyst and optionally in the presence of a suitable copper co-catalyst, a suitable ligand, a suitable base and a suitable additive under conditions known to effect the Sonogashira coupling (see, for example, U. Sorenson and E Pombo-Villar, Tetrahedron (2005), 2697-2703; N. Leadbeater and B. Tominack, Tetrahedron Lett. (2003), 44, 8653-8656; K. Sonogashira, J. Organomet. Chem. (2002), 653, 46-49).

In a further approach, compounds of formula (AV), wherein $R^{26}$ is alkyl, optionally substituted vinyl, optionally substituted ethynyl, optionally substituted aryl or optionally substituted heteroaryl, may be prepared from compounds of formula (AZ) by reaction with a suitable organnostannane under Stille conditions (see, for example, R. Bedford, C. Cazin and S. Hazlewood (2002), 22, 2608-2609; S. Ley et al., Chem. Commun. (2002), 10, 1134-1135; G. Grasa and S. Nolan, Org. Lett. (2001), 3 (1), 119-122; T. Weskamp, V. Boehm, J. Organomet. Chem. (1999), 585 (2), 348-352; A. Littke and G. Fu, Angew. Chem. Int. Ed. (1999), 38 (16), 2411-2413; J. Stille et al., Org. Synth. (1992), 71, 97).

Compounds of formula (AX) may be prepared from compounds of formula (BA), wherein Q and R''' are as defined for compounds of formula (AZ), by analogous methods using appropriate starting materials.

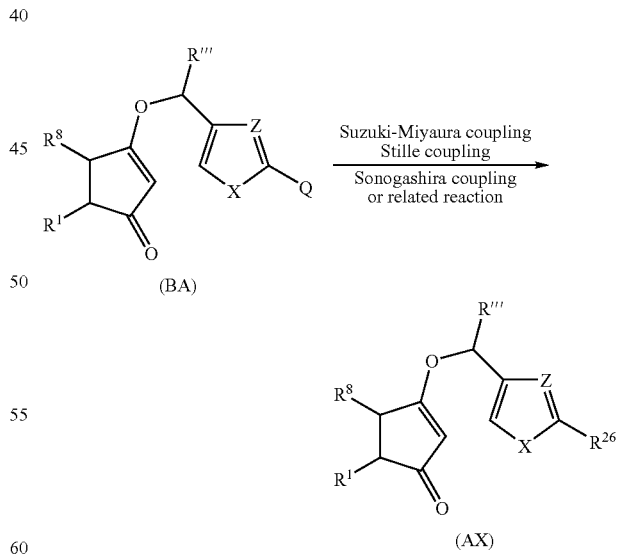

(BA) → (AX)   Suzuki-Miyaura coupling / Stille coupling / Sonogashira coupling or related reaction Compounds of formula (AZ) may be prepared from compounds of formula (AY), by reaction with compounds of formula (Y) wherein L is a suitable leaving group such as a halogen or an alkyl- or aryl-sulfonate, by processes analogous to those described above for the preparation of compounds of formula (AV) from compounds of formula (AY). Alternatively, compounds of formula (AZ) may be prepared by reaction of compounds of formula (AY) with compounds of formula (Z) by processes analogous to those described above for the preparation of compounds of formula (AV) from compounds of formula (AY).

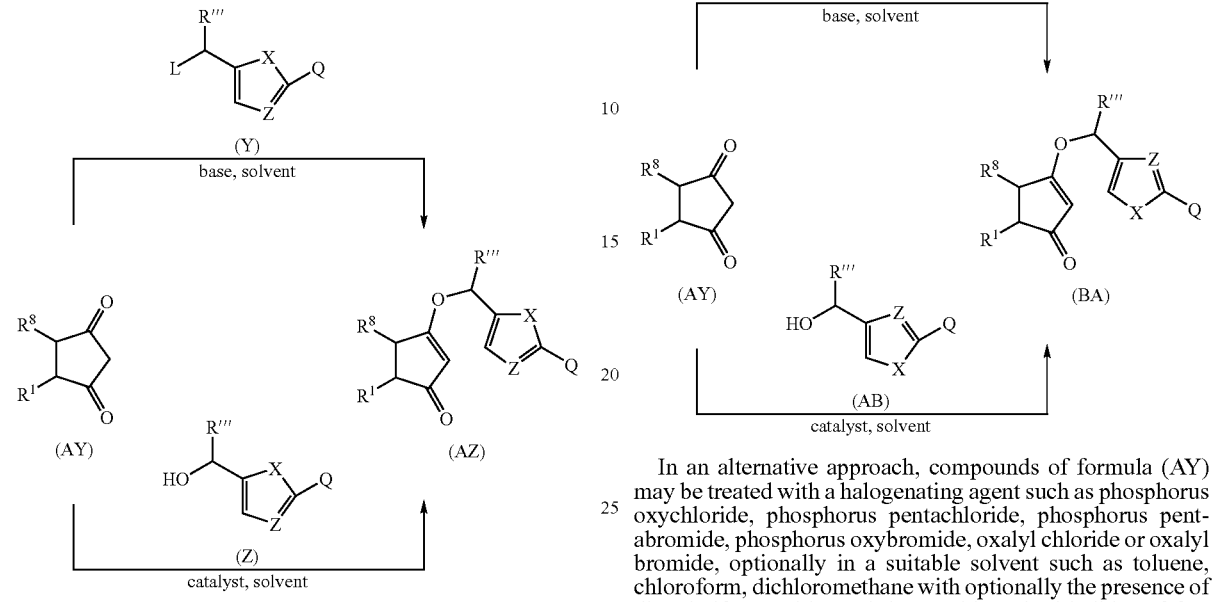

By analogous processes to those described above, compounds of formula (BA) may be prepared from compounds of formula (AY) by alkylation with compounds of formula (AA), wherein L is a suitable leaving group such as a halogen or an alkyl- or aryl-sulfonate, or by alkylation with compounds of formula (AB).

In an alternative approach, compounds of formula (AY) may be treated with a halogenating agent such as phosphorus oxychloride, phosphorus pentachloride, phosphorus pentabromide, phosphorus oxybromide, oxalyl chloride or oxalyl bromide, optionally in a suitable solvent such as toluene, chloroform, dichloromethane with optionally the presence of dimethylformamide, and the resulting vinyl halides of formula (BB), wherein Hal is chlorine or bromine may be converted by reaction with alcohols of formula (U), or of formula (V), or of formula (Z) or of formula (AB) optionally in the presence of a suitable base such as sodium hydride, sodium tert-butoxide, potassium tert-butoxide and a suitable solvent such as tetrahydrofuran, 1,4-dioxane, diethylene glycol dimethyl ether to give compounds of formula (AV), formula (AX), formula (AZ) and formula (BA) respectively:

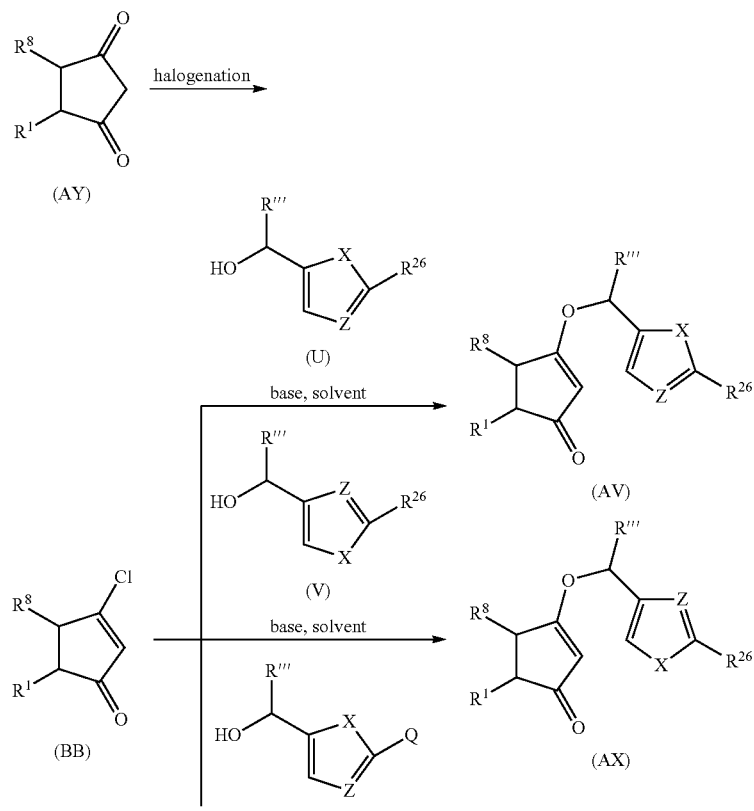

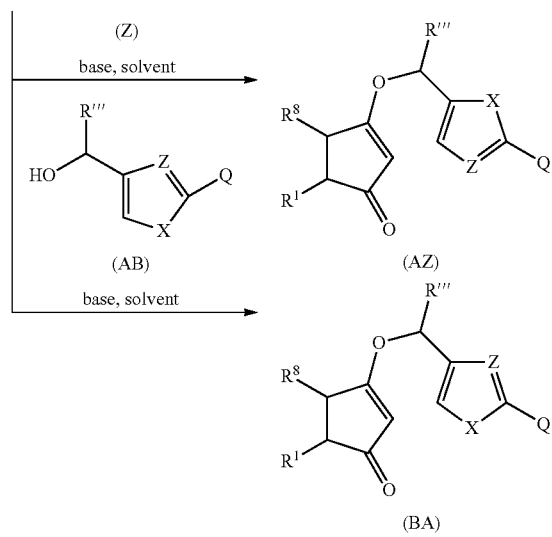

Compounds of formula (AY) are known compounds or may be made from known compounds by known methods.

Furthermore, compounds of formula (BC) wherein Q is an atom or group suitable for cross-coupling chemistry (such as a halogen or a haloalkylsulfonate) may undergo Suzuki-Miyaura, Stille, Sonogashira and related reactions under known conditions to give additional compounds of formula N. Compounds of formula (BC) may be prepared by rearranging compounds of formula (AZ) under conditions similar to those used to convert compounds of formula (AV) to compounds of formula (AU):

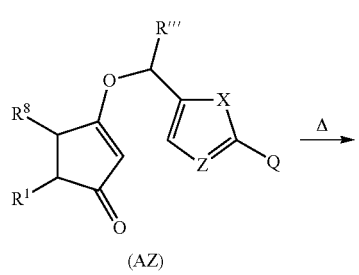

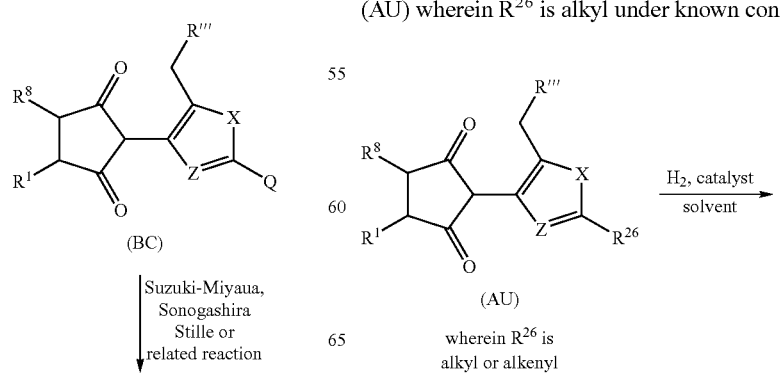

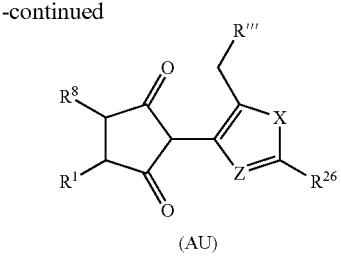

wherein $R^{26}$ is aryl, heteroaryl, alkenyl, alkynyl or similar

Those skilled in the art will appreciate that transformations of this type are not restricted to compounds of formula (BC), but may in general be applied to any compound of formula (I) where Het is a heterocycle substituted by an atom or group suitable for further derivatisation.

Those skilled in the art will appreciate that compounds of formula (AT) may contain a heteroaromatic moiety bearing one or more substituents capable of being transformed into alternative substituents under known conditions, and that these compounds may themselves serve as intermediates in the preparation of additional compounds of formula (AT). For example, a heterocycle of formula (AU) wherein $R^{26}$ is alkenyl or alkynyl, may be reduced to compounds of formula (AU) wherein $R^{26}$ is alkyl under known conditions.

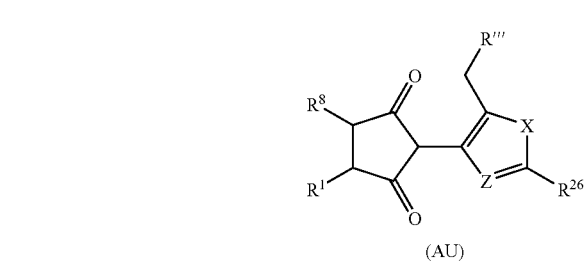

wherein R²⁶ is alkyl

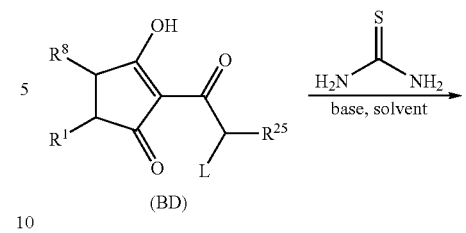

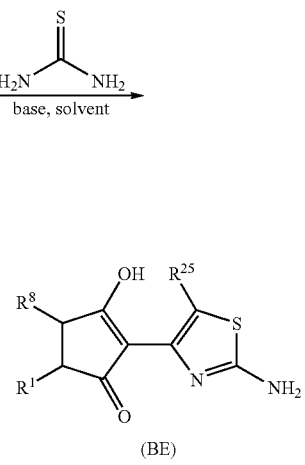

In a further approach to compounds of formula (AT), wherein Het is a group of formula (R₂), X is S, and Y is N, compounds of formula (BD) wherein L is a suitable leaving group such as a halogen or an alkyl- or haloalkylsulfonate, may be treated with compounds of formula (AJ) in the presence of a suitable base (such as triethylamine or pyridine), and optionally in a suitable solvent (such as water, acetone, ethanol or isopropanol) according to known procedures, (see, for example, E. Knott, J. Chem. Soc. (1945), 455; H. Brederick, R. Gompper, Chem. Ber. (1960), 93, 723; B. Friedman, M. Sparks and R. Adams, J. Am. Chem. Soc. (1937), 59, 2262).

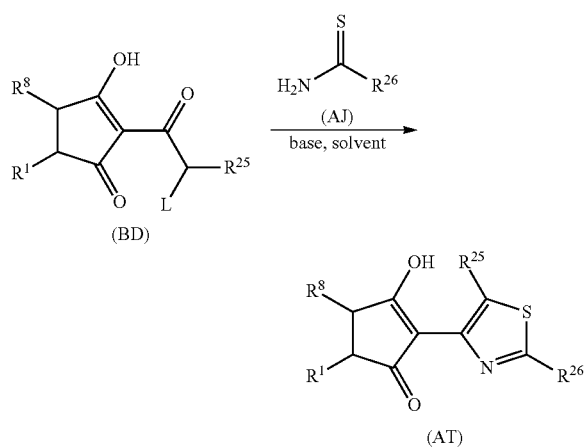

Compounds of formula (BD) may be prepared from compounds of formula (AY) under known conditions (see, for example, V. Pshenichniya, O. Gulyakevich and V. Kripach, Chemistry of Heterocyclic Compounds (1990), 10, 1409-1412; V. Pshenichniya, O. Gulyakevich and V. Kripach, Russian Journal of Organic Chemistry (1989), 25 (9), 1882-1888).

Furthermore, compounds of formula (I), wherein G is H and R³ and R⁶ form a bond, may be prepared by the reaction of compounds of formula (BG), with compounds of formula (H), optionally in the presence of a suitable solvent and a suitable catalyst.

Alternatively, compounds of formula (BD) may be treated with thiourea, by known procedures (see, for example, V. Pshenichniya, O. Gulyakevich and V. Kripach, Chemistry of Heterocyclic Compounds (1990), 10, 1409-1412), and the resulting products of formula (BE) may be converted into additional compounds of formula (AT) by conversion to halides of formula (BF), wherein Hal is chlorine, bromine or iodine, under Sandmeyer conditions, and compounds of formula (BF) may be converted to compounds of formula (AT) by cross-coupling under known conditions for the SuzukiMiyaura, Sonogashira, Stille and related reactions, as described previously.

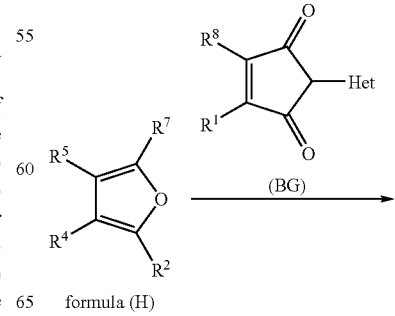

formula (H)

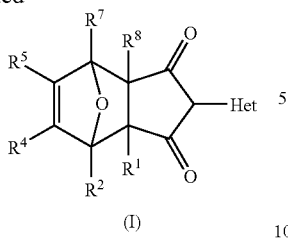

(I)

where G is Hydrogen
and $R^3$ and $R^6$ form a bond

Compounds of formula (BG), may be prepared by oxidising compounds of formula (BH) in a suitable solvent such as toluene, acetone, chloroform, dichloromethane or 1,4-dioxane. A wide range of oxidants are suitable for effecting this transformation, including inorganic oxidants such as chromium trioxide, pyridinium dichromate, manganese dioxide and aluminium alkoxides such as aluminium isopropoxide, as well as organic oxidants such as 2,3-dichloro-5,6-dicyano-p-benzoquinone and hypervalent iodine oxidants such as 1,1,1,-tris(acetyloxy)-1,1-dihydro-1,2-benziodoxol-3-(1H)-one (Dess-Martin periodinane), Suitable procedures are described, for example, in U.S. Pat. No. 4,371,711 and by G. Piancatelli et al. Tetrahedron (1978), 34(18), 2775-2778.

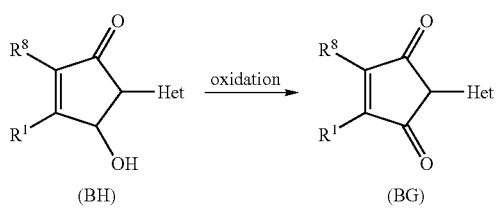

Compounds of formula (BH) may be prepared from compounds of formula (BJ) by treatment with a suitable acid catalyst in the presence of water and optionally in the presence of a suitable solvent, according to known procedures.

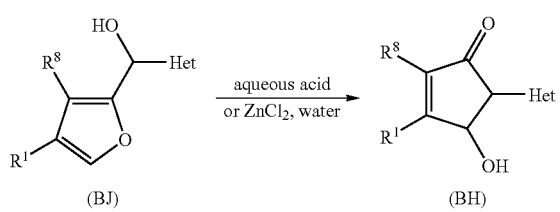

For example, compounds of formula (BJ) may be converted to compounds of formula (BH) in the presence of an aqueous solution of an acid such as polyphosphoric acid as described, for example in U.S. Pat. No. 4,371,711. Alternatively compounds of formula (BH) may be prepared from compounds of formula (BJ) by rearrangement in the presence of a Lewis acid catalyst such as zinc chloride according to the procedure of G. Piancatelli et al., Tetrahedron (1978), 34(18), 2775-2778.

Compounds of formula (BJ) may be prepared by the reduction of compounds of formula (BK) by known conditions (see, for example R Silvestri et al., J. Med. Chem. 2005, 48, 4378-4388; B-L Yin et al., Synthesis (2003), (13), 1995-2000).

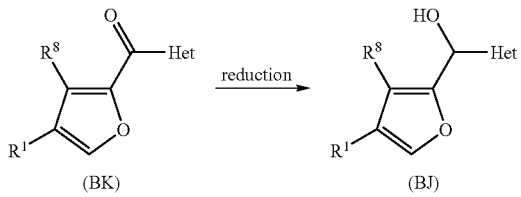

Compounds of formula (BK) are known, or may be made by known methods from known compounds (see, for example, Y. Shigetaka, T., Akira, Y. Katsumi, Yakugaku Zasshi (1968), 88(8), 997-1002; Leditschke, H. Arch. Pharm. (1952), 295, 323-30).

Alternatively compounds of formula (BJ) may be prepared by the addition of a suitable organometallic reagent such as a heteroarylmagnesium halide of formula (BL) wherein Hal is a halide such as chloride, bromide or iodide, or a heteroaryllithium reagent of formula (BM) or a diheteroarylzinc reagent of formula (BN) to a furan-2-carboxaldehyde of formula (BO) according to known procedures (see, for example G. Panda et al, Tetrahedron Lett., 46, 2005, 3097-3102; D. J. Dixon, M. S. Scott, C. A. Luckhurst, Synlett (2003), (15), 2317-2320; I. Gupta, M. Ravikanth, Tetrahedron (2003), 59(32), 6131-6139; M. Sanchez, O. Diallo, A. Oussaid, B. Oussaid, B. Garrigues, Phosphorus, Sulfur and Silicon and the Related Elements (2001), 173 235-242; B. Garrigues, M. Sanchez, O. Diallo, F. Chemat, Journal of Nature (2000), 12(1), 25-28; C. M. Shafer, T. F. Molinski, J. Org. Chem. (1998), 63(3), 551-555).

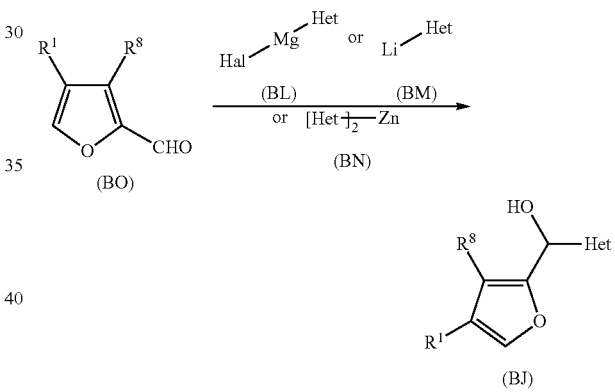

Additional compounds of formula (BJ) may be prepared from compounds of formula (BP) by reaction with an alkyl lithium reagent, such as n-butyllithium, optionally in the presence of an additive such as tetramethylethylenediamine, and in a suitable solvent such as diethyl ether or tetrahydrofuran, followed by reaction with a benzaldehyde of formula (BQ) as described, for example by I. Gupta and M. Ravikanth, J. Org. Chem., 2004, 69, 6796-6811, A. M. Echavarren et al., J. Am. Chem. Soc., 125 (19), 5757-5766, 2003 and by T. K. Chandrashekar et al., J. Org. Chem., 2002, 67, 6309-6319.

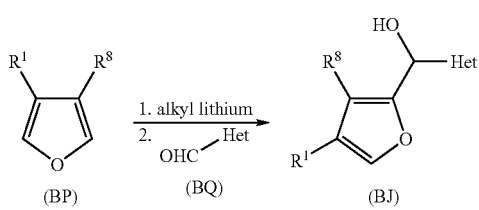

Compounds of formula (BP) and compounds of formula (BQ) are known compounds, or may be prepared from known compounds by known methods.

The compounds of formula (I) according to the invention can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifying, wetting or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides.

The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_5$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pene-trate®, can also be mixed into the spray mixture as activity-enhancing agents.

The herbicidal formulations generally contain from 0.1 to 99% by weight, especially from 0.1 to 95% by weight, of a compound of formula (I) and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula (I) may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula (I) according to the invention are generally applied at a rate of 1-2000 g/ha, preferably 1-1000 g/ha and most preferably at 1-500 g/ha.

Preferred formulations have especially the following compositions:
(%=percent by weight):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |

-continued

| F2. Solutions | a) | b) | c) | d) |
|---|---|---|---|---|
| NMP | — | — | 30% | 10% |
| arom. hydrocarbon mixture $C_9$-$C_{12}$ | 75% | 60% | — | — |

The solutions are suitable for application in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly disperse silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, and for non-selective weed control, which comprises treating the useful plants or the area under cultivation or the locus thereof with a compound of formula (I).

Crops of useful plants in which the compositions according to the invention can be used include especially cereals, in particular wheat and barley, rice, corn, rape, sugarbeet, sugarcane, soybean, cotton, sunflower, peanut and plantation crops.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*. Control of monocotyledonous weeds, in particular *Agrostis, Avena, Setaria, Lolium, Echinochloa, Bromus, Alopecurus* and *Sorghum* is very extensive.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by

*Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula (I) according to the invention can also be used in combination with other herbicides. The following mixtures of the compound of formula (I) are especially important. Preferably, in these mixtures, the compound of the formula (I) is one of those compounds listed in Tables 1 to 360 below:

compound of formula (I)+acetochlor, compound of formula (I)+acifluorfen, compound of formula (I)+acifluorfen-sodium, compound of formula (I)+aclonifen, compound of formula (I)+acrolein, compound of formula (I)+alachlor, compound of formula (I)+alloxydim, compound of formula (I)+allyl alcohol, compound of formula (I)+ametryn, compound of formula (I)+amicarbazone, compound of formula (I)+amidosulfuron, compound of formula (I)+aminopyralid, compound of formula (I)+amitrole, compound of formula (I)+ammonium sulfamate, compound of formula (I)+anilofos, compound of formula (I)+asulam, compound of formula (I)+atrazine, compound of formula (I)+aviglycine, compound of formula (I)+azafenidin, compound of formula (I)+azimsulfuron, compound of formula (I)+BCPC, compound of formula (I)+beflubutamid, compound of formula (I)+benazolin, compound of formula (I)+bencarbazone, compound of formula (I)+benfluralin, compound of formula (I)+benfuresate, compound of formula (I)+bensulfuron, compound of formula (I)+bensulfuron-methyl, compound of formula (I)+bensulide, compound of formula (I)+bentazone, compound of formula (I)+benzfendizone, compound of formula (I)+benzobicyclon, compound of formula (I)+benzofenap, compound of formula (I)+bifenox, compound of formula (I)+bilanafos, compound of formula (I)+bispyribac, compound of formula (I)+bispyribac-sodium, compound of formula (I)+borax, compound of formula (I)+bromacil, compound of formula (I)+bromobutide, compound of formula (I)+bromophenoxim, compound of formula (I)+bromoxynil, compound of formula (I)+butachlor, compound of formula (I)+butafenacil, compound of formula (I)+butamifos, compound of formula (I)+butralin, compound of formula (I)+butroxydim, compound of formula (I)+butylate, compound of formula (I)+cacodylic acid, compound of formula (I)+calcium chlorate, compound of formula (I)+cafenstrole, compound of formula (I)+carbetamide, compound of formula (I)+carfentrazone, compound of formula (I)+carfentrazone-ethyl, compound of formula (I)+CDEA, compound of formula (I)+CEPC, compound of formula (I)+chlorflurenol, compound of formula (I)+chlorflurenol-methyl, compound of formula (I)+chloridazon, compound of formula (I)+chlorimuron, compound of formula (I)+chlorimuron-ethyl, compound of formula (I)+chloroacetic acid, compound of formula (I)+chlorotoluron, compound of formula (I)+chlorpropham, compound of formula (I)+chlorsulfuron, compound of formula (I)+chlorthal, compound of formula (I)+chlorthal-dimethyl, compound of formula (I)+cinidon-ethyl, compound of formula (I)+cinmethylin, compound of formula (I)+cinosulfuron, compound of formula (I)+cisanilide, compound of formula (I)+clethodim, compound of formula (I)+clodinafop, compound of formula (I)+clodinafop-propargyl, compound of formula (I)+clomazone, compound of formula (I)+clomeprop, compound of formula (I)+clopyralid, compound of formula (I)+cloransulam, compound of formula (I)+cloransulam-methyl, compound of formula (I)+CMA, compound of formula (I)+4-CPB, compound of formula (I)+CPMF, compound of formula (I)+4-CPP, compound of formula (I)+CPPC, compound of formula (I)+cresol, compound of formula (I)+cumyluron, compound of formula (I)+cyanamide, compound of formula (I)+cyanazine, compound of formula (I)+cycloate, compound of formula (I)+cyclosulfamuron, compound of formula (I)+cycloxydim, compound of formula (I)+cyhalofop, compound of formula (I)+cyhalofop-butyl, compound of formula (I)+2,4-D, compound of formula (I)+3,4-DA, compound of formula (I)+daimuron, compound of formula (I)+dalapon, compound of formula (I)+dazomet, compound of formula (I)+2,4-DB, compound of formula (I)+3,4-DB, compound of formula (I)+2,4-DEB, compound of formula (I)+desmedipham, compound of formula (I)+desmetryn, compound of formula (I)+dicamba, compound of formula (I)+dichlobenil, compound of formula (I)+ortho-dichlorobenzene, compound of formula (I)+para-dichlorobenzene, compound of formula (I)+dichlorprop, compound of formula (I)+dichlorprop-P, compound of formula (I)+diclofop, compound of formula (I)+diclofop-methyl, compound of formula (I)+diclosulam, compound of formula (I)+difenzoquat, compound of formula (I)+difenzoquat metilsulfate, compound of formula (I)+diflufenican, compound of formula (I)+diflufenzopyr, compound of formula (I)+dimefuron, compound of formula (I)+dimepiperate, compound of formula (I)+dimethachlor, compound of formula (I)+dimethametryn, compound of formula (I)+dimethenamid, compound of formula (I)+dimethenamid-P, compound of formula (I)+dimethipin, compound of formula (I)+dimethylarsinic acid, compound of formula (I)+dinitramine, compound of formula (I)+dinoterb, compound of formula (I)+diphenamid, compound of formula (I)+dipropetryn, compound of formula (I)+diquat, compound of formula (I)+diquat dibromide, compound of formula (I)+dithiopyr, compound of formula (I)+diuron, compound of formula (I)+DNOC, compound of formula (I)+3,4-DP, compound of formula (I)+DSMA, compound of formula (I)+EBEP, compound of formula (I)+endothal, compound of formula (I)+EPTC, compound of formula (I)+esprocarb, compound of formula (I)+ethalfluralin, compound of formula (I)+ethametsulfuron, compound of formula (I)+ethametsulfuron-methyl, compound of formula (I)+ethephon, compound of formula (I)+ethofumesate, compound of formula (I)+ethoxyfen, compound of formula (I)+ethoxysulfuron, compound of formula (I)+etobenzanid, compound of formula (I)+fenoxaprop-P, compound of formula (I)+fenoxaprop-P-ethyl, compound of formula (I)+fentrazamide, compound of formula (I)+ferrous sulfate, compound of formula (I)+flamprop-M, compound of formula (I)+flazasulfuron, compound of formula (I)+florasulam, compound of formula (I)+fluazifop, compound of formula (I)+fluazifop-butyl, compound of formula (I)+fluazifop-P, compound of formula (I)+fluazifop-P-butyl, compound of formula (I)+fluazolate, compound of formula (I)+flucarbazone, compound of formula (I)+flucarbazone-sodium, compound of formula (I)+flucetosulfuron, compound of formula (I)+fluchloralin, compound of formula (I)+flufenacet, compound of formula (I)+flufenpyr, compound of formula (I)+flufenpyr-ethyl, compound of formula (I)+flumetralin, compound of formula (I)+flumetsulam, compound of formula (I)+flumiclorac, compound of formula (I)+flumiclorac-pentyl, compound of formula (I)+flumioxazin, compound of formula (I)+flumipropin, compound of formula (I)+fluometuron, compound of formula (I)+fluoroglycofen, compound of formula (I)+fluoroglycofen-ethyl, compound of formula (I)+fluoxaprop, compound of formula (I)+flupoxam, compound of formula (I)+flupropacil, compound of formula (I)+flupropanate, compound of formula (I)+flupyrsulfuron, compound of formula (I)+flupyrsulfuron-methyl-sodium, compound of formula (I)+flurenol, compound of formula (I)+fluridone, compound of formula (I)+fluorochloridone, compound of formula (I)+fluoroxypyr, compound of formula (I)+flurtamone, compound of formula (I)+fluthiacet, compound of formula (I)+fluthiacet-methyl, compound of formula (I)+fomesafen, compound of formula (I)+foramsulfuron, compound of formula (I)+fosamine, compound of formula (I)+glufosinate, compound of formula (I)+glufosinate-ammonium, compound of formula (I)+glyphosate, compound of formula (I)+halosulfuron, compound of formula (I)+halosulfuron-methyl, compound of formula (I)+haloxyfop, compound of formula (I)+haloxyfop-P, compound of formula (I)+HC-252, compound of formula (I)+hexazinone, compound of formula (I)+imazamethabenz, compound of formula (I)+imazamethabenz-methyl, compound of formula (I)+imazamox, compound of formula (I)+imazapic, compound of formula (I)+imazapyr, compound of formula (I)+imazaquin, compound of formula (I)+imazethapyr, compound of formula (I)+imazosulfuron, compound of formula (I)+indanofan, compound of formula (I)+iodomethane, compound of formula (I)+iodosulfuron, compound of formula (I)+iodosulfuron-methyl-sodium, compound of formula (I)+ioxynil, compound of formula (I)+isoproturon, compound of formula (I)+isouron, compound of formula (I)+isoxaben, compound of formula (I)+isoxachlortole, compound of formula (I)+isoxaflutole, compound of formula (I)+isoxapyrifop, compound of formula (I)+karbutilate, compound of formula (I)+lactofen, compound of formula (I)+lenacil, compound of formula (I)+linuron, compound of formula (I)+MAA, compound of formula (I)+MAMA, compound of formula (I)+MCPA, compound of formula (I)+MCPA-thioethyl, compound of formula (I)+MCPB, compound of formula (I)+mecoprop, compound of formula (I)+mecoprop-P, compound of formula (I)+mefenacet, compound of formula (I)+mefluidide, compound of formula (I)+mesosulfuron, compound of formula (I)+mesosulfuron-methyl, compound of formula (I)+mesotrione, compound of formula (I)+metam, compound of formula (I)+metamifop, compound of formula (I)+metamitron, compound of formula (I)+metazachlor, compound of formula (I)+methabenzthiazuron, compound of formula (I)+methazole, compound of formula (I)+methylarsonic acid, compound of formula (I)+methyldymron, compound of formula (I)+methyl isothiocyanate, compound of formula (I)+metobenzuron, compound of formula (I)+metobromuron, compound of formula (I)+metolachlor, compound of formula (I)+S-metolachlor, compound of formula (I)+metosulam, compound of formula (I)+metoxuron, compound of formula (I)+metribuzin, compound of formula (I)+metsulfuron, compound of formula (I)+metsulfuron-methyl, compound of formula (I)+MK-616, compound of formula (I)+molinate, compound of formula (I)+monolinuron, compound of formula (I)+MSMA, compound of formula (I)+naproanilide, compound of formula (I)+napropamide, compound of formula (I)+naptalam, compound of formula (I)+NDA-402989, compound of formula (I)+neburon, compound of formula (I)+nicosulfuron, compound of formula (I)+nipyraclofen, compound of formula (I)+n-methyl glyphosate, compound of formula (I)+nonanoic acid, compound of formula (I)+norflurazon, compound of formula (I)+oleic acid (fatty acids), compound of formula (I)+orbencarb, compound of formula (I)+orthosulfamuron, compound of formula (I)+oryzalin, compound of formula (I)+oxadiargyl, compound of formula (I)+oxadiazon, compound of formula (I)+oxasulfuron, compound of formula (I)+oxaziclomefone, compound of formula (I)+oxyfluorfen, compound of formula (I)+paraquat, compound of formula (I)+paraquat dichloride, compound of formula (I)+pebulate, compound of formula (I)+pendimethalin, compound of formula (I)+penoxsulam, compound of formula (I)+pentachlorophenol, compound of formula (I)+pentanochlor, compound of formula (I)+pentoxazone, compound of formula (I)+pethoxamid, compound of formula (I)+petrolium oils, compound of formula (I)+phenmedipham, compound of formula (I)+phenmedipham-ethyl, compound of formula (I)+picloram, compound of formula (I)+picolinafen, compound of formula (I)+pinoxaden, compound of formula (I)+piperophos, compound of formula (I)+potassium arsenite, compound of formula (I)+potassium azide, compound of formula (I)+pretilachlor, compound of formula (I)+primisulfuron, compound of formula (I)+primisulfuron-methyl, compound of formula (I)+prodiamine, compound of formula (I)+profluazol, compound of formula (I)+profoxydim, compound of formula (I)+prohexadione-calcium, compound of formula (I)+prometon, compound of formula (I)+prometryn, compound of formula (I)+propachlor, compound of formula (I)+propanil, compound of formula (I)+propaquizafop, compound of formula (I)+propazine, compound of formula (I)+propham, compound of formula (I)+propisochlor, compound of formula (I)+propoxycarbazone, compound of formula (I)+propoxycarbazone-sodium, compound of formula (I)+propyzamide, compound of formula (I)+prosulfocarb, compound of formula (I)+prosulfuron, compound of formula (I)+pyraclonil, compound of formula (I)+pyraflufen, compound of formula (I)+pyraflufen-ethyl, compound of formula (I)+pyrasulfotole, compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyributicarb, compound of formula (I)+pyridafol, compound of formula (I)+pyridate, compound of formula (I)+pyriftalid, compound of formula (I)+pyriminobac, compound of formula (I)+pyriminobac-methyl, compound of formula (I)+pyrimisulfan, compound of formula (I)+pyrithiobac, compound of formula (I)+pyrithiobac-sodium, compound of formula (I)+pyroxasulfone (KIN-485), compound of formula (I)+pyroxulam, compound of formula (I)+quinclorac, compound of formula (I)+quinmerac, compound of formula (I)+quinoclamine, compound of formula (I)+quizalofop, compound of formula (I)+quizalofop-P, compound of formula (I)+rimsulfuron, compound of formula (I)+sethoxydim, compound of formula (I)+siduron, compound of formula (I)+simazine, compound of formula (I)+simetryn, compound of formula (I)+SMA, compound of formula (I)+sodium arsenite, compound of formula (I)+sodium azide, compound of formula (I)+sodium chlorate, compound of formula (I)+sulcotrione, compound of formula (I)+sulfentrazone, compound of formula (I)+sulfometuron, compound of formula (I)+sulfometuron-methyl, compound of formula (I)+sulfosate, compound of formula (I)+sulfosulfuron, compound of formula (I)+sulfuric acid, compound of formula (I)+tar oils, compound of formula (I)+2,3,6-TBA, compound of formula (I)+TCA, compound of formula (I)+TCA-sodium, compound of formula (I)+tebutam, compound of formula (I)+tebuthiuron, compound of formula (I)+tefuryltrione, compound of formula 1+tembotrione, compound of formula (I)+tepraloxydim, compound of formula (I)+terbacil, compound of formula (I)+terbumeton, compound of formula (I)+terbuthylazine, compound of formula (I)+terbutryn, compound of formula (I)+thenylchlor, compound of formula (I)+thiazafluoron, compound of formula (I)+thiazopyr, compound of formula (I)+thifensulfuron, compound of formula (I)+thiencarbazone, compound of formula (I)+thifensulfuron-methyl, compound of formula (I)+thiobencarb, compound of formula (I)+tiocarbazil, compound of formula (I)+topramezone, compound of formula (I)+tralkoxydim, compound of formula (I)+tri-allate, compound of formula (I)+triasulfuron, compound of formula (I)+triaziflam, compound of formula (I)+tribenuron, compound of formula (I)+tribenuron-methyl, compound of formula (I)+tricamba, compound of formula (I)+triclopyr, compound of formula (I)+trietazine, compound of formula (I)+trifloxysulfuron, compound of formula (I)+trifloxysulfuron-sodium, compound of formula (I)+trifluralin, compound of formula (I)+triflusulfuron, compound of formula (I)+triflusulfuron-methyl, compound of formula (I)+trihydroxytriazine, compound of formula (I)+trinexapac-ethyl, compound of formula (I)+tritosulfuron, compound of formula (I)+[3-[2-chloro-4-fluoro-5-(1-methyl-6-trifluoromethyl-2,4-dioxo-1,2,3,4-tetrahydropyrimidin-3-yl)phenoxy]-2-pyridyloxy] acetic acid ethyl ester (CAS RN 353292-31-6), compound of formula (I)+4-hydroxy-3-[[2-[(2-methoxyethoxy)methyl]-6-(trifluoro-methyl)-3-pyridinyl]carbonyl]-bicyclo[3.2.1] oct-3-en-2-one (CAS RN 352010-68-5), and compound of formula (I)+4-hydroxy-3-[[2-(3-methoxypropyl)-6-(difluoromethyl)-3-pyridinyl]carbonyl]-bicyclo[3.2.1]oct-3-en-2-one.

The mixing partners for the compound of formula (I) may also be in the form of esters or salts, as mentioned e.g. in The Pesticide Manual, 12th Edition (BCPC) 2000.

The compounds of formula (I) according to the invention can also be used in combination with safeners. Preferably, in these mixtures, the compound of the formula (I) is one of those compounds listed in Tables 1 to 360 below. The following mixtures with safeners, especially, come into consideration:
compound of formula (I)+cloquintocet-mexyl, compound of formula (I)+cloquintocet acid and salts thereof, compound of formula (I)+fenchlorazole-ethyl, compound of formula (I)+fenchlorazole acid and salts thereof, compound of formula (I)+mefenpyr-diethyl, compound of formula (I)+mefenpyr diacid, compound of formula (I)+isoxadifen-ethyl, compound of formula (I)+isoxadifen acid, compound of formula (I)+furilazole, compound of formula (I)+furilazole R isomer, compound of formula (I)+benoxacor, compound of formula (I)+dichlormid, compound of formula (I)+AD-67, compound of formula (I)+oxabetrinil, compound of formula (I)+cyometrinil, compound of formula (I)+cyometrinil Z-isomer, compound of formula (I)+fenclorim, compound of formula (I)+cyprosulfamide, compound of formula (I)+naphthalic anhydride, compound of formula (I)+flurazole, compound of formula (I)+CL 304,415, compound of formula (I)+dicyclonon, compound of formula (I)+fluxofenim, compound of formula (I)+DKA-24, compound of formula (I)+R-29148 and compound of formula (I)+PPG-1292. A safening effect can also be observed for the mixtures compound of the formula (I)+dymron, compound of the formula (I)+MCPA, compound of the formula (I)+mecopropand compound of the formula (I)+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein and PPG-1292 is known from WO09211761.

The rate of application of safener relative to the herbicide is largely dependent upon the mode of application. In the case of field treatment, generally from 0.001 to 5.0 kg of safener/ha, preferably from 0.001 to 0.5 kg of safener/ha, and generally from 0.001 to 2 kg of herbicide/ha, but preferably from 0.005 to 1 kg/ha, are applied.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

The following Examples illustrate the invention further but do not limit the invention.

PREPARATION EXAMPLES

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds are shown in Table T1 as a single enol tautomer, but it should be inferred that this description covers both the diketone form and any possible enols which could arise through tautomerism. Furthermore, some of the compounds in Table T1 and Table P1 are drawn as single enantiomers for the purposes of simplicity, but unless specified as single enantiomers these structures should be construed as representing a mixture of enantiomers. Within the detailed experimental section the diketone tautomer is chosen for naming purposes, even if the predominant tautomer is the enol form.

Where more than one tautomer observed in proton NMR, the data shown are for the mixture of tautomers.

Example 1

Preparation of 4-[2-(4-chloro-phenyl)-5-methyl-selenazol-4-yl]-10-oxa-tricyclo[5.2.1.0*2,6*]decane-3,5-dione

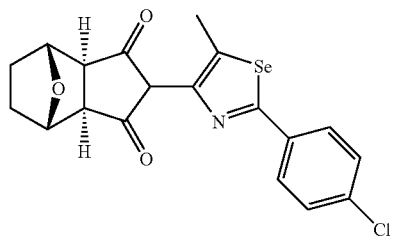 [SMILES: Cc1[se]c(-c2ccc(Cl)cc2)nc1C1C(=O)[C@@H]2[C@H](C1=O)[C@H]1CC[C@@H]2O1]

Step 1

Preparation of 5-chloro-10-oxa-tricyclo[5.2.1.0*2,6*]dec-4-en-3-one

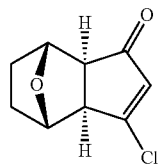 [SMILES: O=C1C=C(Cl)[C@@H]2[C@H]1[C@H]1CC[C@@H]2O1]

To a solution of 10-oxa-tricyclo[5.2.1.0*2,6*]decane-3,5-dione (1.66 g, 10 mmol) in chloroform (20 ml) is added PCl$_5$ (1.04 g, 5 mmol) in one portion. The reaction mixture is stirred and heated at reflux for 5 hours. The reaction mixture is evaporated to dryness. The crude product is purified by flash chromatography to give 5-chloro-10-oxa-tricyclo[5.2.1.0*2,6*]dec-4-en-3-one (1.29 g).

Step 2

Preparation of 2-(4-chlorophenyl)selenazole-5-carbaldehyde

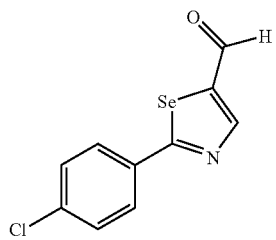 [SMILES: O=Cc1cnc(-c2ccc(Cl)cc2)[se]1]

To a suspension of 4-chloroselenobenzamide (219 mg, 1 mmol) and 2-chloromalonaldehyde (160 mg, 1.5 mmol) in 1,2-dimethoxyethane (1.5 ml) is added magnesium carbonate (42 mg, 0.5 mmol) and the resulting mixture is stirred at 60° C. under an atmosphere of nitrogen for 3 hours. The crude reaction mixture is then filtered through a plug of silica and washed with ethyl acetate, and the filtrate is concentrated to give a brown solid. The crude product is purified by flash chromatography on silica gel to give 2-(4-chlorophenyl)selenazole-5-carbaldehyde (162 mg).

Step 3

Preparation of [2-(4-chlorophenyl)selenazol-5-yl]methanol

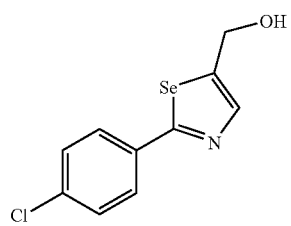 [SMILES: OCc1cnc(-c2ccc(Cl)cc2)[se]1]

To a suspension of 2-(4-chlorophenyl)selenazole-5-carbaldehyde (130 mg, 0.48 mmol) in methanol (5 ml) is added sodium borohydride (19 mg, 0.5 mmol) at 0° C. The reaction mixture is stirred at 0° C. for 0.5 hour. The reaction mixture is quenched with saturated aqueous ammonium chloride solution (10 ml), and extracted with dichloromethane (3×25 ml). The combined organic extracts are dried over anhydrous magnesium sulfate, filtered and the filtrate is evaporated to dryness to give [2-(4-chlorophenyl)selenazol-5-yl]methanol (127 mg).

Step 4

Preparation of 5-[2-(4-chloro-phenyl)-selenazol-5-ylmethoxy]-10-oxa-tricyclo[5.2.1.0*2,6*]dec-4-en-3-one

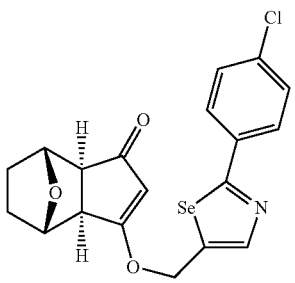 [SMILES: O=C1C=C(OCc2cnc(-c3ccc(Cl)cc3)[se]2)[C@@H]2[C@H]1[C@H]1CC[C@@H]2O1]

To a solution of [2-(4-chlorophenyl)selenazol-5-yl]methanol (300 mg, 1.1 mmol) in dry tetrahydrofuran (5 ml) is added, in one portion, sodium hydride (60% dispersion in mineral oil, 44 mg, 1.1 mmol). The reaction mixture is stirred for 5 minutes at room temperature and 5-chloro-10-oxa-tricyclo[5.2.1.0*2,6*]dec-4-en-3-one (203 mg, 1.1 mmol) is added in one-portion. The reaction mixture is stirred at room temperature overnight. Silica gel is added to the crude reaction mixture, the solvent is evaporated under reduced pressure and the residue is purified by flash chromatography on silica gel to give 5-[2-(4-chloro-phenyl)-selenazol-5-ylmethoxy]-10-oxa-tricyclo[5.2.1.0*2,6*]dec-4-en-3-one (360 mg).

Step 5

Preparation of 4-[2-(4-chloro-phenyl)-5-methyl-selenazol-4-yl]-10-oxa-tricyclo[5.2.1.0*2,6*]decane-3,5-dione

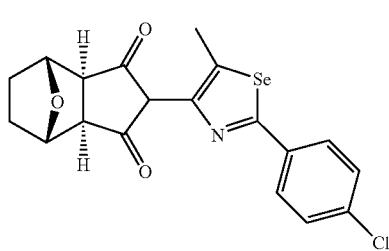 [SMILES: Cc1[se]c(-c2ccc(Cl)cc2)nc1C1C(=O)[C@@H]2[C@H](C1=O)[C@H]1CC[C@@H]2O1]

5-[2-(4-chloro-phenyl)-selenazol-5-ylmethoxy]-10-oxa-tricyclo[5.2.1.0*2,6*]dec-4-en-3-one (233 mg, 0.55 mmol) is placed in a microwave vial and dissolved in diethylene glycol dimethyl ether (8 ml). 1-Butyl-3-methylimidazolium bis(trifluoromethylsulfonyl)imide (0.1 ml) is added and the reaction mixture is heated at 210° C. for 30 minutes under microwave irradiation. Silica gel is added to the crude reaction mixture, the solvent is evaporated under reduced pressure and the residue is purified by flash chromatography on silica gel to give 4-[2-(4-chloro-phenyl)-5-methyl-selenazol-4-yl]-10-oxa-tricyclo[5.2.1.0*2,6*]decane-3,5-dione (146 mg).

Example 2

Preparation of 4-[2-(4-chloro-phenyl)-5-ethyl-thiazol-4-yl]-1'-1-methyl-10-oxa-tricyclo[5.2.1.0*2,6*]decane-3,5-dione

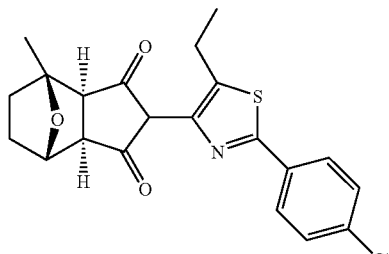

Step 1

Preparation of 1-methyl-10-oxa-tricyclo[5.2.1.0*2,6*]dec-8-ene-3,5-dione

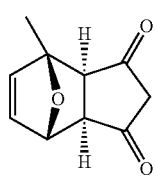

A mixture of 4-cyclopentene-1,3-dione (10 g, 104 mmol) and 2-methylfuran (15 ml) are stirred at room temperature for 3 days. Methanol (50 ml) is then added and the solid is collected and dried on a Buchner funnel to give 1-methyl-10-oxa-tricyclo[5.2.1.0*2,6*]dec-8-ene-3,5-dione (14.3 g)

Step 2

Preparation of 1-methyl-10-oxa-tricyclo[5.2.1.0*2,6*]decane-3,5-dione

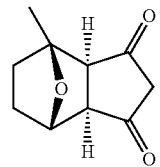

The 10-oxa-tricyclo[5.2.1.0*2,6*]dec-8-ene-3,5-dione (10.5 g) is dissolved in methanol (700 ml). The methanol solution is passed at a rate of 1.5 ml/min through a Thalis H-cube apparatus (from Thalis nanotec) set-up at 40° C. and 40 bar and fitted with a 10% Pd/C cartridge. The so obtained solution is evaporated to give 1-methyl-10-oxa-tricyclo[5.2.1.0*2,6*]decane-3,5-dione (9.2 g).

Step 3

Preparation of 5-chloro-1-methyl-10-oxa-tricyclo[5.2.1.0*2,6*]dec-4-en-3-one

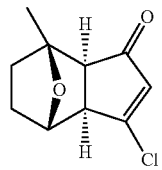

To a solution of 1-methyl-10-oxa-tricyclo[5.2.1.0*2,6*]decane-3,5-dione (3 g, 16.6 mmol) in chloroform (8 ml) is added $PCl_5$ portionwise. The reaction mixture is stirred and heated at reflux for 5 hours. The reaction mixture is evaporated to dryness The crude product is purified by flash chromatography on silica gel to give 5-chloro-1-methyl-10-oxa-tricyclo[5.2.1.0*2,6*]dec-4-en-3-one (1.39 g).

Step 4

Preparation of 1-[2-(4-chloro-phenyl)-thiazol-5-yl]ethanol

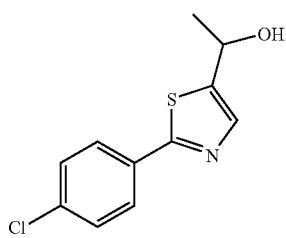

To a suspension of 1-[2-(4-chloro-phenyl)-thiazol-5-yl]ethanone (5 g, 21 mmol) in methanol (100 ml) is added sodium borohydride (832 mg, 22 mmol) at room temperature. The reaction mixture is stirred at room temperature for 0.5 hour. The reaction mixture is quenched with 100 ml of an aqueous saturated solution of ammonium chloride, extracted with dichloromethane (2×150 ml). The combined organic extracts are dried over magnesium sulphate, filtered and evaporated to dryness to give 1-[2-(4-chloro-phenyl)-thiazol-5-yl]ethanol (4.88 g).

Step 5

Preparation of 5-[2-(4-chloro-phenyl)-thiazol-5-yl-methoxy]-1-methyl-10-oxa-tricyclo[5.2.1.0*2,6*]dec-4-en-3-one

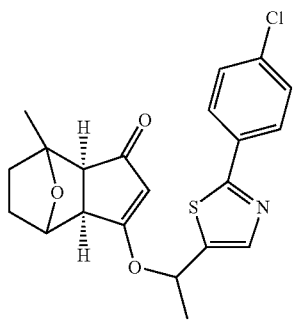 [SMILES: CC(OC1=CC(=O)[C@H]2[C@@H]1C1CCC2(C)O1)c1cnc(-c2ccc(Cl)cc2)s1]

To a solution of 1-[2-(4-chloro-phenyl)-thiazol-5-yl]ethanol (264 mg, 1.1 mmol) in tetrahydrofuran (5 ml) is added in one portion the sodium hydride (60% dispersion in mineral oil, 44 mg, 1.1 mmol). The reaction mixture is stirred for five minutes at room temperature and 5-Chloro-1-methyl-10-oxa-tricyclo[5.2.1.0*2,6*]dec-4-en-3-one (219 mg, 1.1 mmol) is added in one-portion. The reaction mixture is stirred at room temperature overnight. Silica gel is added to the crude reaction mixture, the solvent is evaporated under reduced pressure and the residue is purified by flash chromatography on silica gel to give 5-[2-(4-chloro-phenyl)-thiazol-5-ylmethoxy]-1-methyl-10-oxa-tricyclo[5.2.1.0*2,6*]dec-4-en-3-one (410 mg).

Step 6

Preparation of 4-[2-(4-chloro-phenyl)-5-ethyl-thiazol-4-yl]-methyl-10-oxa-tricyclo[5.2.1.0*2,6*]decane-3,5-dione

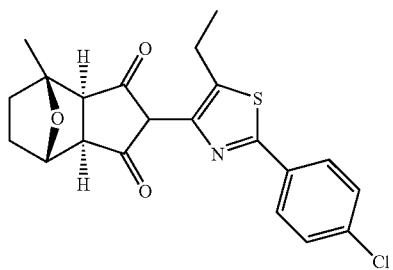 [SMILES: CCc1sc(-c2ccc(Cl)cc2)nc1C1C(=O)[C@H]2[C@@H]3CC[C@@](C)(O3)[C@H]2C1=O]

5-[2-(4-chloro-phenyl)-thiazol-5-ylmethoxy]-1-methyl-10-oxa-tricyclo[5.2.1.0*2,6*]dec-4-en-3-one (410 mg, 0.56 mmol) is placed in a microwave vial and dissolved in diethylene glycol dimethyl ether (8 ml). 1-Butyl-3-methylimidazolium bis(trifluoromethylsulfonyl)imide (0.1 ml) is added and the reaction mixture is heated at 210° C. for 30 minutes under microwave irradiation. Silica gel is added to the crude reaction mixture, the solvent is evaporated under reduced pressure and the residue is purified by flash chromatography on silica gel to give 4-[2-(4-chloro-phenyl)-5-ethyl-thiazol-4-yl]-1-methyl-10-oxa-tricyclo[5.2.1.0*2,6*]decane-3,5-dione (175 mg).

Example 3

Preparation of 5-{1-[2-(4-Bromo-2-methyl-phenyl)-thiazol-5-yl]-ethoxy}-10-oxa-tricyclo[5.2.1.0*2,6*]dec-4-en-3-one

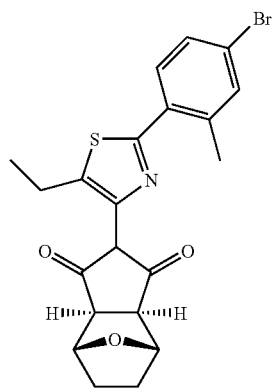 [SMILES: CCc1sc(-c2ccc(Br)cc2C)nc1C1C(=O)[C@@H]2[C@H](C1=O)[C@H]1CC[C@@H]2O1]

Step 1

Preparation of 4-bromo-2-methyl-thiobenzamide

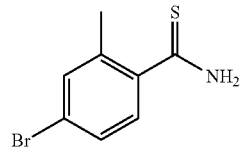

To a slurry solution of sodium hydrosulphide (2.80 g, 50 mmol) and magnesium chloride hexahydrate (5.05 g, 25 mmol) in dimethylformamide (50 ml) is added 4-bromo-2-methyl benzonitrile (4.90 g, 50 mmol) in one portion and the resulting green slurry is stirred at room temp for 90 minutes. The reaction mixture is poured onto water (200 ml) and the resultant precipitate filtered and washed with water. This yellow solid is then suspended in 2N HCl (200 ml) and stirred for 1 hour, then filtered, washed with water and hexane and dried in vacuo to give 4-bromo-2-methyl-thiobenzamide (820 mg).

Step 2

Preparation of 2-(4-bromo-2-methyl-phenyl)-thiazole-5-carbaldehyde

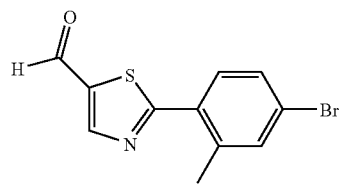

To a suspension of 4-bromo-2-methyl-thiobenzamide (3.11 g, 13.5 mmol) and 2-chloromalonaldehyde (2.16 g, 20.3 mmol) in dimethoxyethane (20 ml) is added magnesium carbonate (567 mg, 6.75 mmol) and the resulting mixture stirred at 60° C. under $N_2$ for 3 hours. The crude reaction is then filtered through a plug of silica, washed with EtOAc and the filtrate concentrated to give 2-(4-bromo-2-methyl-phenyl)-thiazole-5-carbaldehyde (3.8 g).

Step 3

Preparation of 1-[2-(4-bromo-2-methyl-phenyl)-thiazol-5-yl]-ethanol

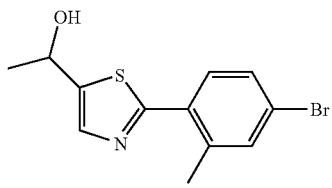 [SMILES: Cc1cc(Br)ccc1-c1ncc(C(C)O)s1]

A suspension of 2-(4-bromo-2-methyl-phenyl)-thiazole-5-carbaldehyde (1.9 g, 6.7 mmol) in ether at 0° C. is treated with 3.0 M MeMgBr (5 ml, 15 mmol) in diethyl ether (50 ml). The reaction mixture is stirred for 2 hours then carefully diluted with water. Acidified with aq. sat. $NH_4Cl$. The aqueous layer is extracted with DCM (2×100 ml). The combined organic layers are dried over magnesium sulphate, filtered and evaporated to dryness to give 1.80 g of crude product. The crude product is purified by flash chromatography on silica gel to give 1-[2-(4-bromo-2-methyl-phenyl)-thiazol-5-yl]-ethanol (1.40 g).

Step 4

Preparation of 5-{1-[2-(4-bromo-2-methyl-phenyl)-thiazol-5-yl]-ethoxy}-10-oxa-tricyclol[5.2.1.0*2,6*]dec-4-en-3-one

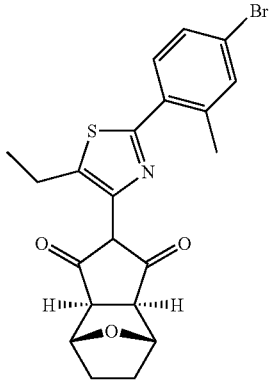 [SMILES: CCc1sc(-c2ccc(Br)cc2C)nc1C1C(=O)[C@@H]2[C@H](C1=O)[C@H]1CC[C@@H]2O1]

To a solution of [2-(4-bromo-2-methyl-phenyl)-thiazol-5-yl]-ethanol (450 mg, 1.5 mmol) and 5-chloro-10-oxa-tricyclo[5.2.1.0*2,6*]dec-4-en-3-one (277 mg, 1.5 mmol) in tetrahydrofuran (10 ml) is added in one portion the sodium hydride (60% dispersion in mineral oil, 60 mg, 1.5 mmol). The reaction mixture is stirred at room temperature for 24 hours. The crude reaction mixture is vacced down under reduced pressure and 10 ml of triglyme are added. The reaction mixture is therefore heated to reflux for 30 minutes. The crude reaction mixture is vacced down and purified by flash chromatography on silica gel to give a yellow solid. The solid is washed with iso-hexane to give 5-{1-[2-(4-bromo-2-methyl-phenyl)-thiazol-5-yl]-ethoxy}-10-oxa-tricyclo[5.2.1.0*2,6*]dec-4-en-3-one (490 mg).

Example 4

Preparation of 4-[5-(4-chloro-phenyl)-2-ethyl-thiophen-3-yl]-10-oxa-tricyclo[5.2.1.0*2,6*]decane-3,5-dione

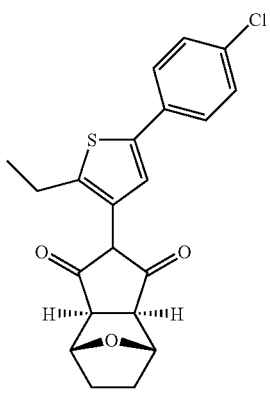 [SMILES: CCc1sc(-c2ccc(Cl)cc2)cc1C1C(=O)[C@@H]2[C@H](C1=O)[C@H]1CC[C@@H]2O1]

Step 1

Preparation of 3-bromo-5-(4-chloro-phenyl)-2-ethyl-thiophene

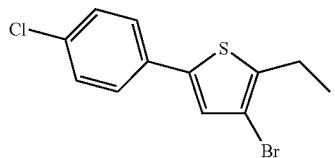

To a solution of 3,5-dibromo-2-ethyl-thiophene (3.28 g, 12.15 mmol) in diethyl ether (50 ml) at −78° C. under $N_2$ is added, slowly, 2.5M butyl lithium in hexane solution (4.86 ml, 12.15 mmol) over 10 minutes and the reaction stirred at −78° C. for a further 30 minutes. The reaction is then cooled to −78° C. before the dropwise addition of trimethyl borate (1.64 ml, 14.6 mmol) over 5 minutes. The reaction is stirred at −78° C. for 30 minutes, then allowed to warm to room temperature and stirred for a further 60 minutes. Palladium acetate (68 mg, 0.3 mmol), triphenylphosphine (314 mg, 1.2 mmol) and 4-chloro-iodobenzene (4.9 g, 12.15 mmol) is then added to the reaction, followed by THF (50 ml) and 1N sodium carbonate solution (20 ml) and the reaction is heated to reflux for 3 hours. The cooled reaction mixture is partitioned between ether (250 ml) and water (300 ml). The organic layer is separated, dried over magnesium sulphate, filtered and evaporated under reduced pressure. The residue is therefore purified by flash chromatography on silica gel to give 3-bromo-5-(4-chlorophenyl)-2-ethyl-thiophene as a white solid (2.75 g).

Step 2

Preparation of [5-(4-chloro-phenyl)-2-ethyl-thiophen-3-yl]furan-2-yl-methanol

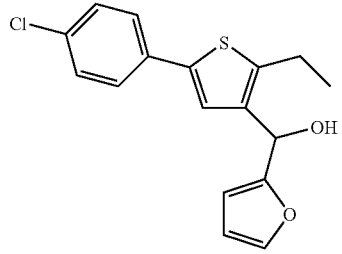 [SMILES: CCc1sc(-c2ccc(Cl)cc2)cc1C(O)c1ccco1]

To a solution of 3-bromo-5-(4-chlorophenyl)-2-ethyl-thiophene (2.62 g, 8.67 mmol) in diethyl ether (30 ml) at −78° C. under $N_2$ is added, slowly, 2.5M butyl lithium in hexane solution (4.86 ml, 12.15 mmol) over 10 minutes and the reaction stirred at −78° C. for a further 30 minutes. 2-Fufuraldehyde (1 ml, 12.14 mmol) is then added dropwise over a period of 5 minutes, and the reaction is allowed to stir at −78° C. for 15 minutes before being allowed to warm to room temperature and stirred for 1 hour. Reaction is quenched with aqueous saturated ammonium chloride (100 ml) and extracted with ether (100 ml). The organic layer separated is dried over magnesium sulphate, filtered and evaporated to dryness. The residue is therefore purified by flash chromatography on silica gel to give [5-(4-chloro-phenyl)-2-ethyl-thiophen-3-yl]furan-2-yl-methanol as a yellow oil (2.52 g).

Step 3

Preparation of 5-[5-(4-chloro-phenyl)-2-ethyl-thiophen-3-yl]-4-hydroxy-cyclopent-2-enone

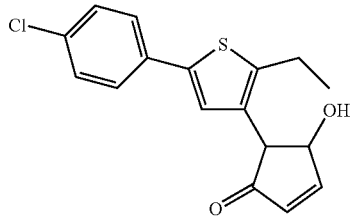 [SMILES: CCc1sc(-c2ccc(Cl)cc2)cc1C1C(=O)C=CC1O]

To a solution of [5-(4-chloro-phenyl)-2-ethyl-thiophen-3-yl]-furan-2-yl-methanol (2.52 g, 7.9 mmol) in acetone (30 ml) and water (5 ml) is added polyphosphoric acid (0.5 ml) and the resulting solution heated at 60° C. for 5 hours. The resulting black solution is concentrated in vacuo and purified by flash chromatography on silica gel to give 5-[5-(4-chloro-phenyl)-2-ethyl-thiophen-3-yl]-4-hydroxy-cyclopent-2-enone as a clear gum (320 mg)

Step 4

Preparation of 2-[5-(4-chloro-phenyl)-2-ethyl-thiophen-3-yl]-cyclopent-4-ene-1,3-dione

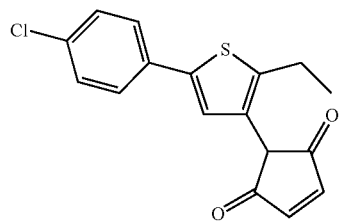 [SMILES: CCc1sc(-c2ccc(Cl)cc2)cc1C1C(=O)C=CC1=O]

To a solution of 5-[5-(4-chloro-phenyl)-2-ethyl-thiophen-3-yl]-4-hydroxy-cyclopent-2-enone (300 mg, 0.95 mmol) in acetone (5 ml) at 0° C. is added, dropwise, Jones' reagent and the resulting yellow solution stirred at 0° C. for 80 minutes. Reaction is quenched by the addition of propan-2-ol (1 ml) and stirred for a further 2 hours. Brine (50 ml) is added and the reaction is extracted with ethyl acetate (2×50 ml). The combined organics are then washed with brine, dried over magnesium sulphate and concentrated in vacuo to give 2-[5-(4-chloro-phenyl)-2-ethyl-thiophen-3-yl]-cyclopent-4-ene-1,3-dione as an orange solid (248 mg).

Step 5

Preparation of 4-[5-(4-chloro-phenyl)-2-ethyl-thiophen-3-yl]-10-oxa-tricyclo[5.2.1.0*2,6*]dec-8-ene-3,5-dione

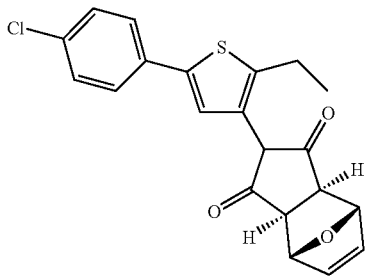 [SMILES: CCc1sc(-c2ccc(Cl)cc2)cc1C1C(=O)[C@@H]2[C@H](C1=O)[C@H]1C=C[C@@H]2O1]

To a stirred solution of 2-[5-(4-chloro-phenyl)-2-ethyl-thiophen-3-yl]-cyclopent-4-ene-1,3-dione (248 mg, 0.78 mmol) in furan (3 ml) is added magnesium iodide (44 mg, 0.15 mmol) and the reaction allowed to stir at room temperature for 4 days. The crude reaction mixture is purified by flash chromatography to give 4-[5-(4-chloro-phenyl)-2-ethyl-thiophen-3-yl]-10-oxa-tricyclo[5.2.1.0*2,6*]dec-8-ene-3,5-dione as a white solid (180 mg).

Step 6

Preparation of 4-[5-(4-chloro-phenyl)-2-ethyl-thiophen-3-yl]-10-oxa-tricyclo[5.2.1.0*2,6*]decane-3,5-dione

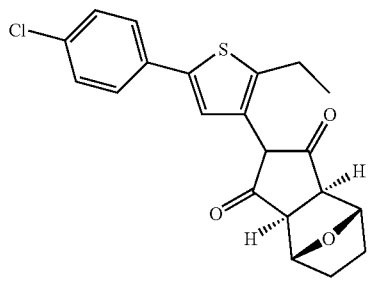 [SMILES: CCc1sc(-c2ccc(Cl)cc2)cc1C1C(=O)[C@@H]2[C@H](C1=O)[C@H]1CC[C@@H]2O1]

A solution of 4-[5-(4-chloro-phenyl)-2-ethyl-thiophen-3-yl]-10-oxa-tricyclo[5.2.1.0*2,6*]dec-8-ene-3,5-dione (180 mg, 0.47 mmol) in methanol (5 ml) is stirred under hydrogen (3 bars) for 7 hours. The reaction solution is filtered through a Celite pad and the filtrate concentrated to give 4-[5-(4-chloro-phenyl)-2-ethyl-thiophen-3-yl]-10-oxa-tricyclo[5.2.1.0*2,6*]decane-3,5-dione (51 mg).

Example 5

Preparation of 4-(5-bromo-4-ethyl-2-methyl-thiophen-3-yl)-10-oxa-tricyclo[5.2.1.0*2,6*]decane-3,5-dione

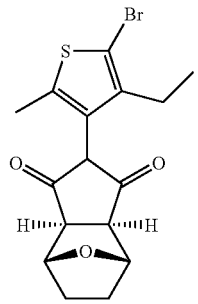 [SMILES: CCc1c(Br)sc(C)c1C1C(=O)[C@@H]2[C@H](C1=O)[C@H]1CC[C@@H]2O1]

Step 1

Preparation of 4-ethyl-thiophene-2-carbaldehyde

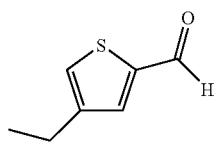

To a solution of 3-ethylthiophene (2 g, 17.7 mmol) in ether (20 ml) under $N_2$ at room temp is added butyl lithium, 2.5M in hexane solution (8.15 ml, 21.4 mmol) and the resulting straw coloured solution is heated to reflux for 20 minutes. The resulting cloudy solution is then cooled to room temperature before the slow addition of DMF (2 ml) over 2 minutes and the resulting solution is stirred at room temp for 1 hour. The reaction is quenched with aqueous saturated ammonium chloride (100 ml) and extracted with chloroform (100 ml). The organic layer is washed with brine, dried over magnesium sulphate and concentrated to give 4-ethyl thiophene-2-carbaldehyde as a light brown oil (2.48 g).

Step 2

Preparation of (4-ethyl-thiophen-2-yl)methanol

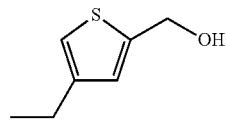

To a stirred solution of 4-ethyl thiophene-2-carbaldehyde (2.48 g, 17.7 mmol) in methanol (10 ml) at 0° C. is added sodium borohydride (707 mg, 18.7 mmol) in one portion. The resultant solution is allowed to warm to ambient and stirred at room temperature for 40 minutes. Reaction is concentrated in vacuo, quenched with saturated aqueous ammonium chloride solution (100 ml) and extracted with chloroform (100 ml). The organics are dried over magnesium sulphate, filtered and concentrated to give a light brown oil, which is purified by flash chromatography on silica gel to give (4-ethyl-thiophen-2-yl)methanol as a clear oil (1.87 g).

Step 3

Preparation of 5-(4-ethyl-thiophen-2-ylmethoxy)-10-oxa-tricyclo[5.2.1.0*2,6*]dec-4-en-3-one

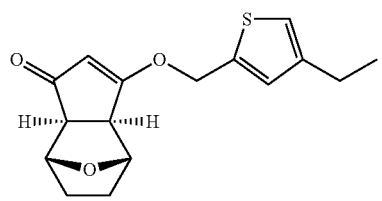 [SMILES: CCc1csc(COC2=CC(=O)[C@H]3[C@@H]2[C@@H]2CC[C@H]3O2)c1]

To a solution of (4-ethyl-thiophen-2-yl)methanol (369 mg, 2 mmol) in THF (10 ml) is added sodium hydride, 60% dispersion in mineral oil, (88 mg, 2.2 mmol) in one portion and the reaction stirred at room temp for 3 hours. The resulting dark yellow solution is then cooled to 0° C., and 5-Chloro-10-oxa-tricyclo[5.2.1.0*2,6*]dec-4-en-3-one (341 mg, 2.4 mmol) is added and the resulting brown solution allowed to warm to ambient over 30 minutes, then stirred at room temp for 17 hours. Crude reaction is purified by flash chromatography to give 5-(4-ethyl-thiophen-2-ylmethoxy)-10-oxa-tricyclo[5.2.1.0*2,6*]dec-4-en-3-one as a white solid (515 mg).

Step 4

Preparation of 4-(4-ethyl-2-methyl-thiophen-3-yl)-10-oxa-tricyclo[5.2.1.0*2,6*]decane-3,5-dione

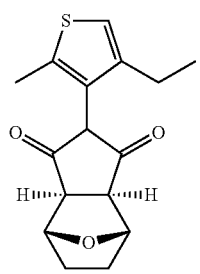 [SMILES: CCc1csc(C)c1C1C(=O)[C@@H]2[C@H](C1=O)[C@H]1CC[C@@H]2O1]

A solution of 5-(4-ethyl-thiophen-2-ylmethoxy)-10-oxa-tricyclo[5.2.1.0*2,6*]dec-4-en-3-one (515 mg, 1.77 mmol) in dimethoxyethane (5 ml) is heated to 200° C. for 30 minutes using microwave irradiation. Silica gel is added to the crude reaction mixture, the solvent is evaporated under reduced pressure and the residue is purified by flash chromatography on silica gel to give 4-(4-ethyl-2-methyl-thiophen-3-yl)-10-oxa-tricyclo[5.2.1.0*2,6*]decane-3,5-dione as a white solid (105 mg).

Step 5

Preparation of 4-(5-bromo-4-ethyl-2-methyl-thiophen-3-yl)-10-oxa-tricyclo[5.2.1.0*2,6*]decane-3,5-dione

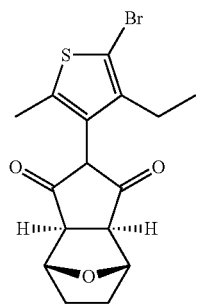 [SMILES: CCc1c(Br)sc(C)c1C1C(=O)[C@@H]2[C@H](C1=O)[C@H]1CC[C@@H]2O1]

To a suspension of 4-(4-ethyl-2-methyl-thiophen-3-yl)-10-oxa-tricyclo[5.2.1.0*2,6*]decane-3,5-dione (73 mg, 0.25 mmol) in DCM (2 ml), at 0° C., is added bromine (26 µl, 0.5 mmol) in one portion, and the reaction allowed to warm to ambient and stirred at room temperature for 3 hours. The reaction is concentrated in vacuo, re-dissolved in methanol (10 ml), potassium carbonate (250 mg) added and the resulting suspension stirred at room temperature for a further 17 hours. The reaction is quenched by the addition if 2N aqueous HCl (10 ml) and extracted with DCM (2×10 ml). The combined organics extracts are dried, filtered, concentrated in vacuo, and purified by flash chromatography on silica gel to give 4-(5-bromo-4-ethyl-2-methyl-thiophen-3-yl)-10-oxa-tricyclo[5.2.1.0*2,6*]decane-3,5-dione as a brown solid (43 mg).

Example 6

Preparation of 4-(6-chloro-4-methyl-pyridin-3-yl)-10-oxa-tricyclo[5.2.1.0*2,6*]decane-3,5-dione

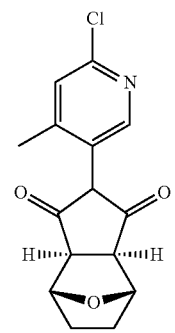 [SMILES: Cc1cc(Cl)ncc1C1C(=O)[C@@H]2[C@H](C1=O)[C@H]1CC[C@@H]2O1]

Step 1

Preparation of 5-methoxy-10-oxa-tricyclo[5.2.1.0*2,6*]dec-4-en-3-one

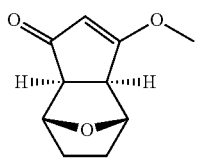

To a suspension of 10-oxa-tricyclo[5.2.1.0*2,6*]decane-3,5-dione (9.97 g, 60 mmol) in methanol (200 ml) is added sodium tetrachloroaurate (597 mg, 1.5 mmol) and the reaction mixture is heated to 60° C. for 7 hours. The reaction mixture is allowed to cool down to room temperature and left to stand overnight. The reaction mixture is concentrated under reduced pressure, dissolved in ethyl acetate (200 ml) and washed with aqueous 2N sodium carbonate (100 ml), followed by saturated brine (100 ml). The organic layer is then dried over magnesium sulphate and concentrated under reduced pressure to give 5-methoxy-10-oxa-tricyclo[5.2.1.0*2,6*]dec-4-en-3-one (8.62 g)

Step 2

Preparation of 4-Iodo-5-methoxy-10-oxa-tricyclo[5.2.1.0*2,6*]dec-4-en-3-one

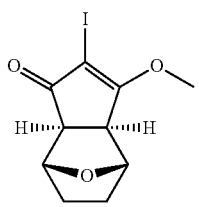

A flask is charged with 5-methoxy-10-oxa-tricyclo[5.2.1.0*2,6*]dec-4-en-3-one (3.96 g, 22 mmol), cerium ammonium nitrate (13.3 g, 24.2 mmol) and iodine (6.73 mg, 26.5 mmol) and then purged with nitrogen. Anhydrous acetonitrile (120 ml) is added, and the reaction heated to 40° C., with stirring for 2 hours. The crude reaction mixture is poured onto a saturated aqueous solution of sodium metabisulphite (250 ml) and extracted with dichloromethane (2×250 ml). The combined organics are dried over magnesium sulphate, filtered, and the solvent is removed under reduced pressure to give 4-Iodo-5-methoxy-10-oxa-tricyclo[5.2.1.0*2,6*]dec-4-en-3-one (5.70 g)

Step 3

Preparation of 4-(6-chloro-4-methyl-pyridin-3-yl)-5-methoxy-10-oxa-tricyclo[5.2.1.0*2,6*]dec-4-en-3-one

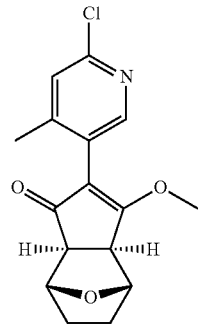

A microwave vial is charged with 4-iodo-5-methoxy-10-oxa-tricyclo[5.2.1.0*2,6*]dec-4-en-3-one (184 mg, 0.6 mmol), 6-chloro-4-methylpyridine-3-boronic acid (103 mg, 0.6 mmol) and bis(triphenylphosphine)palladium dichloride (21 mg, 0.03 mmol). DME (1 ml) is added, followed by 2N aqueous sodium carbonate solution (0.6 ml, 1.2 mmol) and the reaction is heated to 130° C. by microwave irradiation, with stirring, for 30 minutes. The reaction is then diluted with 2N HCl (20 ml), extracted with ethyl acetate (20 ml), and the organic layer is removed and purified by flash chromatography on silica gel to give 4-(6-chloro-4-methyl-pyridin-3-yl)-5-methoxy-10-oxa-tricyclo[5.2.1.0*2,6*]dec-4-en-3-one (119 mg).

Step 4

Preparation of 4-(6-chloro-4-methyl-pyridin-3-yl)-10-oxa-tricyclo[5.2.1.0*2,6*]decane-3,5-dione

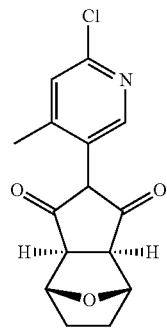 [SMILES: Cc1cc(Cl)ncc1C1C(=O)[C@@H]2[C@H](C1=O)[C@H]1CC[C@@H]2O1]

To a solution of 4-(6-chloro-4-methyl-pyridin-3-yl)-5-methoxy-10-oxa-tricyclo[5.2.1.0*2,6*]dec-4-en-3-one (119 mg) in acetone (1 ml) in a microwave vial is added 2N HCl (0.6 ml) and the resultant solution is heated to 130° C. by microwave irradiation, with stirring, for 30 minutes. The crude reaction mixture is quenched with sodium hydrogen carbonate until the cessation of effervescence, and the reaction partitioned between ethyl acetate (40 ml) and saturated aqueous ammonium chloride (40 ml). The organic layer is removed, washed with saturated brine solution, dried over magnesium sulphate, filtered, and the solvent is removed from the filtrate under reduced pressure to give 4-(6-chloro-4-methyl-pyridin-3-yl)-10-oxa-tricyclo[5.2.1.0*2,6*]decane-3,5-dione (104 mg).

Example 7

Preparation of 4-(5-Methyl-2-methylsulfanyl-pyrimidin-4-yl)-10-oxa-tricyclo[5.2.1.0*2,6*]-decane-3,5-dione

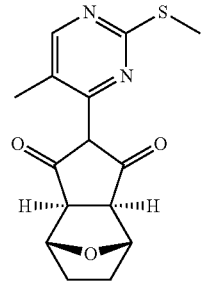

A microwave vial is charged with 4-chloro-5-methyl-2-methylsulfanylpyrimidine (174 mg, 1 mmol), 10-oxa-tricyclo[5.2.1.0*2,6*]decane-3,5-dione (166 mg, 1 mmol), palladium acetate (12 mg, 0.05 mmol), X-Phos (48 mg, 0.1 mmol) and potassium phosphate (424 mg, 2 mmol). 1,2-dimethoxyethane (3 ml) is added and the reaction heated to 160° C., with stirring, for 30 minutes. Silica gel is added to the crude reaction mixture, the solvent is evaporated under reduced pressure and the residue is purified by flash chromatography on silica gel to give 4-(5-methyl-2-methylsulfanyl-pyrimidin-4-yl)-10-oxa-tricyclo[5.2.1.0*2,6*]decane-3,5-dione (34 mg).

Additional compounds in Table T1 below are prepared by similar methods using appropriate starting materials.

Where more than one tautomer or rotational conformer is observed in the proton NMR spectrum, the data shown below are for the mixture of isomers and conformers.

TABLE T1
| Compound Number | Structure | ¹H nmr (CDCl₃ unless stated) or other physical data |
|---|---|---|
| T1 | 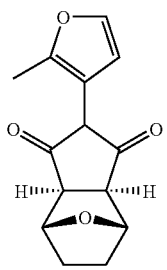 [SMILES: Cc1occc1C1C(=O)[C@@H]2[C@H](C1=O)[C@H]1CC[C@@H]2O1] | (CD₃OD) δ ppm 1.66 (q, 2 H), 1.77-1.88 (m, 2 H), 2.21 (s, 3 H), 2.82 (s, 2 H), 4.60 (dd, 2 H), 6.39 (d, 1 H), 7.34 (d, 1 H) |
| T2 | 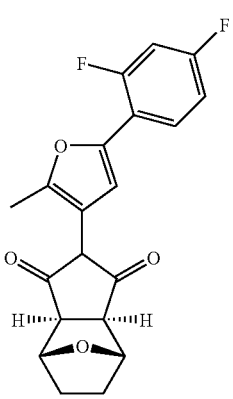 [SMILES: Cc1oc(-c2ccc(F)cc2F)cc1C1C(=O)[C@@H]2[C@H](C1=O)[C@H]1CC[C@@H]2O1] | (CD₃OD) δ ppm 1.56-1.65 (m, 2 H), 1.72-1.83 (m, 2 H), 2.27 (s, 3 H), 2.63 (s, 2 H), 4.53-4.67 (m, 2 H), 6.02 (d, 1 H), 6.72-6.81 (m, 1 H), 6.88-7.06 (m, 2 H) |
| T3 | 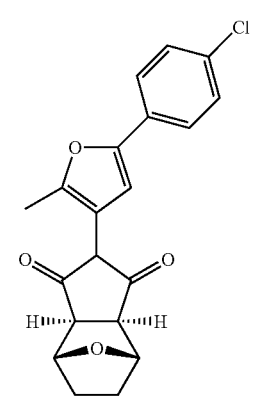 [SMILES: Cc1oc(-c2ccc(Cl)cc2)cc1C1C(=O)[C@@H]2[C@H](C1=O)[C@H]1CC[C@@H]2O1] | (CD₃OD) δ ppm 1.59-1.73 (m, 2 H), 1.76-1.92 (m, 2 H), 2.66 (s, 3 H), 2.78-2.99 (m, 2 H), 4.49-4.73 (m, 2 H), 6.12-6.13 (m, 1 H), 7.49-7.61 (m, 2 H), 7.71-7.83 (m, 2 H) |
| T4 | 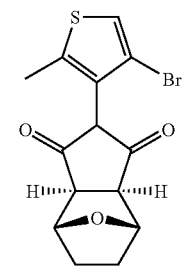 [SMILES: Cc1scc(Br)c1C1C(=O)[C@@H]2[C@H](C1=O)[C@H]1CC[C@@H]2O1] | δ ppm 1.51 (q, 2 H), 1.74-1.82 (m, 2 H), 2.25 (s, 3 H), 2.74 (s, 2 H), 4.59-4.62 (m, 2 H), 7.03 (s, 1 H) |

TABLE T1-continued

| Compound Number | Structure | $^1$H nmr (CDCl$_3$ unless stated) or other physical data |
| --- | --- | --- |
| T5 | 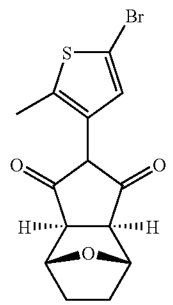 [SMILES: Cc1sc(Br)cc1C1C(=O)[C@@H]2[C@H](C1=O)[C@H]1CC[C@@H]2O1] | (DMSO-d6) δ ppm 1.51-1.58 (m, 2 H), 1.63-1.72 (m, 2 H), 2.17 (s, 3 H), 2.70 (s, 2 H), 4.46-4.54 (m, 2 H), 6.85 (s, 1 H) |
| T6 | 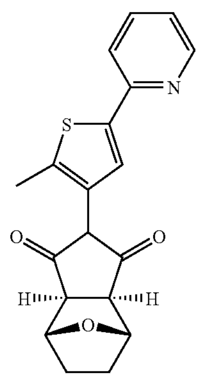 [SMILES: Cc1sc(-c2ccccn2)cc1C1C(=O)[C@@H]2[C@H](C1=O)[C@H]1CC[C@@H]2O1] | δ ppm 1.53-1.62 (m, 2 H), 1.78-1.89 (m, 2 H), 2.24 (s, 3 H), 2.77 (s, 2 H) 4.67-4.79 (m, 2 H), 7.07-7.13 (m, 1 H), 7.29 (s, 1 H), 7.38 (d, 1 H), 7.63 (td, 1 H), 8.31 (d, 1 H) |
| T7 | 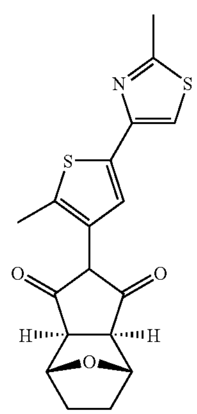 [SMILES: Cc1nc(-c2cc(C3C(=O)[C@@H]4[C@H](C3=O)[C@H]3CC[C@@H]4O3)c(C)s2)cs1] | (CD$_3$OD) δ ppm 1.65-1.72 (m, 2 H), 1.77-1.89 (m, 2 H), 2.31 (s, 3 H), 2.85 (s, 2 H), 4.61-4.67 (m, 2 H), 7.24 (s, 1 H), 7.38 (s, 1 H) |
| T8 | 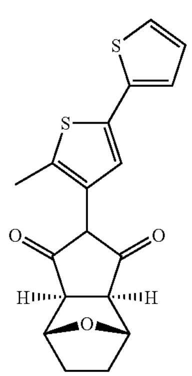 [SMILES: Cc1sc(-c2cccs2)cc1C1C(=O)[C@@H]2[C@H](C1=O)[C@H]1CC[C@@H]2O1] | δ ppm 1.53-1.61 (m, 2 H), 1.79-1.87 (m, 2 H), 2.30 (s, 3 H), 2.78 (s, 2 H), 4.67-4.71 (m, 2 H), 6.92 (s, 1 H), 6.95-7.01 (m, 1 H), 7.06-7.11 (m, 1 H), 7.17 (d, 1 H) |

TABLE T1-continued

| Compound Number | Structure | ¹H nmr (CDCl₃ unless stated) or other physical data |
| --- | --- | --- |
| T9 | 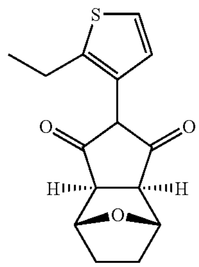 [SMILES: CCc1sccc1C1C(=O)[C@@H]2[C@H](C1=O)[C@H]1CC[C@@H]2O1] | δ ppm 1.25 (t, 3 H), 1.50-1.62 (m, 4 H), 1.76-1.90 (m, 2 H), 2.69 (q, 2 H), 4.68-4.74 (m, 2 H), 6.84 (d, 1 H), 7.02 (d, 1 H) |
| T10 | 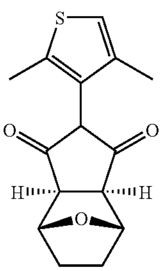 [SMILES: Cc1csc(C)c1C1C(=O)[C@@H]2[C@H](C1=O)[C@H]1CC[C@@H]2O1] | δ ppm 1.44-1.53 (m, 2 H), 1.74-1.82 (m, 2 H), 1.99 (s, 3 H), 2.21 (d, 3 H), 2.68 (d, 2 H), 4.58 (m, 2 H), 6.70 (d, 1 H) |
| T11 | 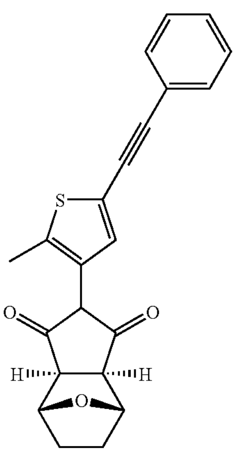 [SMILES: Cc1sc(C#Cc2ccccc2)cc1C1C(=O)[C@@H]2[C@H](C1=O)[C@H]1CC[C@@H]2O1] | (CD₃OD) δ ppm 1.64-1.72 (m, 2 H), 1.80-1.89 (m, 2 H), 2.30 (s, 3 H), 2.85 (s, 2 H), 4.62 (dd, 2 H), 7.05 (s, 1 H), 7.36-7.41 (m, 3 H), 7.46-7.50 (m, 2 H) |
| T12 | 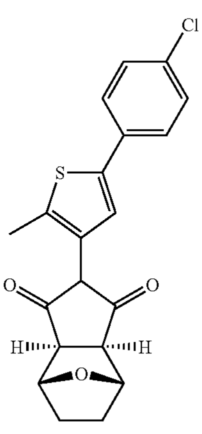 [SMILES: Cc1sc(-c2ccc(Cl)cc2)cc1C1C(=O)[C@@H]2[C@H](C1=O)[C@H]1CC[C@@H]2O1] | (DMSO-D6) δ ppm 1.45-1.53 (m, 2 H), 1.56-1.71 (m, 2 H), 2.18 (s, 3 H), 2.70 (s, 2 H), 4.41-4.52 (m, 2 H), 7.14 (s, 1 H), 7.36 (m, 2 H), 7.51 (m, 2 H) |

TABLE T1-continued

| Compound Number | Structure | ¹H nmr (CDCl₃ unless stated) or other physical data |
|---|---|---|
| T13 | 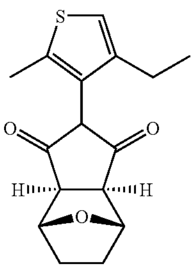 [SMILES: CCc1csc(C)c1C1C(=O)[C@@H]2[C@H](C1=O)[C@H]1CC[C@@H]2O1] | δ ppm 1.12 (td, 3 H), 1.53-1.62 (m, 2 H), 1.80-1.97 (m, 2 H), 2.24 (s, 3 H), 2.36 (ddd, 2 H), 2.79 (s, 2 H), 4.64-4.73 (m, 2 H), 6.77 (s, 1 H) |
| T14 | 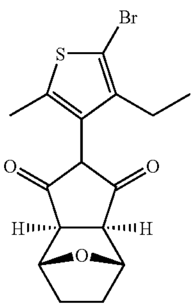 [SMILES: CCc1c(Br)sc(C)c1C1C(=O)[C@@H]2[C@H](C1=O)[C@H]1CC[C@@H]2O1] | δ ppm 0.97 (t, 3 H), 1.51-1.67 (m, 2 H), 1.78-1.91 (m, 2 H), 2.17 (s, 3 H), 2.35 (dt, 2 H), 2.80 (d, 2 H), 4.63-4.76 (m, 2 H) |
| T15 | 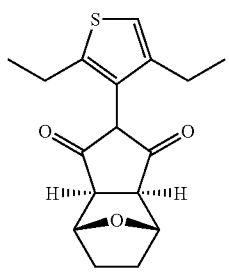 [SMILES: CCc1csc(CC)c1C1C(=O)[C@@H]2[C@H](C1=O)[C@H]1CC[C@@H]2O1] | δ ppm 1.11 (td, 3 H), 1.18 (td, 3 H), 1.47-1.55 (m, 2 H), 1.75-1.83 (m, 2 H), 2.27-2.40 (m, 2 H), 2.57 (ddd, 2 H), 2.72 (d, 2 H), 4.58-4.66 (m, 2 H), 6.77 (s, 1 H) |
| T16 | 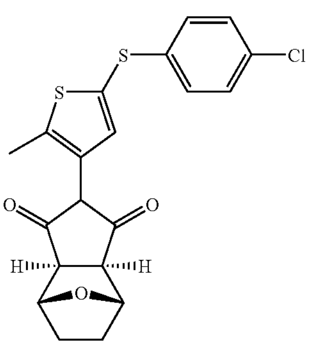 [SMILES: Cc1sc(Sc2ccc(Cl)cc2)cc1C1C(=O)[C@@H]2[C@H](C1=O)[C@H]1CC[C@@H]2O1] | (CD₃OD) δ ppm 1.57-1.67 (m, 2 H), 1.73-1.83 (m, 2 H), 2.28 (s, 3 H), 2.71 (s, 2 H), 4.48-4.55 (m, 2 H), 6.78 (s, 1 H), 7.05-7.13 (m, 2 H), 7.20-7.26 (m, 2 H) |

TABLE T1-continued

| Compound Number | Structure | $^1$H nmr (CDCl$_3$ unless stated) or other physical data |
|---|---|---|
| T17 | 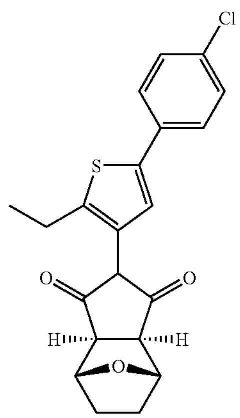 [SMILES: CCc1sc(-c2ccc(Cl)cc2)cc1C1C(=O)[C@@H]2[C@H](C1=O)[C@H]1CC[C@@H]2O1] | (CD$_3$OD) δ ppm 1.22 (t, 3 H), 1.62-1.68 (m, 2 H), 1.76-1.84 (m, 2 H), 2.68 (q, 2 H), 2.77 (s, 2 H), 4.56-4.61 (m, 2 H), 7.11 (s, 1 H), 7.30-7.36 (m, 2 H), 7.51-7.57 (m, 2 H) |
| T18 | 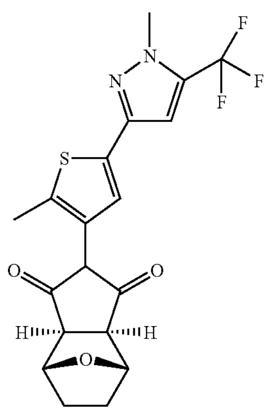 [SMILES: Cc1sc(-c2cc(C(F)(F)F)n(C)n2)cc1C1C(=O)[C@@H]2[C@H](C1=O)[C@H]1CC[C@@H]2O1] | δ ppm 1.59-1.69 (m, 2 H), 1.85-1.96 (m, 2 H), 2.36 (s, 3 H), 2.86 (s, br, 2 H), 4.02 (s, 3 H), 4.71-4.79 (m, 2 H), 6.76 (s, 1 H), 7.09 (s, 1 H) |
| T19 | 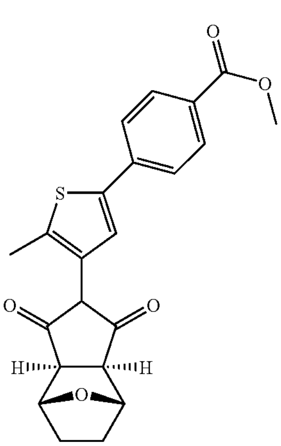 [SMILES: COC(=O)c1ccc(-c2cc(C3C(=O)[C@@H]4[C@H](C3=O)[C@H]3CC[C@@H]4O3)c(C)s2)cc1] | δ ppm 1.53-1.66 (m, 2 H), 1.82-1.93 (m, 2 H), 2.35 (s, 3 H), 2.81 (s, 2 H) 3.91 (s, 3 H), 4.68-4.77 (m, 2 H), 7.18 (s, 1 H), 7.51-7.68 (m, 2 H), 7.94-8.06 (m, 2 H) |

TABLE T1-continued

| Compound Number | Structure | ¹H nmr (CDCl₃ unless stated) or other physical data |
|---|---|---|
| T20 | 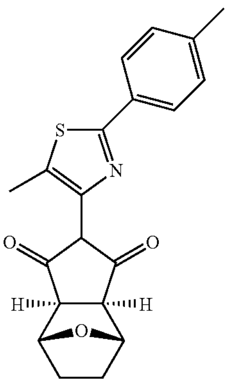 [SMILES: Cc1ccc(-c2nc(C3C(=O)[C@@H]4[C@H](C3=O)[C@H]3CC[C@@H]4O3)c(C)s2)cc1] | δ ppm 1.55-1.65 (m, 2 H), 1.81-1.95 (m, 2 H), 2.41 (s, 3 H), 2.78 (s, 2 H), 2.86 (s, 3 H), 4.70-4.79 (m, 2 H), 7.26 (d, 2 H), 7.69 (d, 2 H) |
| T21 | 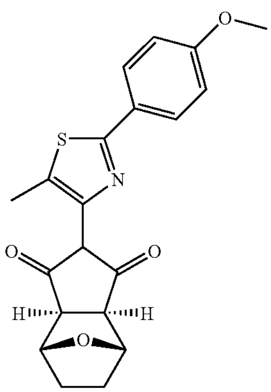 [SMILES: COc1ccc(-c2nc(C3C(=O)[C@@H]4[C@H](C3=O)[C@H]3CC[C@@H]4O3)c(C)s2)cc1] | δ ppm 1.60 (q, 2 H), 1.83-1.91 (m, 2 H), 2.78 (s, 2 H), 2.85 (s, 3 H), 3.87 (s, 3 H), 4.75 (dd, 2 H), 6.92-7.01 (m, 2 H), 7.69-7.81 (m, 2 H) |
| T22 | 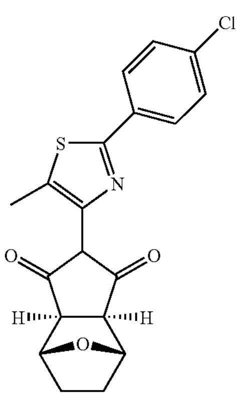 | δ ppm 1.61 (q, 2 H), 1.87 (ddd, 2 H), 2.79 (s, 2 H), 2.86 (s, 3 H), 4.75 (dd, 2 H), 7.39-7.49 (m, 2 H), 7.70-7.76 (m, 2 H) |
| T23 | 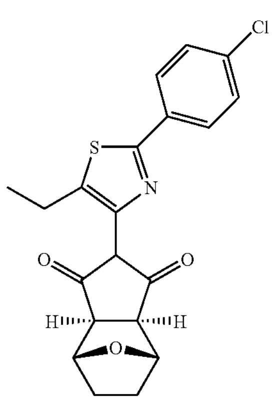 [SMILES: CCc1sc(-c2ccc(Cl)cc2)nc1C1C(=O)[C@@H]2[C@H](C1=O)[C@H]1CC[C@@H]2O1] | δ ppm 1.32 (t, 3 H), 1.61 (q, 2 H), 1.83-1.92 (m, 2 H), 2.79 (s, 2 H), 3.41 (q, 2 H), 4.73-4.79 (m, 2 H), 7.39-7.47 (m, 2 H), 7.71-7.80 (m, 2 H) |

TABLE T1-continued

| Compound Number | Structure | ¹H nmr (CDCl₃ unless stated) or other physical data |
|---|---|---|
| T24 | 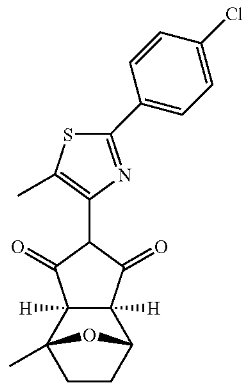 [SMILES: Cc1sc(-c2ccc(Cl)cc2)nc1C1C(=O)[C@H]2[C@@H]3CC[C@@](C)(O3)[C@H]2C1=O] | δ ppm 1.55-1.76 (m, 6 H), 1.94-2.05 (m, 1 H), 2.71 (d, 1 H), 2.86 (m, 4 H), 4.68 (d, 2 H), 7.43 (d, 2 H), 7.73 (d, 2 H) |
| T25 | 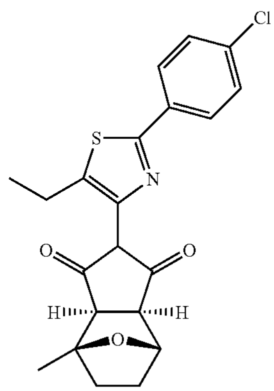 [SMILES: CCc1sc(-c2ccc(Cl)cc2)nc1C1C(=O)[C@H]2[C@@H]3CC[C@@](C)(O3)[C@H]2C1=O] | δ ppm 1.32 (t, 3 H), 1.56-1.75 (m, 6 H), 1.94-2.06 (m, 1 H) 2.70 (d, 1 H), 2.87 (d, 1 H), 3.41 (qd, 2 H), 4.68 (d, 2 H), 7.43 (d, 2 H), 7.74 (d, 2 H) |
| T26 | 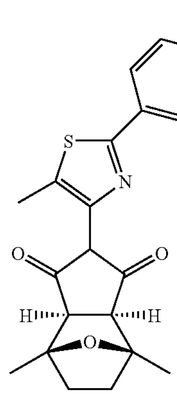 | δ ppm 1.61 (s, 6 H), 1.71-1.85 (m, 4 H), 2.79 (s, br, 2 H), 2.83 (s, 3 H), 7.39-7.47 (m, 2 H), 7.70-7.79 (m, 2 H) |
| T27 | 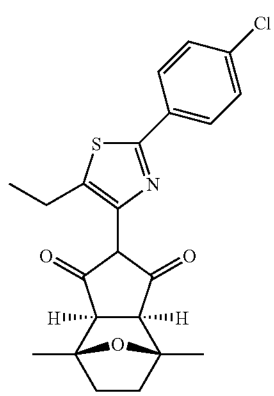 [SMILES: CCc1sc(-c2ccc(Cl)cc2)nc1C1C(=O)[C@@H]2[C@H](C1=O)[C@@]1(C)CC[C@]2(C)O1] | δ ppm 1.33 (t, 3 H), 1.61 (s, 6 H), 1.72-1.80 (m, 4 H), 2.79 (s, br, 2 H), 3.35-3.46 (m, 2 H), 7.39-7.47 (m, 2 H), 7.70-7.78 (m, 2 H) |

TABLE T1-continued

| Compound Number | Structure | ¹H nmr (CDCl₃ unless stated) or other physical data |
| --- | --- | --- |
| T28 | 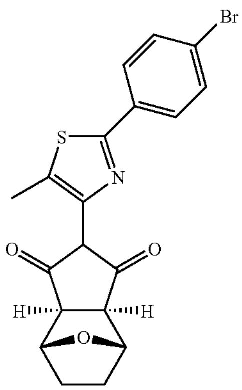 [SMILES: Cc1sc(-c2ccc(Br)cc2)nc1C1C(=O)[C@@H]2[C@H](C1=O)[C@H]1CC[C@@H]2O1] | δ ppm 1.61 (q, 2 H), 1.83-1.94 (m, 2 H), 2.79 (s, 2 H), 2.86 (s, 3 H), 4.75 (dd, 2 H), 7.56-7.62 (m, 2 H), 7.63-7.71 (m, 2 H) |
| T29 | 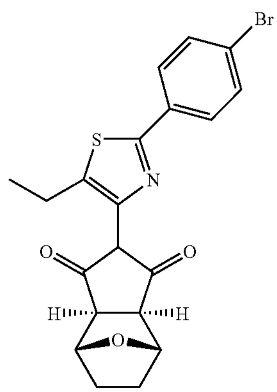 [SMILES: CCc1sc(-c2ccc(Br)cc2)nc1C1C(=O)[C@@H]2[C@H](C1=O)[C@H]1CC[C@@H]2O1] | δ ppm 1.32 (t, 3 H), 1.56-1.66 (m, 2 H), 1.83-1.94 (m, 2 H), 2.79 (s, 2 H), 3.41 (q, 2 H), 4.75 (dd, 2 H), 7.57-7.64 (m, 2 H), 7.65-7.72 (m, 2 H) |
| T30 | 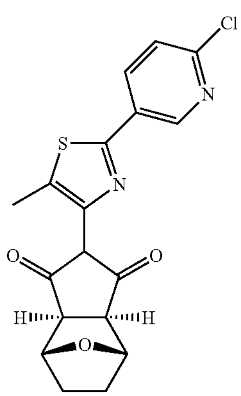 [SMILES: Cc1sc(-c2ccc(Cl)nc2)nc1C1C(=O)[C@@H]2[C@H](C1=O)[C@H]1CC[C@@H]2O1] | δ ppm 1.58-1.67 (m, 2 H), 1.84-1.92 (m, 2 H), 2.80 (s, br, 2 H), 2.88 (s, 3 H), 4.72-4.79 (m, 2 H), 7.41-7.47 (m, 1 H), 8.04 (dd, 1 H), 8.81 (d, 2 H) |
| T31 | 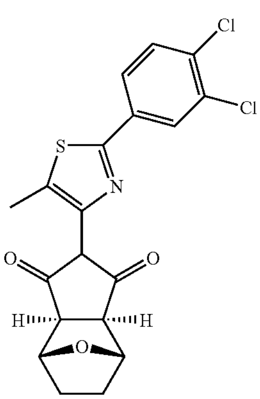 [SMILES: Cc1sc(-c2ccc(Cl)c(Cl)c2)nc1C1C(=O)[C@@H]2[C@H](C1=O)[C@H]1CC[C@@H]2O1] | δ ppm 1.58-1.65 (m, 2 H), 1.85-1.91 (m, 2 H), 2.80 (s, br, 2 H), 2.86 (s, 3 H), 4.75 (dd, 2 H), 7.53 (d, 1 H), 7.62 (dd, 1 H), 7.87 (d, 1 H) |

TABLE T1-continued

| Compound Number | Structure | ¹H nmr (CDCl₃ unless stated) or other physical data |
|---|---|---|
| T32 | 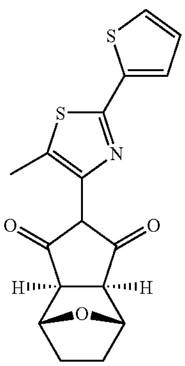 [SMILES: Cc1sc(-c2cccs2)nc1C1C(=O)[C@@H]2[C@H](C1=O)[C@H]1CC[C@@H]2O1] | δ ppm 1.56-1.64 (m, 2 H), 1.84-1.89 (m, 2 H), 2.77 (s, 2 H), 2.83 (s, 3 H) 4.70-4.79 (m, 2 H), 7.09 (dd, 1 H), 7.40-7.43 (m, 1 H), 7.43-7.46 (m, 1 H) |
| T33 | 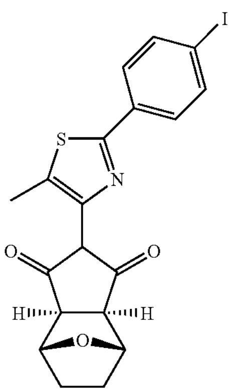 [SMILES: Cc1sc(-c2ccc(I)cc2)nc1C1C(=O)[C@@H]2[C@H](C1=O)[C@H]1CC[C@@H]2O1] | δ ppm 1.61 (m, 2 H), 1.87 (m, 2 H), 2.79 (s, 2 H), 2.82 (s, 3 H), 4.74 (t, 2 H), 7.52 (d, 2 H), 7.80 (d, 2 H) |
| T34 | 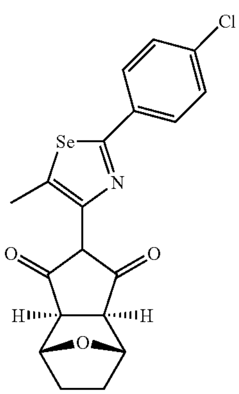 | δ ppm 1.58-1.63 (m, 2 H), 1.84-1.90 (m, 2 H), 2.79 (s, 2 H), 2.91 (t, 3 H), 4.75 (dd, 2 H), 7.42 (dt, 2 H), 7.68 (dt, 2 H) |
| T35 | 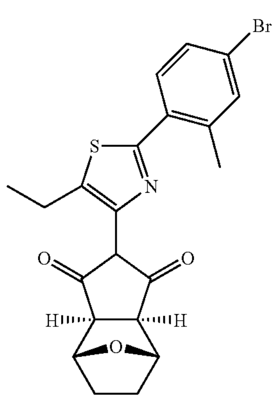 [SMILES: CCc1sc(-c2ccc(Br)cc2C)nc1C1C(=O)[C@@H]2[C@H](C1=O)[C@H]1CC[C@@H]2O1] | δ ppm 1.33 (t, 3 H), 1.60 (q, 2 H), 1.83-1.89 (m, 2 H), 2.53 (s, 3 H), 2.77 (s, 2 H), 3.43 (q, 2 H), 4.74 (dd, 2 H), 7.43 (dd, 1 H), 7.47-7.49 (m, 2 H) |

TABLE T1-continued

| Compound Number | Structure | ¹H nmr (CDCl₃ unless stated) or other physical data |
|---|---|---|
| T36 | 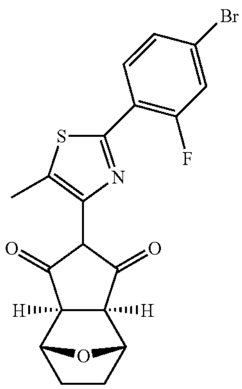 [SMILES: Cc1sc(-c2ccc(Br)cc2F)nc1C1C(=O)[C@@H]2[C@H](C1=O)[C@H]1CC[C@@H]2O1] | δ ppm 1.56-1.65 (m, 2 H), 1.84-1.92 (m, 2 H), 2.80 (s, 2 H), 2.88 (s, 3 H), 4.71-4.80 (m, 2 H), 7.41 (dd, 1 H), 7.44 (d, 1 H), 7.81 (dd, 1 H) |
| T37 | 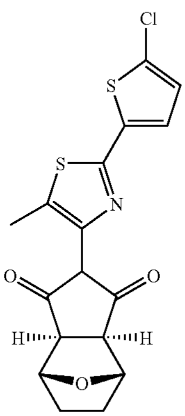 [SMILES: Cc1sc(-c2ccc(Cl)s2)nc1C1C(=O)[C@@H]2[C@H](C1=O)[C@H]1CC[C@@H]2O1] | δ ppm 1.56-1.64 (m, 2 H), 1.83-1.90 (m, 2 H), 2.77 (s, 2 H), 2.82 (s, 3 H), 4.71-4.75 (m, 2 H), 6.91 (d, 1 H), 7.20 (d, 1 H) |
| T38 | 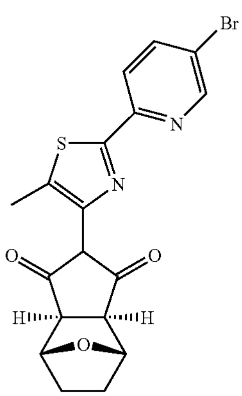 [SMILES: Cc1sc(-c2ccc(Br)cn2)nc1C1C(=O)[C@@H]2[C@H](C1=O)[C@H]1CC[C@@H]2O1] | δ ppm 1.59-1.63 (m, 2 H), 1.83-1.90 (m, 2 H), 2.80 (s(br), 2 H), 2.86 (s, 3 H), 4.75 (dd, 2 H), 7.84 (d, 1 H), 7.94 (dd, 1 H), 8.66 (d, 1 H) |
| T39 | 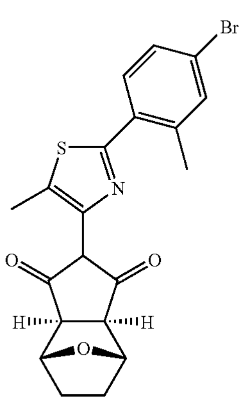 [SMILES: Cc1cc(Br)ccc1-c1nc(C2C(=O)[C@@H]3[C@H](C2=O)[C@H]2CC[C@@H]3O2)c(C)s1] | δ ppm 1.57-1.62 (m, 2 H), 1.85-1.88 (m, 2 H), 2.52 (s, 3 H), 2.78 (s(br), 2 H), 2.88 (s, 3 H), 4.74 (dd, 2 H), 7.42 (dd, 1 H), 7.46 (d, 1 H), 7.48 (d, 1 H) |

TABLE T1-continued
| Compound Number | Structure | ¹H nmr (CDCl₃ unless stated) or other physical data |
|---|---|---|
| T40 | 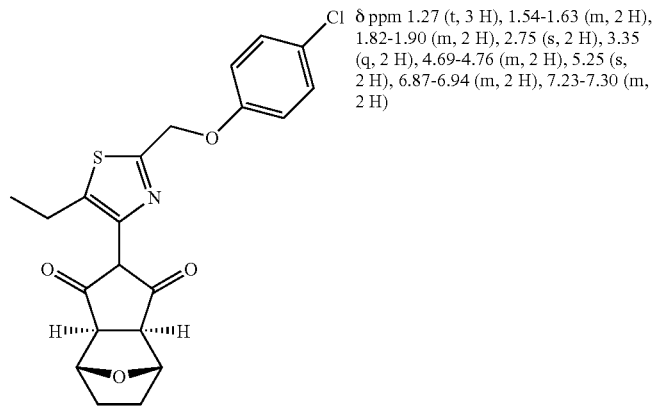 | δ ppm 1.27 (t, 3 H), 1.54-1.63 (m, 2 H), 1.82-1.90 (m, 2 H), 2.75 (s, 2 H), 3.35 (q, 2 H), 4.69-4.76 (m, 2 H), 5.25 (s, 2 H), 6.87-6.94 (m, 2 H), 7.23-7.30 (m, 2 H) |
| T41 | 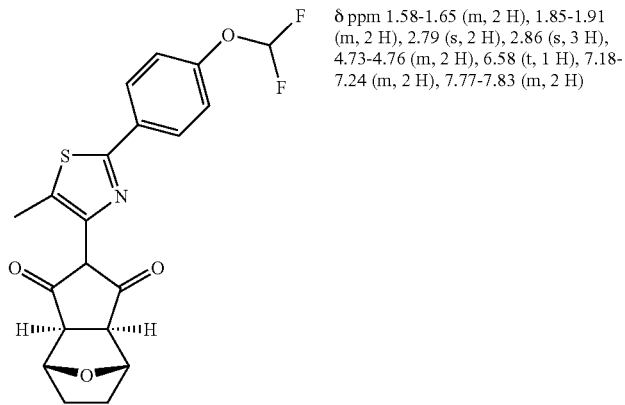 | δ ppm 1.58-1.65 (m, 2 H), 1.85-1.91 (m, 2 H), 2.79 (s, 2 H), 2.86 (s, 3 H), 4.73-4.76 (m, 2 H), 6.58 (t, 1 H), 7.18-7.24 (m, 2 H), 7.77-7.83 (m, 2 H) |
| T42 | 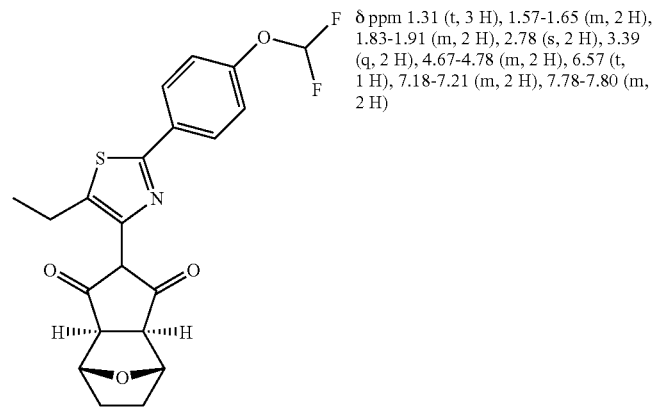 | δ ppm 1.31 (t, 3 H), 1.57-1.65 (m, 2 H), 1.83-1.91 (m, 2 H), 2.78 (s, 2 H), 3.39 (q, 2 H), 4.67-4.78 (m, 2 H), 6.57 (t, 1 H), 7.18-7.21 (m, 2 H), 7.78-7.80 (m, 2 H) |

TABLE T1-continued

| Compound Number | Structure | ¹H nmr (CDCl₃ unless stated) or other physical data |
|---|---|---|
| T43 | 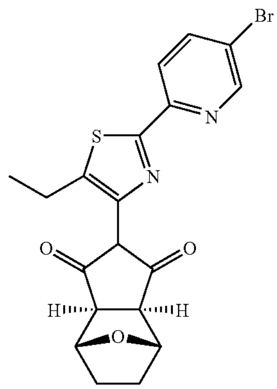 | δ ppm 1.32 (t, 3 H), 1.58-1.63 (m, 2 H), 1.84-1.90 (m, 2 H), 2.79 (s(br), 2 H), 3.40 (q, 2 H), 4.74 (dd, 2 H), 7.84 (d, 1 H), 7.93 (dd, 1 H), 8.65 (d, 1 H) |
| T44 | 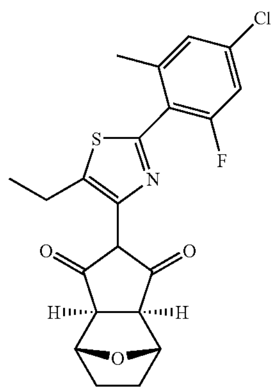 [SMILES: CCc1sc(-c2c(C)cc(Cl)cc2F)nc1C1C(=O)[C@@H]2[C@H](C1=O)[C@H]1CC[C@@H]2O1] | δ ppm 1.40-1.53 (m, 3 H), 1.58-1.64 (m, 2 H), 1.72-1.82 (m, 2 H), 2.11 (s, 3 H), 2.62-2.71 (m, 2 H), 3.54-3.64 (m, 2 H), 4.53-4.63 (m, 2 H), 7.02-7.04 (m, 1 H), 7.09-7.18 (m, 1 H) |
| T45 | 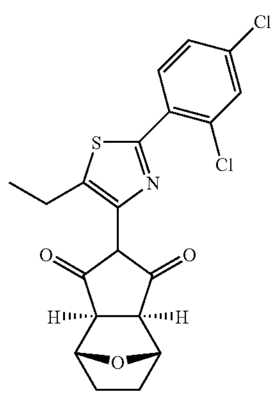 [SMILES: CCc1sc(-c2ccc(Cl)cc2Cl)nc1C1C(=O)[C@@H]2[C@H](C1=O)[C@H]1CC[C@@H]2O1] | δ ppm 1.32 (t, 3 H), 1.58-1.65 (m, 2 H), 1.84-1.92 (m, 2 H), 2.80 (s (br), 2 H), 3.41 (q, 2 H), 4.72-4.77 (m, 2 H), 7.54 (d, 1 H), 7.63 (dd, 1 H), 7.88 (d, 1 H) |
| T46 | 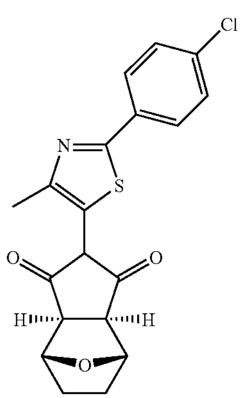 [SMILES: Cc1nc(-c2ccc(Cl)cc2)sc1C1C(=O)[C@@H]2[C@H](C1=O)[C@H]1CC[C@@H]2O1] | δ ppm 1.55 (m, 2 H), 1.65 (m, 2 H), 2.20 (s, 3 H), 2.78 (s, 2 H), 4.5 (s, 2 H), 7.50 (d, 2 H), 7.90 (d, 2 H) |

TABLE T1-continued

| Compound Number | Structure | ¹H nmr (CDCl₃ unless stated) or other physical data |
|---|---|---|
| T47 | 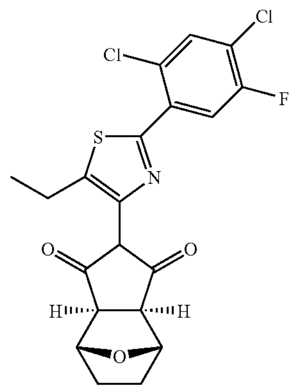 [SMILES: CCc1sc(-c2cc(F)c(Cl)cc2Cl)nc1C1C(=O)[C@@H]2[C@H](C1=O)[C@H]1CC[C@@H]2O1] | δ ppm 1.34 (t, 3 H), 1.56-1.66 (m, 2 H), 1.82-1.95 (m, 2 H), 2.79 (s (br), 2 H), 3.44 (q, 2 H), 4.74-4.84 (m, 2 H), 7.60 (d, 1 H), 7.71 (d, 1 H) |
| T48 | 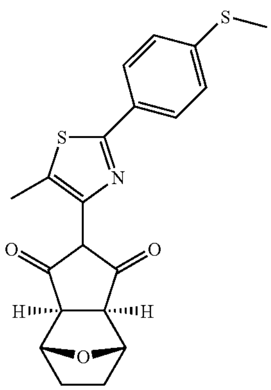 [SMILES: CSc1ccc(-c2nc(C3C(=O)[C@@H]4[C@H](C3=O)[C@H]3CC[C@@H]4O3)c(C)s2)cc1] | δ ppm 1.61 (q, 2 H), 1.84-1.91 (m, 2 H), 2.53 (s, 3 H), 2.78 (s, 2 H), 2.86 (s, 3 H), 4.70-4.79 (m, 2 H), 7.26-7.34 (m, 2 H), 7.65-7.75 (m, 2 H) |
| T49 | 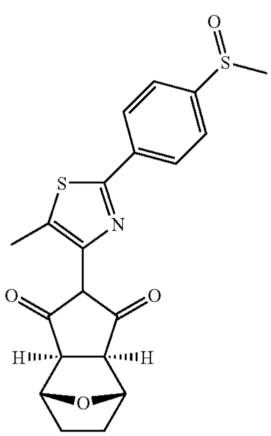 [SMILES: Cc1sc(-c2ccc(S(C)=O)cc2)nc1C1C(=O)[C@@H]2[C@H](C1=O)[C@H]1CC[C@@H]2O1] | δ ppm 1.58-1.67 (m, 2 H), 1.82-1.92 (m, 2 H), 2.78 (s, 3 H), 2.81 (s, 2 H), 2.88 (s, 3 H), 4.72-4.80 (m, 2 H), 7.71-7.78 (m, 2 H), 7.90-7.99 (m, 2 H) |
| T50 | 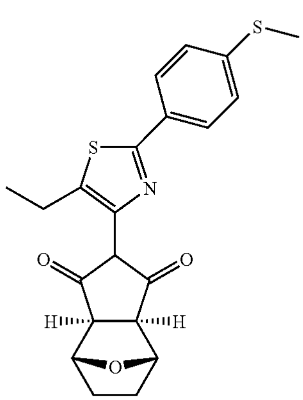 [SMILES: CCc1sc(-c2ccc(SC)cc2)nc1C1C(=O)[C@@H]2[C@H](C1=O)[C@H]1CC[C@@H]2O1] | δ ppm 1.31 (t, 3 H), 1.61 (q, 2 H), 1.83-1.96 (m, 2 H), 2.53 (s, 3 H), 2.78 (s, 2 H), 3.41 (q, 2 H), 4.72-4.79 (m, 2 H), 7.25-7.34 (m, 2 H), 7.68-7.76 (m, 2 H) |

TABLE T1-continued
| Compound Number | Structure | ¹H nmr (CDCl₃ unless stated) or other physical data |
|---|---|---|
| T51 | 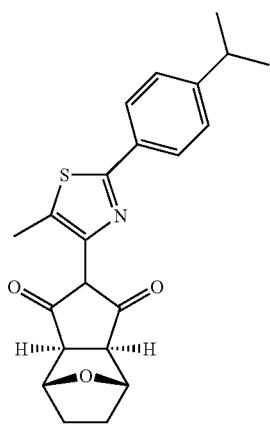 [SMILES: Cc1sc(-c2ccc(C(C)C)cc2)nc1C1C(=O)[C@@H]2[C@H](C1=O)[C@H]1CC[C@@H]2O1] | δ ppm 1.33 (d, 6 H), 1.63-1.67 (m, 2 H), 1.88-1.94 (m, 2 H), 2.83 (s(br), 2 H), 2.90 (s, 3 H), 3.01 (sept, 1 H), 4.79 (dd, 2 H), 7.35 (d, 2 H), 7.77 (d, 2 H) |
| T52 | 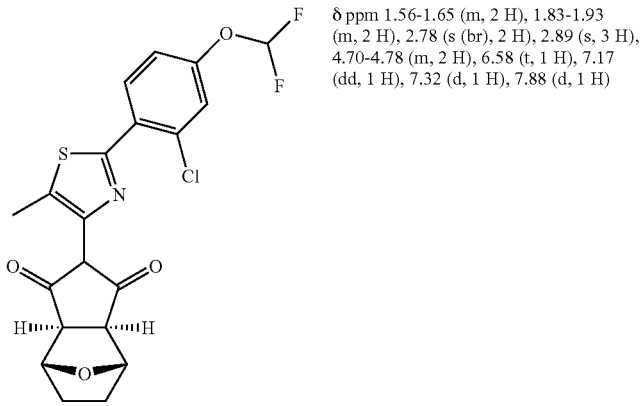 | δ ppm 1.56-1.65 (m, 2 H), 1.83-1.93 (m, 2 H), 2.78 (s (br), 2 H), 2.89 (s, 3 H), 4.70-4.78 (m, 2 H), 6.58 (t, 1 H), 7.17 (dd, 1 H), 7.32 (d, 1 H), 7.88 (d, 1 H) |
| T53 | 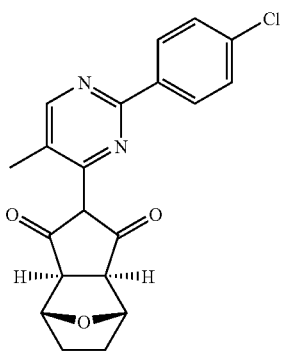 [SMILES: Cc1cnc(-c2ccc(Cl)cc2)nc1C1C(=O)[C@@H]2[C@H](C1=O)[C@H]1CC[C@@H]2O1] | δ ppm 1.55-1.67 (m, 2 H), 1.84-1.87 (m, 2 H), 2.68 (s, 3 H), 2.78 (s, 2 H), 4.81-4.90 (m, 2 H), 7.51-7.63 (m, 2 H), 8.17-8.31 (m, 2 H), 8.54 (s, 1 H) |

TABLE T1-continued

| Compound Number | Structure | ¹H nmr (CDCl₃ unless stated) or other physical data |
|---|---|---|
| T54 | 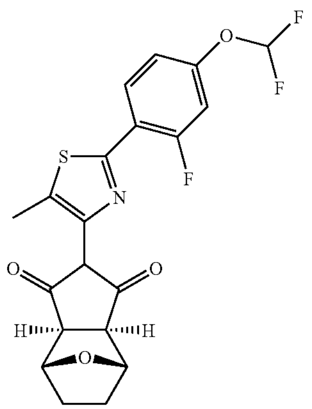 [SMILES: Cc1sc(-c2ccc(OC(F)F)cc2F)nc1C1C(=O)[C@@H]2[C@H](C1=O)[C@H]1CC[C@@H]2O1] | δ ppm 1.55-1.65 (m, 2 H), 1.83-1.92 (m, 2 H), 2.79 (s, 2 H), 2.86 (s, 3 H), 4.71-4.78 (m, 2 H), 6.58 (t, 1 H), 6.97-7.09 (m, 2 H), 7.92 (d, 1 H) |
| T55 | 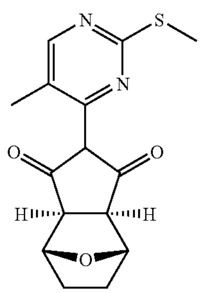 | δ ppm 1.55-1.65 (m, 2 H), 1.79-1.91 (m, 2 H), 2.52 (s, 3 H), 2.67 (s, 3 H), 2.74 (s, 2 H), 4.78-4.83 (m, 2 H), 8.28 (s, 1 H) |
| T56 | 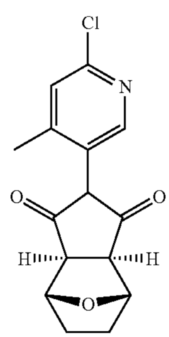 [SMILES: Cc1cc(Cl)ncc1C1C(=O)[C@@H]2[C@H](C1=O)[C@H]1CC[C@@H]2O1] | δ ppm 1.56-1.67 (m, 2 H), 1.80-1.94 (m, 2 H), 2.25 (s, 3 H), 2.82 (s, 2 H), 4.72-4.83 (m, 2 H), 6.98 (s, 1 H), 7.79 (s, 1 H) |
| T57 | 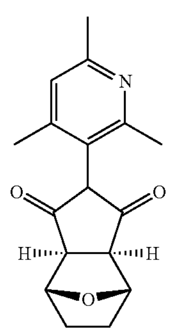 | (CD₃OD) δ ppm 1.65-1.72 (m, 2 H), 1.80-1.88 (m, 2 H), 2.36 (d, 3 H), 2.49 (d, 3 H), 2.69 (s, 3 H), 2.98 (d, 2 H), 4.59-4.65 (m, 2 H), 7.60 (s, 1 H) |

TABLE T1-continued

| Compound Number | Structure | $^1$H nmr (CDCl$_3$ unless stated) or other physical data |
|---|---|---|
| T58 | 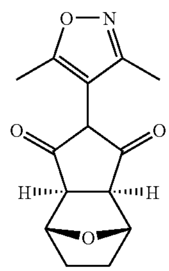 [SMILES: Cc1noc(C)c1C1C(=O)[C@@H]2[C@H](C1=O)[C@H]1CC[C@@H]2O1] | δ ppm 1.52-1.70 (m, 2 H), 1.81-1.91 (m, 2 H), 2.01 (s, 3 H), 2.25 (s, 3 H), 2.81 (s, 2 H), 4.68-4.72 (m, 2 H) |

Example 8
Preparation of cyclopropanecarboxylic acid-4-[2-(4-chloro-phenyl)-5-ethyl-thiazol-4-yl]-5-oxo-10-oxa-tricyclo[5.2.1.0*2,6*]dec-3-en-3-yl ester

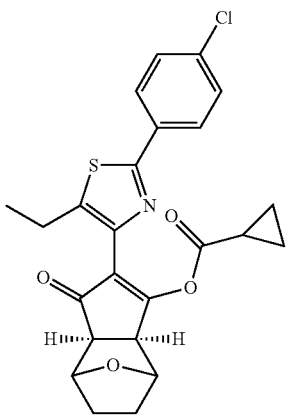 [SMILES: CCc1sc(-c2ccc(Cl)cc2)nc1C1=C(OC(=O)C2CC2)[C@H]2C3CCC(O3)[C@H]2C1=O]

To a solution of 4-[2-(4-chloro-phenyl)-5-ethyl-thiazol-4-yl]-10-oxa-tricyclo[5.2.1.0*2,6*]decane-3,5-dione (100 mg, 0.18 mmol) in DCM (5 ml) and triethylamine (140 μl, 1 mmol) is added the cyclopropane carbonyl chloride (91 μl, 1 mmol) at room temperature. The reaction mixture is stirred overnight at room temperature. Silica gel is added to the crude reaction mixture, the solvent is evaporated under reduced pressure and the residue is purified by flash chromatography on silica gel to give cyclopropanecarboxylic acid-4-[2-(4-chloro-phenyl)-5-ethyl-thiazol-4-yl]-5-oxo-10-oxa-tricyclo [5.2.1.0*2,6*]dec-3-en-3-yl ester (102 mg).

Additional compounds in Table P1 below are prepared by similar methods using appropriate starting materials.

Where more than one tautomer or rotational conformer is observed in the proton NMR spectrum, the data shown below are for the mixture of isomers and conformers.

TABLE P1

| Compound Number | Structure | $^1$H nmr (CDCl$_3$ unless stated) or other physical data |
|---|---|---|
| P1 | 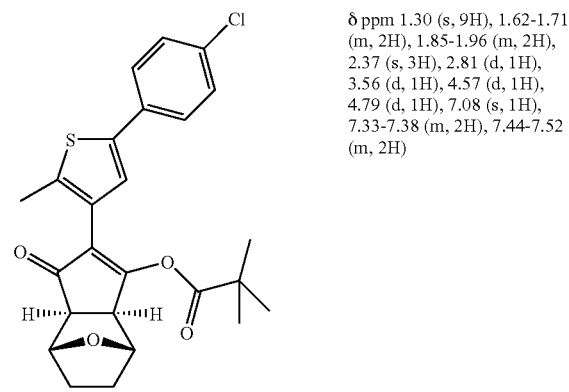 | δ ppm 1.30 (s, 9H), 1.62-1.71 (m, 2H), 1.85-1.96 (m, 2H), 2.37 (s, 3H), 2.81 (d, 1H), 3.56 (d, 1H), 4.57 (d, 1H), 4.79 (d, 1H), 7.08 (s, 1H), 7.33-7.38 (m, 2H), 7.44-7.52 (m, 2H) |

TABLE P1-continued

| Compound Number | Structure | ¹H nmr (CDCl₃ unless stated) or other physical data |
|---|---|---|
| P2 | 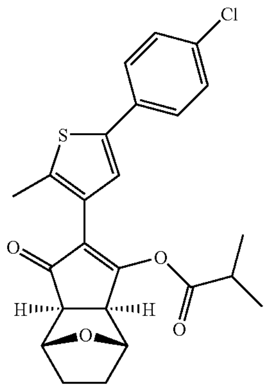 [SMILES: Cc1sc(-c2ccc(Cl)cc2)cc1C1=C(OC(=O)C(C)C)[C@@H]2[C@H](C1=O)[C@H]1CC[C@@H]2O1] | δ ppm 1.26 (d, 3H), 1.30 (d, 3H), 1.56-1.73 (m, 2H), 1.83-1.99 (m, 2H), 2.37 (s, 3H), 2.67-2.80 (m, 1H), 2.80 (d, 1H), 3.59 (d, 1H), 4.59 (d, 1H), 4.79 (d, 1H), 7.10 (s, 1H), 7.35 (d, 2H), 7.49 (d, 2H) |
| P3 | 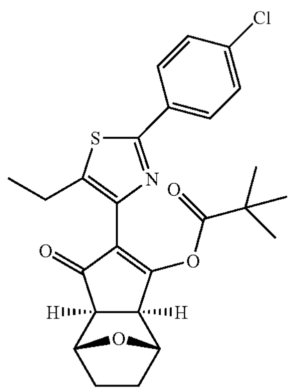 [SMILES: CCc1sc(-c2ccc(Cl)cc2)nc1C1=C(OC(=O)C(C)(C)C)[C@@H]2[C@H](C1=O)[C@H]1CC[C@@H]2O1] | δ ppm 1.20 (s, 9H), 1.30 (t, 3H), 1.56-1.69 (m, 2H), 1.81-1.94 (m, 2H), 2.74-2.80 (m, 3H), 3.50 (d, 1H), 4.57 (d, 1H), 4.77 (d, 1H), 7.36 (d, 2H), 7.80 (d, 2H) |
| P4 | 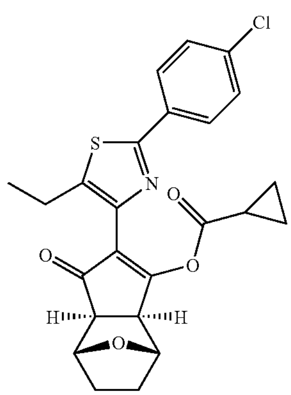 [SMILES: CCc1sc(-c2ccc(Cl)cc2)nc1C1=C(OC(=O)C2CC2)[C@@H]2[C@H](C1=O)[C@H]1CC[C@@H]2O1] | δ ppm 0.90-0.98 (m, 2H), 1.04-1.09 (m, 2H), 1.3 (t, 3H), 1.57-1.68 (m, 2H), 1.69-1.77 (m, 1H), 1.80-1.94 (m, 2H), 2.74-2.80 (m, 3H), 3.48 (d, 1H), 4.64 (d, 1H), 4.76 (d, 1H), 7.37 (d, 2H), 7.83 (d, 2H) |
| P5 | 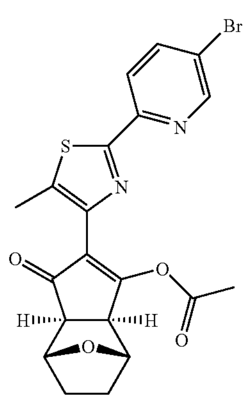 [SMILES: CC(=O)OC1=C(c2nc(-c3ccc(Br)cn3)sc2C)C(=O)[C@H]2[C@@H]1[C@@H]1CC[C@H]2O1] | δ ppm 1.57-1.63 (m, 2H), 1.80-1.94 (m, 2H), 2.21 (s, 3H), 2.41 (s, 3H), 2.76 (d, 1H), 3.46 (d, 1H), 4.62 (d, 1H), 4.76 (d, 1H), 7.86 (dd, 1H), 7.98 (d, 1H), 8.60 (d, 1H) |

TABLE P1-continued

| Compound Number | Structure | ¹H nmr (CDCl₃ unless stated) or other physical data |
|---|---|---|
| P6 | 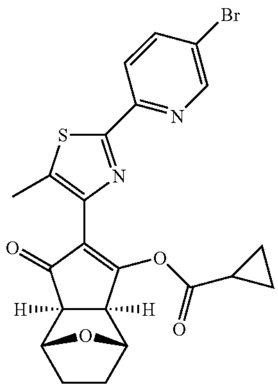 [SMILES: Cc1sc(-c2ccc(Br)cn2)nc1C1=C(OC(=O)C2CC2)[C@@H]2[C@H](C1=O)[C@H]1CC[C@@H]2O1] | δ ppm 0.90-0.98 (m, 2H), 1.04-1.09 (m, 2H), 1.57-1.68 (m, 2H), 1.69-1.77 (m, 1H), 1.80-1.94 (m, 2H), 2.41 (s, 3H), 2.76 (d, 1H), 3.52 (d, 1H), 4.63 (d, 1H), 4.76 (d, 1H), 7.86 (dd, 1H), 8.03 (d, 1H), 8.60 (d, 1H) |
| P7 | 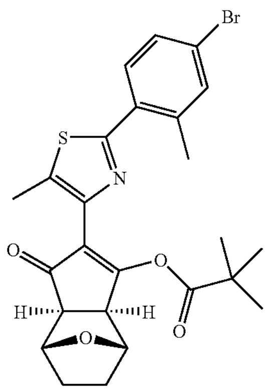 [SMILES: Cc1cc(Br)ccc1-c1nc(C2=C(OC(=O)C(C)(C)C)[C@@H]3[C@H](C2=O)[C@H]2CC[C@@H]3O2)c(C)s1] | δ ppm 1.19 (s, 9H), 1.57-1.68 (m, 2H), 1.80-1.94 (m, 2H), 2.41 (s, 3H), 2.52 (s, 3H), 2.77 (d, 1H), 3.49 (d, 1H), 4.55 (d, 1H), 4.77 (d, 1H), 7.35 (dd, 1H), 7.41 (d, 1H), 7.56 (d, 1H) |
| P8 | 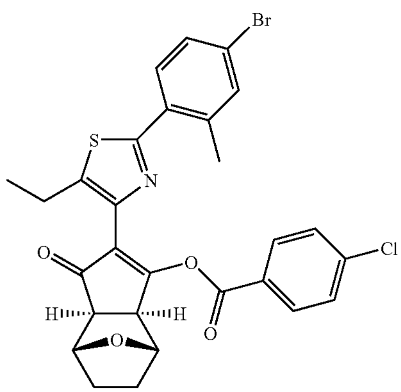 [SMILES: CCc1sc(-c2ccc(Br)cc2C)nc1C1=C(OC(=O)c2ccc(Cl)cc2)[C@@H]2[C@H](C1=O)[C@H]1CC[C@@H]2O1] | δ ppm 1.33 (t, 3H), 1.60-1.70 (m, 2H), 1.84-1.95 (m, 2H), 2.36 (s, 3H), 2.82-2.87 (m, 3H), 3.62 (d, 1H), 4.70 (d, 1H), 4.81 (d, 1H), 7.27 (d, 1H), 7.35-7.38 (m, 4H), 7.97 (d, 2H) |
| P9 | 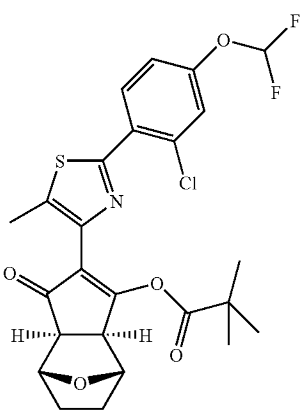 [SMILES: Cc1sc(-c2ccc(OC(F)F)cc2Cl)nc1C1=C(OC(=O)C(C)(C)C)[C@@H]2[C@H](C1=O)[C@H]1CC[C@@H]2O1] | δ ppm 1.20 (s, 9H), 1.59 - 1.68 (m, 2H), 1.77-2.00 (m, 2H), 2.42 (s, 3H), 2.78 (d, 1H), 3.52 (d, 1H), 4.57 (d, 1H), 4.78 (d, 1H), 6.55 (t, 1H), 7.08 (dd, 1H), 7.24 (d, 1H), 8.23 (d, 1H) |

TABLE P1-continued

| Compound Number | Structure | ¹H nmr (CDCl₃ unless stated) or other physical data |
|---|---|---|
| P10 | 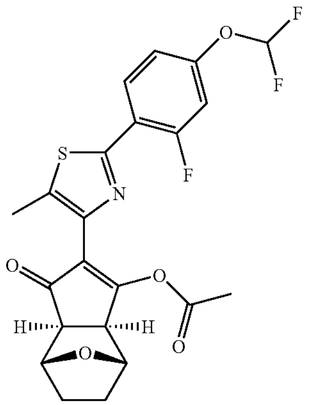 [SMILES: CC(=O)OC1=C(c2nc(-c3ccc(OC(F)F)cc3F)sc2C)C(=O)[C@H]2[C@@H]1[C@@H]1CC[C@H]2O1] | δ ppm 1.57-1.66 (m, 2H), 1.80-1.93 (m, 2H), 2.20 (s, 3H), 2.41 (s, 3H), 2.75 (d, 1H), 3.43 (d, 1H), 4.62 (d, 1H), 4.76 (d, 1H), 6.55 (t, 1H), 6.97 (m, 2H), 8.17 (d, 1H) |
| P11 | 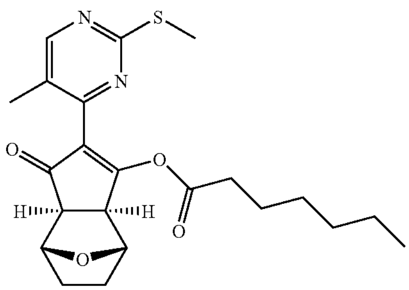 [SMILES: CCCCCCC(=O)OC1=C(c2nc(SC)ncc2C)C(=O)[C@H]2[C@@H]1[C@@H]1CC[C@H]2O1] | δ ppm 0.88 (t, 3H), 1.19-1.40 (m, 8H), 1.50-1.69 (m, 2H), 1.79-1.96 (m, 2H), 2.12 (s, 3H), 2.44 (t, 2H), 2.51 (s, 3H), 2.74 (d, 1H), 3.40 (d, 1H), 4.59 (d, 1H), 4.76 (d, 1H), 8.38 (s, 1H) |
| P12 | 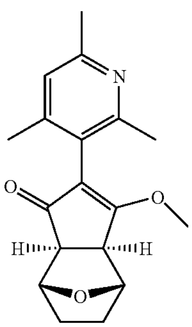 | δ ppm 1.56-1.66 (m, 2H), 1.77-1.96 (m, 2H), 2.11 (d, 3H), 2.36 (d, 3H), 2.47 (s, 3H), 2.68 (t, 1H), 2.93 (t, 1H), 3.62 (s, 3H), 4.67 (dd, 1H), 4.73 (t, 1H), 6.86 (d, 1H) |
| P13 | 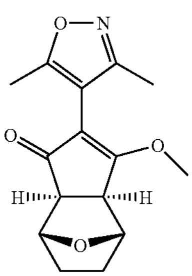 [SMILES: COC1=C(c2c(C)noc2C)C(=O)[C@H]2[C@@H]1[C@@H]1CC[C@H]2O1] | δ ppm 1.49-1.68 (m, 2H), 1.81-1.96 (m, 2H), 2.14 (s, 3H), 2.27 (s, 3H), 2.66 (d, 1H), 2.99 (d, 1H), 3.90 (s, 3H), 4.63 (d, 1H), 4.72 (d, 1H) |
| P14 | 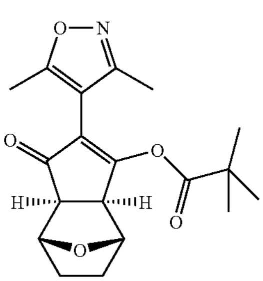 [SMILES: Cc1noc(C)c1C1=C(OC(=O)C(C)(C)C)[C@@H]2[C@H](C1=O)[C@H]1CC[C@@H]2O1] | δ ppm 1.27 (s, 9H), 1.58-1.65 (m, 2H), 1.80-1.93 (m, 2H), 2.14 (s, 3H), 2.26 (s, 3H), 2.75 (d, 1H), 3.54 (d, 1H), 4.48 (d, 1H), 4.71 (d, 1H) |

Specific examples of the compounds of the invention include those compounds detailed in Tables 1 to 360.

TABLE 1

This table covers 272 compounds of the structural type T-1:

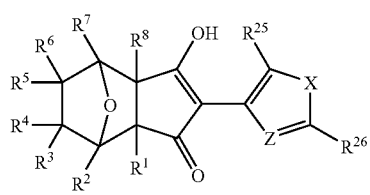

T-1 wherein X is S, Z is
C—H, $R^1$, $R^2$, $R^3$, $R^4$, $R^5$, $R^6$, $R^7$ and $R^8$ are hydrogen

| Compound Number | $R^{25}$ | $R^{26}$ |
|---|---|---|
| 1.001 | $CH_3$ | H |
| 1.002 | $CH_3$ | Cl |
| 1.003 | $CH_3$ | Br |
| 1.004 | $CH_3$ | $CH_3$ |
| 1.005 | $CH_3$ | $CH_3CH_2$ |
| 1.006 | $CH_3$ | $(CH_3)_2CH$ |
| 1.007 | $CH_3$ | $(CH_3)_3C$ |
| 1.008 | $CH_3CH_2$ | H |
| 1.009 | $CH_3CH_2$ | Cl |
| 1.010 | $CH_3CH_2$ | Br |
| 1.011 | $CH_3CH_2$ | $CH_3$ |
| 1.012 | $CH_3CH_2$ | $CH_3CH_2$ |
| 1.013 | $CH_3CH_2$ | $(CH_3)_2CH$ |
| 1.014 | $CH_3CH_2$ | $(CH_3)_3C$ |
| 1.015 | $CH_3$ | Phenyl |
| 1.016 | $CH_3$ | 2-fluorophenyl |
| 1.017 | $CH_3$ | 3-fluorophenyl |
| 1.018 | $CH_3$ | 4-fluorophenyl |
| 1.019 | $CH_3$ | 2-chlorophenyl |
| 1.020 | $CH_3$ | 3-chlorophenyl |
| 1.021 | $CH_3$ | 4-chlorophenyl |
| 1.022 | $CH_3$ | 2-bromophenyl |
| 1.023 | $CH_3$ | 3-bromophenyl |
| 1.024 | $CH_3$ | 4-bromophenyl |
| 1.025 | $CH_3$ | 2-iodophenyl |
| 1.026 | $CH_3$ | 3-iodophenyl |
| 1.027 | $CH_3$ | 4-iodophenyl |
| 1.028 | $CH_3$ | 2-methylphenyl |
| 1.029 | $CH_3$ | 3-methylphenyl |
| 1.030 | $CH_3$ | 4-methylphenyl |
| 1.031 | $CH_3$ | 2-cyanophenyl |
| 1.032 | $CH_3$ | 3-cyanophenyl |
| 1.033 | $CH_3$ | 4-cyanophenyl |
| 1.034 | $CH_3$ | 2-methoxyphenyl |
| 1.035 | $CH_3$ | 3-methoxyphenyl |
| 1.036 | $CH_3$ | 4-methoxyphenyl |
| 1.037 | $CH_3$ | 2-trifluoromethylphenyl |
| 1.038 | $CH_3$ | 3-trifluoromethylphenyl |
| 1.039 | $CH_3$ | 4-trifluoromethylphenyl |
| 1.040 | $CH_3$ | 4-trifluoromethoxyphenyl |
| 1.041 | $CH_3$ | 4-difluoromethoxyphenyl |
| 1.042 | $CH_3$ | 4-methylthiophenyl |
| 1.043 | $CH_3$ | 4-methylsulfinylphenyl |
| 1.044 | $CH_3$ | 4-methylsulfonylphenyl |
| 1.045 | $CH_3$ | 4-trifluoromethylthiophenyl |
| 1.046 | $CH_3$ | 4-trifluoromethylsulfinylphenyl |
| 1.047 | $CH_3$ | 4-trifluoromethylsulfonylphenyl |
| 1.048 | $CH_3$ | 2,3-difluorophenyl |
| 1.049 | $CH_3$ | 2,4-difluorophenyl |
| 1.050 | $CH_3$ | 2,5-difluorophenyl |
| 1.051 | $CH_3$ | 2,6-difluorophenyl |
| 1.052 | $CH_3$ | 3,4-difluorophenyl |
| 1.053 | $CH_3$ | 3,5-difluorophenyl |
| 1.054 | $CH_3$ | 2,3-dichlorophenyl |
| 1.055 | $CH_3$ | 2,4-dichlorophenyl |
| 1.056 | $CH_3$ | 2,5-dichlorophenyl |
| 1.057 | $CH_3$ | 2,6-dichlorophenyl |
| 1.058 | $CH_3$ | 3,4-dichlorophenyl |

TABLE 1-continued

This table covers 272 compounds of the structural type T-1:

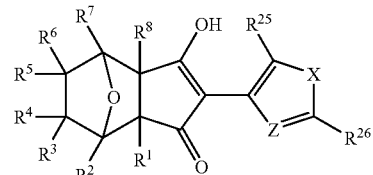

T-1 wherein X is S, Z is
C—H, $R^1$, $R^2$, $R^3$, $R^4$, $R^5$, $R^6$, $R^7$ and $R^8$ are hydrogen

| Compound Number | $R^{25}$ | $R^{26}$ |
|---|---|---|
| 1.059 | $CH_3$ | 3,5-dichlorophenyl |
| 1.060 | $CH_3$ | 2,3,4-trichlorophenyl |
| 1.061 | $CH_3$ | 2,3,5-trichlorophenyl |
| 1.062 | $CH_3$ | 2,3,6-trichlorophenyl |
| 1.063 | $CH_3$ | 2,4,5-trichlorophenyl |
| 1.064 | $CH_3$ | 2,4,6-trichlorophenyl |
| 1.065 | $CH_3$ | 3,4,5-trichlorophenyl |
| 1.066 | $CH_3$ | 4-bromo-2-fluorophenyl |
| 1.067 | $CH_3$ | 4-bromo-3-fluorophenyl |
| 1.068 | $CH_3$ | 4-bromo-2-chlorophenyl |
| 1.069 | $CH_3$ | 4-bromo-3-chlorophenyl |
| 1.070 | $CH_3$ | 4-bromo-2-cyanophenyl |
| 1.071 | $CH_3$ | 4-bromo-3-cyanophenyl |
| 1.072 | $CH_3$ | 4-bromo-2-methoxyphenyl |
| 1.073 | $CH_3$ | 4-bromo-3-methoxyphenyl |
| 1.074 | $CH_3$ | 4-bromo-2-methylphenyl |
| 1.075 | $CH_3$ | 4-bromo-3-methylphenyl |
| 1.076 | $CH_3$ | 4-chloro-2-cyanophenyl |
| 1.077 | $CH_3$ | 4-chloro-3-cyanophenyl |
| 1.078 | $CH_3$ | 4-chloro-2-fluorophenyl |
| 1.079 | $CH_3$ | 4-chloro-3-fluorophenyl |
| 1.080 | $CH_3$ | 4-chloro-2-methoxyphenyl |
| 1.081 | $CH_3$ | 4-chloro-3-methoxyphenyl |
| 1.082 | $CH_3$ | 4-chloro-2-methylphenyl |
| 1.083 | $CH_3$ | 4-chloro-3-methylphenyl |
| 1.084 | $CH_3$ | 4-chloro-2-trifluoromethylphenyl |
| 1.085 | $CH_3$ | 4-chloro-3-trifluoromethylphenyl |
| 1.086 | $CH_3$ | 2-chloro-4-methoxyphenyl |
| 1.087 | $CH_3$ | 3-chloro-4-methoxyphenyl |
| 1.088 | $CH_3$ | 2-chloro-4-methylphenyl |
| 1.089 | $CH_3$ | 3-chloro-4-methylphenyl |
| 1.090 | $CH_3$ | 4-fluoro-2-chlorophenyl |
| 1.091 | $CH_3$ | 4-fluoro-3-chlorophenyl |
| 1.092 | $CH_3$ | 4-fluoro-2-methylphenyl |
| 1.093 | $CH_3$ | 4-fluoro-3-methylphenyl |
| 1.094 | $CH_3$ | 4-fluoro-2-trifluoromethylphenyl |
| 1.095 | $CH_3$ | 4-fluoro-3-trifluoromethylphenyl |
| 1.096 | $CH_3$ | 2-fluoro-4-methoxyphenyl |
| 1.097 | $CH_3$ | 3-fluoro-4-methoxyphenyl |
| 1.098 | $CH_3$ | 2-fluoro-4-methylphenyl |
| 1.099 | $CH_3$ | 2-fluoro-4-methylphenyl |
| 1.100 | $CH_3$ | 2-fluoro-4-trifluoromethylphenyl |
| 1.101 | $CH_3$ | 3-fluoro-4-trifluoromethylphenyl |
| 1.102 | $CH_3$ | 2-pyridyl |
| 1.103 | $CH_3$ | 3-pyridyl |
| 1.104 | $CH_3$ | 4-pyridyl |
| 1.105 | $CH_3$ | 3-chloropyridin-2-yl |
| 1.106 | $CH_3$ | 4-chloropyridin-2-yl |
| 1.107 | $CH_3$ | 5-chloropyridin-2-yl |
| 1.108 | $CH_3$ | 6-chloropyridin-2-yl |
| 1.109 | $CH_3$ | 2-chloropyridin-3-yl |
| 1.110 | $CH_3$ | 4-chloropyridin-3-yl |
| 1.111 | $CH_3$ | 2-chloropyridin-4-yl |
| 1.112 | $CH_3$ | 3-chloropyridin-4-yl |
| 1.113 | $CH_3$ | 2-chloropyridin-5-yl |
| 1.114 | $CH_3$ | 3-chloropyridin-5-yl |
| 1.115 | $CH_3$ | 3-methylpyridin-2-yl |
| 1.116 | $CH_3$ | 4-methylpyridin-2-yl |
| 1.117 | $CH_3$ | 5-methylpyridin-2-yl |
| 1.118 | $CH_3$ | 6-methylpyridin-2-yl |
| 1.119 | $CH_3$ | 2-methylpyridin-3-yl |
| 1.120 | $CH_3$ | 4-methylpyridin-3-yl |

TABLE 1-continued

This table covers 272 compounds of the structural type T-1:

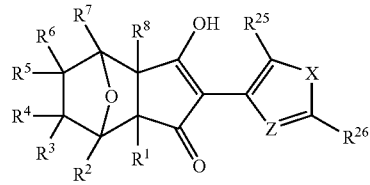

wherein X is S, Z is C—H, $R^1$, $R^2$, $R^3$, $R^4$, $R^5$, $R^6$, $R^7$ and $R^8$ are hydrogen

| Compound Number | $R^{25}$ | $R^{26}$ |
|---|---|---|
| 1.121 | $CH_3$ | 2-methylpyridin-4-yl |
| 1.122 | $CH_3$ | 3-methylpyridin-4-yl |
| 1.123 | $CH_3$ | 2-methylpyridin-5-yl |
| 1.124 | $CH_3$ | 3-methylpyridinyl-5-yl |
| 1.125 | $CH_3$ | 2-trifluoromethylpyridin-5-yl |
| 1.126 | $CH_3$ | 3-trifluoromethylpyridin-5-yl |
| 1.127 | $CH_3$ | 2,6-dichloropyridin-3-yl |
| 1.128 | $CH_3$ | 2-chloro-4-methylpyridin-5-yl |
| 1.129 | $CH_3$ | 6-chloro-2-methylpyridin-3-yl |
| 1.130 | $CH_3$ | 3,4-methylenedioxyphenyl |
| 1.131 | $CH_3$ | benzo[1,3]diox-5-yl |
| 1.132 | $CH_3$ | 2,3-dihydrobenzo[1,4]dioxin-6-yl |
| 1.133 | $CH_3$ | 4-chloropyrazol-1-yl |
| 1.134 | $CH_3$ | 2-thiophenyl |
| 1.135 | $CH_3$ | 5-chlorothiophen-2-yl |
| 1.136 | $CH_3$ | 5-bromothiophen-2-yl |
| 1.137 | $CH_3$ | 3-thiophenyl |
| 1.138 | $CH_3$ | 5-chlorothiophen-3-yl |
| 1.139 | $CH_3$ | 5-bromothiophen-3-yl |
| 1.140 | $CH_3$ | 5-chloro-thiazolyl |
| 1.141 | $CH_3$ | 5-bromo-thiazolyl |
| 1.142 | $CH_3$ | 2-chloro-thiazolyl |
| 1.143 | $CH_3$ | 2-bromo-thiazolyl |
| 1.144 | $CH_3CH_2$ | Phenyl |
| 1.145 | $CH_3CH_2$ | 2-fluorophenyl |
| 1.146 | $CH_3CH_2$ | 3-fluorophenyl |
| 1.147 | $CH_3CH_2$ | 4-fluorophenyl |
| 1.148 | $CH_3CH_2$ | 2-chlorophenyl |
| 1.149 | $CH_3CH_2$ | 3-chlorophenyl |
| 1.150 | $CH_3CH_2$ | 4-chlorophenyl |
| 1.151 | $CH_3CH_2$ | 2-bromophenyl |
| 1.152 | $CH_3CH_2$ | 3-bromophenyl |
| 1.153 | $CH_3CH_2$ | 4-bromophenyl |
| 1.154 | $CH_3CH_2$ | 2-iodophenyl |
| 1.155 | $CH_3CH_2$ | 3-iodophenyl |
| 1.156 | $CH_3CH_2$ | 4-iodophenyl |
| 1.157 | $CH_3CH_2$ | 2-methylphenyl |
| 1.158 | $CH_3CH_2$ | 3-methylphenyl |
| 1.159 | $CH_3CH_2$ | 4-methylphenyl |
| 1.160 | $CH_3CH_2$ | 2-cyanophenyl |
| 1.161 | $CH_3CH_2$ | 3-cyanophenyl |
| 1.162 | $CH_3CH_2$ | 4-cyanophenyl |
| 1.163 | $CH_3CH_2$ | 2-methoxyphenyl |
| 1.164 | $CH_3CH_2$ | 3-methoxyphenyl |
| 1.165 | $CH_3CH_2$ | 4-methoxyphenyl |
| 1.166 | $CH_3CH_2$ | 2-trifluoromethylphenyl |
| 1.167 | $CH_3CH_2$ | 3-trifluoromethylphenyl |
| 1.168 | $CH_3CH_2$ | 4-trifluoromethylphenyl |
| 1.169 | $CH_3CH_2$ | 4-trifluoromethoxyphenyl |
| 1.170 | $CH_3CH_2$ | 4-difluoromethoxyphenyl |
| 1.171 | $CH_3CH_2$ | 4-methylthiophenyl |
| 1.172 | $CH_3CH_2$ | 4-methylsulfinylphenyl |
| 1.173 | $CH_3CH_2$ | 4-methylsulfonylphenyl |
| 1.174 | $CH_3CH_2$ | 4-trifluoromethylthiophenyl |
| 1.175 | $CH_3CH_2$ | 4-trifluoromethylsulfinylphenyl |
| 1.176 | $CH_3CH_2$ | 4-trifluoromethylsulfonylphenyl |
| 1.177 | $CH_3CH_2$ | 2,3-difluorophenyl |
| 1.178 | $CH_3CH_2$ | 2,4-difluorophenyl |
| 1.179 | $CH_3CH_2$ | 2,5-difluorophenyl |
| 1.180 | $CH_3CH_2$ | 2,6-difluorophenyl |
| 1.181 | $CH_3CH_2$ | 3,4-difluorophenyl |
| 1.182 | $CH_3CH_2$ | 3,5-difluorophenyl |

TABLE 1-continued

This table covers 272 compounds of the structural type T-1:

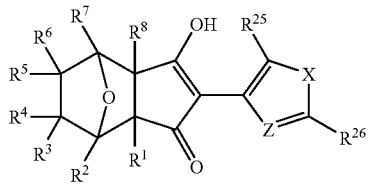

wherein X is S, Z is C—H, $R^1$, $R^2$, $R^3$, $R^4$, $R^5$, $R^6$, $R^7$ and $R^8$ are hydrogen

| Compound Number | $R^{25}$ | $R^{26}$ |
|---|---|---|
| 1.183 | $CH_3CH_2$ | 2,3-dichlorophenyl |
| 1.184 | $CH_3CH_2$ | 2,4-dichlorophenyl |
| 1.185 | $CH_3CH_2$ | 2,5-dichlorophenyl |
| 1.186 | $CH_3CH_2$ | 2,6-dichlorophenyl |
| 1.187 | $CH_3CH_2$ | 3,4-dichlorophenyl |
| 1.188 | $CH_3CH_2$ | 3,5-dichlorophenyl |
| 1.189 | $CH_3CH_2$ | 2,3,4-trichlorophenyl |
| 1.190 | $CH_3CH_2$ | 2,3,5-trichlorophenyl |
| 1.191 | $CH_3CH_2$ | 2,3,6-trichlorophenyl |
| 1.192 | $CH_3CH_2$ | 2,4,5-trichlorophenyl |
| 1.193 | $CH_3CH_2$ | 2,4,6-trichlorophenyl |
| 1.194 | $CH_3CH_2$ | 3,4,5-trichlorophenyl |
| 1.195 | $CH_3CH_2$ | 4-bromo-2-fluorophenyl |
| 1.196 | $CH_3CH_2$ | 4-bromo-3-fluorophenyl |
| 1.197 | $CH_3CH_2$ | 4-bromo-2-chlorophenyl |
| 1.198 | $CH_3CH_2$ | 4-bromo-3-chlorophenyl |
| 1.199 | $CH_3CH_2$ | 4-bromo-2-cyanophenyl |
| 1.200 | $CH_3CH_2$ | 4-bromo-3-cyanophenyl |
| 1.201 | $CH_3CH_2$ | 4-bromo-2-methoxyphenyl |
| 1.202 | $CH_3CH_2$ | 4-bromo-3-methoxyphenyl |
| 1.203 | $CH_3CH_2$ | 4-bromo-2-methylphenyl |
| 1.204 | $CH_3CH_2$ | 4-bromo-3-methylphenyl |
| 1.205 | $CH_3CH_2$ | 4-chloro-2-cyanophenyl |
| 1.206 | $CH_3CH_2$ | 4-chloro-3-cyanophenyl |
| 1.207 | $CH_3CH_2$ | 4-chloro-2-fluorophenyl |
| 1.208 | $CH_3CH_2$ | 4-chloro-3-fluorophenyl |
| 1.209 | $CH_3CH_2$ | 4-chloro-2-methoxyphenyl |
| 1.210 | $CH_3CH_2$ | 4-chloro-3-methoxyphenyl |
| 1.211 | $CH_3CH_2$ | 4-chloro-2-methylphenyl |
| 1.212 | $CH_3CH_2$ | 4-chloro-3-methylphenyl |
| 1.213 | $CH_3CH_2$ | 4-chloro-2-trifluoromethylphenyl |
| 1.214 | $CH_3CH_2$ | 4-chloro-3-trifluoromethylphenyl |
| 1.215 | $CH_3CH_2$ | 2-chloro-4-methoxyphenyl |
| 1.216 | $CH_3CH_2$ | 3-chloro-4-methoxyphenyl |
| 1.217 | $CH_3CH_2$ | 2-chloro-4-methylphenyl |
| 1.218 | $CH_3CH_2$ | 3-chloro-4-methylphenyl |
| 1.219 | $CH_3CH_2$ | 4-fluoro-2-chlorophenyl |
| 1.220 | $CH_3CH_2$ | 4-fluoro-3-chlorophenyl |
| 1.221 | $CH_3CH_2$ | 4-fluoro-2-methylphenyl |
| 1.222 | $CH_3CH_2$ | 4-fluoro-3-methylphenyl |
| 1.223 | $CH_3CH_2$ | 4-fluoro-2-trifluoromethylphenyl |
| 1.224 | $CH_3CH_2$ | 4-fluoro-3-trifluoromethylphenyl |
| 1.225 | $CH_3CH_2$ | 2-fluoro-4-methoxyphenyl |
| 1.226 | $CH_3CH_2$ | 3-fluoro-4-methoxyphenyl |
| 1.227 | $CH_3CH_2$ | 2-fluoro-4-methylphenyl |
| 1.228 | $CH_3CH_2$ | 2-fluoro-4-methylphenyl |
| 1.229 | $CH_3CH_2$ | 2-fluoro-4-trifluoromethylphenyl |
| 1.230 | $CH_3CH_2$ | 3-fluoro-4-trifluoromethylphenyl |
| 1.231 | $CH_3CH_2$ | 2-pyridyl |
| 1.232 | $CH_3CH_2$ | 3-pyridyl |
| 1.233 | $CH_3CH_2$ | 4-pyridyl |
| 1.234 | $CH_3CH_2$ | 3-chloropyridin-2-yl |
| 1.235 | $CH_3CH_2$ | 4-chloropyridin-2-yl |
| 1.236 | $CH_3CH_2$ | 5-chloropyridin-2-yl |
| 1.237 | $CH_3CH_2$ | 6-chloropyridin-2-yl |
| 1.238 | $CH_3CH_2$ | 2-chloropyridin-3-yl |
| 1.239 | $CH_3CH_2$ | 4-chloropyridin-3-yl |
| 1.240 | $CH_3CH_2$ | 2-chloropyridin-4-yl |
| 1.241 | $CH_3CH_2$ | 3-chloropyridin-4-yl |
| 1.242 | $CH_3CH_2$ | 2-chloropyridin-5-yl |
| 1.243 | $CH_3CH_2$ | 3-chloropyridin-5-yl |
| 1.244 | $CH_3CH_2$ | 3-methylpyridin-2-yl |

TABLE 1-continued

This table covers 272 compounds of the structural type T-1:

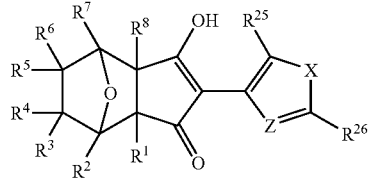

T-1 wherein X is S, Z is
C—H, $R^1, R^2, R^3, R^4, R^5, R^6, R^7$ and $R^8$ are hydrogen

| Compound Number | $R^{25}$ | $R^{26}$ |
|---|---|---|
| 1.245 | $CH_3CH_2$ | 4-methylpyridin-2-yl |
| 1.246 | $CH_3CH_2$ | 5-methylpyridin-2-yl |
| 1.247 | $CH_3CH_2$ | 6-methylpyridin-2-yl |
| 1.248 | $CH_3CH_2$ | 2-methylpyridin-3-yl |
| 1.249 | $CH_3CH_2$ | 4-methylpyridin-3-yl |
| 1.250 | $CH_3CH_2$ | 2-methylpyridin-4-yl |
| 1.251 | $CH_3CH_2$ | 3-methylpyridin-4-yl |
| 1.252 | $CH_3CH_2$ | 2-methylpyridin-5-yl |
| 1.253 | $CH_3CH_2$ | 3-methylpyridinyl-5-yl |
| 1.254 | $CH_3CH_2$ | 2-trifluoromethylpyridin-5-yl |
| 1.255 | $CH_3CH_2$ | 3-trifluoromethylpyridin-5-yl |
| 1.256 | $CH_3CH_2$ | 2,6-dichloropyridin-3-yl |
| 1.257 | $CH_3CH_2$ | 2-chloro-4-methylpyridin-5-yl |
| 1.258 | $CH_3CH_2$ | 6-chloro-2-methylpyridin-3-yl |
| 1.259 | $CH_3CH_2$ | 3,4-methylenedioxyphenyl |
| 1.260 | $CH_3CH_2$ | benzo[1,3]diox-5-yl |
| 1.261 | $CH_3CH_2$ | 2,3-dihydrobenzo[1,4]dioxin-6-yl |
| 1.262 | $CH_3CH_2$ | 4-chloropyrazol-1-yl |
| 1.263 | $CH_3CH_2$ | 2-thiophenyl |
| 1.264 | $CH_3CH_2$ | 5-chlorothiophen-2-yl |
| 1.265 | $CH_3CH_2$ | 5-bromothiophen-2-yl |
| 1.266 | $CH_3CH_2$ | 3-thiophenyl |
| 1.267 | $CH_3CH_2$ | 5-chlorothiophen-3-yl |
| 1.268 | $CH_3CH_2$ | 5-bromothiophen-3-yl |
| 1.269 | $CH_3CH_2$ | 5-chloro-thiazolyl |
| 1.270 | $CH_3CH_2$ | 5-bromo-thiazolyl |
| 1.271 | $CH_3CH_2$ | 2-chloro-thiazolyl |
| 1.272 | $CH_3CH_2$ | 2-bromo-thiazolyl |

Table 2:
This table covers 272 compounds of the structural type T-1, wherein X is S, Z is C—H, $R^7$ is $CH_3$, $R^1, R^2, R^3, R^4, R^5, R^6$ and $R^8$ are hydrogen and $R^{25}$ and $R^{26}$ are as defined in Table 1.

Table 3:
This table covers 272 compounds of the structural type T-1, wherein X is S, Z is C—H, $R^7$ is $CH_2CH_3$, $R^1, R^2, R^3, R^4, R^5, R^6$ and $R^8$ are hydrogen and $R^{25}$ and $R^{26}$ are as defined in Table 1.

Table 4:
This table covers 272 compounds of the structural type T-1, wherein X is S, Z is C—H, $R^7$ is cyclopropyl $R^1, R^2, R^3, R^4, R^5, R^6$ and $R^8$ are hydrogen and $R^{25}$ and $R^{26}$ are as defined in Table 1.

Table 5:
This table covers 272 compounds of the structural type T-1, wherein X is S, Z is C—H, $R^7$ is $CH_2OCH_3$, $R^1, R^2, R^3, R^4, R^5, R^6$ and $R^8$ are hydrogen and $R^{25}$ and $R^{26}$ are as defined in Table 1.

Table 6:
This table covers 272 compounds of the structural type T-1, wherein X is S, Z is C—H, $R^7$ is $CH_2OCH_2CH_3$, $R^1, R^2, R^3, R^4, R^5, R^6$ and $R^8$ are hydrogen and $R^{25}$ and $R^{26}$ are as defined in Table 1.

Table 7:
This table covers 272 compounds of the structural type T-1, wherein X is S, Z is C—H, $R^7$ is $CH_2CH_2OCH_3$, $R^1, R^2, R^3, R^4, R^5, R^6$ and $R^8$ are hydrogen and $R^{25}$ and $R^{26}$ are as defined in Table 1.

Table 8:
This table covers 272 compounds of the structural type T-1, wherein X is S, Z is C—H, $R^7$ is $OCH_3$, $R^1, R^2, R^3, R^4, R^5, R^6$ and $R^8$ are hydrogen and $R^{25}$ and $R^{26}$ are as defined in Table 1.

Table 9:
This table covers 272 compounds of the structural type T-1, wherein X is S, Z is C—H, $R^7$ is $OCH_2CH_3$, $R^1, R^2, R^3, R^4, R^5, R^6$ and $R^8$ are hydrogen and $R^{25}$ and $R^{26}$ are as defined in Table 1.

Table 10:
This table covers 272 compounds of the structural type T-1, wherein X is S, Z is C—H, $R^7$ and $R^2$ are $CH_3$, $R^1, R^3, R^4, R^5, R^6$ and $R^8$ are hydrogen and $R^{25}$ and $R^{26}$ are as defined in Table 1.

Table 11:
This table covers 272 compounds of the structural type T-1, wherein X is S, Z is C—H, $R^6$ is $CH_3$, $R^1, R^2, R^3, R^4, R^5, R^7$ and $R^8$ are hydrogen and $R^{25}$ and $R^{26}$ are as defined in Table 1.

Table 12:
This table covers 272 compounds of the structural type T-1, wherein X is S, Z is C—H, $R^6$ is $CH_2CH_3$, $R^1, R^2, R^3, R^4, R^5, R^7$ and $R^8$ are hydrogen and $R^{25}$ and $R^{26}$ are as defined in Table 1.

Table 13:
This table covers 272 compounds of the structural type T-1, wherein X is S, Z is C—H, $R^6$ is $CH_2OCH_3$, $R^1, R^2, R^3, R^4, R^5, R^7$ and $R^8$ are hydrogen and $R^{25}$ and $R^{26}$ are as defined in Table 1.

Table 14:
This table covers 272 compounds of the structural type T-1, wherein X is S, Z is C—H, $R^6$ is $CH_2OCH_2CH_3$, $R^1, R^2, R^3, R^4, R^5, R^7$ and $R^8$ are hydrogen and $R^{25}$ and $R^{26}$ are as defined in Table 1.

Table 15:
This table covers 272 compounds of the structural type T-1, wherein X is S, Z is C—H, $R^6$ is $CH_2CH_2OCH_3$, $R^1, R^2, R^3, R^4, R^5, R^7$ and $R^8$ are hydrogen and $R^{25}$ and $R^{26}$ are as defined in Table 1.

Table 16:
This table covers 272 compounds of the structural type T-1, wherein X is S, Z is C—$CH_3$, $R^1, R^2, R^3, R^4, R^5, R^6, R^7$ and $R^8$ are hydrogen Table 17:
This table covers 272 compounds of the structural type T-1, wherein X is S, Z is C—$CH_3$, $R^7$ is $CH_3$, $R^1, R^2, R^3, R^4, R^5, R^6$ and $R^8$ are hydrogen and $R^{25}$ and $R^{26}$ are as defined in Table 1.

Table 18:
This table covers 272 compounds of the structural type T-1, wherein X is S, Z is C—$CH_3$, $R^7$ is $CH_2CH_3$, $R^1, R^2, R^3, R^4, R^5, R^6$ and $R^8$ are hydrogen and $R^{25}$ and $R^{26}$ are as defined in Table 1.

Table 19:
This table covers 272 compounds of the structural type T-1, wherein X is S, Z is C—$CH_3$, $R^7$ is cyclopropyl, $R^1, R^2, R^3, R^4, R^5, R^6$ and $R^8$ are hydrogen and $R^{25}$ and $R^{26}$ are as defined in Table 1.

Table 20:
This table covers 272 compounds of the structural type T-1, wherein X is S, Z is C—CH$_3$, R$^7$ is CH$_2$OCH$_3$, R$^1$, R$^2$, R$^3$, R$^4$, R$^5$, R$^6$ and R$^8$ are hydrogen and R$^{25}$ and R$^{26}$ are as defined in Table 1.

Table 21:
This table covers 272 compounds of the structural type T-1, wherein X is S, Z is C—CH$_3$, R$^7$ is CH$_2$OCH$_2$CH$_3$, R$^1$, R$^2$, R$^3$, R$^4$, R$^5$, R$^6$ and R$^8$ are hydrogen and R$^{25}$ and R$^{26}$ are as defined in Table 1.

Table 22:
This table covers 272 compounds of the structural type T-1, wherein X is S, Z is C—CH$_3$, R$^7$ is CH$_2$CH$_2$OCH$_3$, R$^1$, R$^2$, R$^3$, R$^4$, R$^5$, R$^6$ and R$^8$ are hydrogen and R$^{25}$ and R$^{26}$ are as defined in Table 1.

Table 23:
This table covers 272 compounds of the structural type T-1, wherein X is S, Z is C—CH$_3$, R$^7$ is OCH$_3$, R$^1$, R$^2$, R$^3$, R$^4$, R$^5$, R$^6$ and R$^8$ are hydrogen and R$^{25}$ and R$^{26}$ are as defined in Table 1.

Table 24:
This table covers 272 compounds of the structural type T-1, wherein X is S, Z is C—CH$_3$, R$^7$ is OCH$_2$CH$_3$, R$^1$, R$^2$, R$^3$, R$^4$, R$^5$, R$^6$ and R$^8$ are hydrogen and R$^{25}$ and R$^{26}$ are as defined in Table 1.

Table 25:
This table covers 272 compounds of the structural type T-1, wherein X is S, Z is C—CH$_3$, R$^7$ and R$^2$ are CH$_3$, R$^1$, R$^3$, R$^4$, R$^5$, R$^6$ and R$^8$ are hydrogen and R$^{25}$ and R$^{26}$ are as defined in Table 1.

Table 26:
This table covers 272 compounds of the structural type T-1, wherein X is S, Z is C—CH$_3$, R$^6$ is CH$_3$, R$^1$, R$^2$, R$^3$, R$^4$, R$^5$, R$^7$ and R$^8$ are hydrogen and R$^{25}$ and R$^{26}$ are as defined in Table 1.

Table 27:
This table covers 272 compounds of the structural type T-1, wherein X is S, Z is C—CH$_3$, R$^6$ is CH$_2$CH$_3$, R$^1$, R$^2$, R$^3$, R$^4$, R$^5$, R$^7$ and R$^8$ are hydrogen and R$^{25}$ and R$^{26}$ are as defined in Table 1.

Table 28:
This table covers 272 compounds of the structural type T-1, wherein X is S, Z is C—CH$_3$, R$^6$ is CH$_2$OCH$_3$, R$^1$, R$^2$, R$^3$, R$^4$, R$^5$, R$^7$ and R$^8$ are hydrogen and R$^{25}$ and R$^{26}$ are as defined in Table 1.

Table 29:
This table covers 272 compounds of the structural type T-1, wherein X is S, Z is C—CH$_3$, R$^6$ is CH$_2$OCH$_2$CH$_3$, R$^1$, R$^2$, R$^3$, R$^4$, R$^5$, R$^7$ and R$^8$ are hydrogen and R$^{25}$ and R$^{26}$ are as defined in Table 1.

Table 30:
This table covers 272 compounds of the structural type T-1, wherein X is S, Z is C—CH$_3$, R$^6$ is CH$_2$CH$_2$OCH$_3$, R$^1$, R$^2$, R$^3$, R$^4$, R$^5$, R$^7$ and R$^8$ are hydrogen and R$^{25}$ and R$^{26}$ are as defined in Table 1.

Table 31:
This table covers 272 compounds of the structural type T-1, wherein X is S, Z is C—CH$_2$CH$_3$, R$^1$, R$^2$, R$^3$, R$^4$, R$^5$, R$^6$, R$^7$ and R$^8$ are hydrogen.

Table 32:
This table covers 272 compounds of the structural type T-1, wherein X is S, Z is C—CH$_2$CH$_3$, R$^7$ is CH$_3$, R$^1$, R$^2$, R$^3$, R$^4$, R$^5$, R$^6$ and R$^8$ are hydrogen and R$^{25}$ and R$^{26}$ are as defined in Table 1.

Table 33:
This table covers 272 compounds of the structural type T-1, wherein X is S, Z is C—CH$_2$CH$_3$, R$^7$ is CH$_2$CH$_3$, R$^1$, R$^2$, R$^3$, R$^4$, R$^5$, R$^6$ and R$^8$ are hydrogen and R$^{25}$ and R$^{26}$ are as defined in Table 1.

Table 34:
This table covers 272 compounds of the structural type T-1, wherein X is S, Z is C—CH$_2$CH$_3$, R$^7$ is cyclopropyl, R$^1$, R$^2$, R$^3$, R$^4$, R$^5$, R$^6$ and R$^8$ are hydrogen and R$^{25}$ and R$^{26}$ are as defined in Table 1.

Table 35:
This table covers 272 compounds of the structural type T-1, wherein X is S, Z is C—CH$_2$CH$_3$, R$^7$ is CH$_2$OCH$_3$, R$^1$, R$^2$, R$^3$, R$^4$, R$^5$, R$^6$ and R$^8$ are hydrogen and R$^{25}$ and R$^{26}$ are as defined in Table 1.

Table 36:
This table covers 272 compounds of the structural type T-1, wherein X is S, Z is C—CH$_2$CH$_3$, R$^7$ is CH$_2$OCH$_2$CH$_3$, R$^1$, R$^2$, R$^3$, R$^4$, R$^5$, R$^6$ and R$^8$ are hydrogen and R$^{25}$ and R$^{26}$ are as defined in Table 1.

Table 37:
This table covers 272 compounds of the structural type T-1, wherein X is S, Z is C—CH$_2$CH$_3$, R$^7$ is CH$_2$CH$_2$OCH$_3$, R$^1$, R$^2$, R$^3$, R$^4$, R$^5$, R$^6$ and R$^8$ are hydrogen and R$^{25}$ and R$^{26}$ are as defined in Table 1.

Table 38:
This table covers 272 compounds of the structural type T-1, wherein X is S, Z is C—CH$_2$CH$_3$, R$^7$ is OCH$_3$, R$^1$, R$^2$, R$^3$, R$^4$, R$^5$, R$^6$ and R$^8$ are hydrogen and R$^{25}$ and R$^{26}$ are as defined in Table 1.

Table 39:
This table covers 272 compounds of the structural type T-1, wherein X is S, Z is C—CH$_2$CH$_3$, R$^7$ is OCH$_2$CH$_3$, R$^1$, R$^2$, R$^3$, R$^4$, R$^5$, R$^6$ and R$^8$ are hydrogen and R$^{25}$ and R$^{26}$ are as defined in Table 1.

Table 40:
This table covers 272 compounds of the structural type T-1, wherein X is S, Z is C—CH$_2$CH$_3$, R$^7$ and R$^2$ are CH$_3$, R$^1$, R$^3$, R$^4$, R$^5$, R$^6$ and R$^8$ are hydrogen and R$^{25}$ and R$^{26}$ are as defined in Table 1.

Table 41:
This table covers 272 compounds of the structural type T-1, wherein X is S, Z is C—CH$_2$CH$_3$, R$^6$ is CH$_3$, R$^1$, R$^2$, R$^3$, R$^4$, R$^5$, R$^7$ and R$^8$ are hydrogen and R$^{25}$ and R$^{26}$ are as defined in Table 1.

Table 42:
This table covers 272 compounds of the structural type T-1, wherein X is S, Z is C—CH$_2$CH$_3$, R$^6$ is CH$_2$CH$_3$, R$^1$, R$^2$, R$^3$, R$^4$, R$^5$, R$^7$ and R$^8$ are hydrogen and R$^{25}$ and R$^{26}$ are as defined in Table 1.

Table 43:
This table covers 272 compounds of the structural type T-1, wherein X is S, Z is C—CH$_2$CH$_3$, R$^6$ is CH$_2$OCH$_3$, R$^1$, R$^2$, R$^3$, R$^4$, R$^5$, R$^7$ and R$^8$ are hydrogen and R$^{25}$ and R$^{26}$ are as defined in Table 1.

Table 44:
This table covers 272 compounds of the structural type T-1, wherein X is S, Z is C—CH$_2$CH$_3$, R$^6$ is CH$_2$OCH$_2$CH$_3$, R$^1$, R$^2$, R$^3$, R$^4$, R$^5$, R$^7$ and R$^8$ are hydrogen and R$^{25}$ and R$^{26}$ are as defined in Table 1.

Table 45:
This table covers 272 compounds of the structural type T-1, wherein X is S, Z is C—CH$_2$CH$_3$, R$^6$ is CH$_2$CH$_2$OCH$_3$, R$^1$, R$^2$, R$^3$, R$^4$, R$^5$, R$^7$ and R$^8$ are hydrogen and R$^{25}$ and R$^{26}$ are as defined in Table 1.

Table 46:
This table covers 272 compounds of the structural type T-1, wherein X is S, Z is N, $R^1, R^2, R^3, R^4, R^5, R^6, R^7$ and $R^8$ are hydrogen
Table 47:
This table covers 272 compounds of the structural type T-1, wherein X is S, Z is N, $R^7$ is $CH_3$, $R^1, R^2, R^3, R^4, R^5, R^6$ and $R^8$ are hydrogen and $R^{25}$ and $R^{26}$ are as defined in Table 1.
Table 48:
This table covers 272 compounds of the structural type T-1, wherein X is S, Z is N, $R^7$ is $CH_2CH_3$, $R^1, R^2, R^3, R^4, R^5, R^6$ and $R^8$ are hydrogen and $R^{25}$ and $R^{26}$ are as defined in Table 1.
Table 49:
This table covers 272 compounds of the structural type T-1, wherein X is S, Z is N, $R^7$ is cyclopropyl, $R^1, R^2, R^3, R^4, R^5, R^6$ and $R^8$ are hydrogen and $R^{25}$ and $R^{26}$ are as defined in Table 1.
Table 50:
This table covers 272 compounds of the structural type T-1, wherein X is S, Z is N, $R^7$ is $CH_2OCH_3$, $R^1, R^2, R^3, R^4, R^5, R^6$ and $R^8$ are hydrogen and $R^{25}$ and $R^{26}$ are as defined in Table 1.
Table 51:
This table covers 272 compounds of the structural type T-1, wherein X is S, Z is N, $R^7$ is $CH_2OCH_2CH_3$, $R^1, R^2, R^3, R^4, R^5, R^6$ and $R^8$ are hydrogen and $R^{25}$ and $R^{26}$ are as defined in Table 1.
Table 52:
This table covers 272 compounds of the structural type T-1, wherein X is S, Z is N, $R^7$ is $CH_2CH_2OCH_3$, $R^1, R^2, R^3, R^4, R^5, R^6$ and $R^8$ are hydrogen and $R^{25}$ and $R^{26}$ are as defined in Table 1.
Table 53:
This table covers 272 compounds of the structural type T-1, wherein X is S, Z is N, $R^7$ is $OCH_3$, $R^1, R^2, R^3, R^4, R^5, R^6$ and $R^8$ are hydrogen and $R^{25}$ and $R^{26}$ are as defined in Table 1.
Table 54:
This table covers 272 compounds of the structural type T-1, wherein X is S, Z is N, $R^7$ is $OCH_2CH_3$, $R^1, R^2, R^3, R^4, R^5, R^6$ and $R^8$ are hydrogen and $R^{25}$ and $R^{26}$ are as defined in Table 1.
Table 55:
This table covers 272 compounds of the structural type T-1, wherein X is S, Z is N, $R^7$ and $R^2$ are $CH_3$, $R^1, R^3, R^4, R^5, R^6$ and $R^8$ are hydrogen and $R^{25}$ and $R^{26}$ are as defined in Table 1.
Table 56:
This table covers 272 compounds of the structural type T-1, wherein X is S, Z is N, $R^6$ is $CH_3$, $R^1, R^2, R^3, R^4, R^5, R^7$ and $R^8$ are hydrogen and $R^{25}$ and $R^{26}$ are as defined in Table 1.
Table 57:
This table covers 272 compounds of the structural type T-1, wherein X is S, Z is N, $R^6$ is $CH_2CH_3$, $R^1, R^2, R^3, R^4, R^5, R^7$ and $R^8$ are hydrogen and $R^{25}$ and $R^{26}$ are as defined in Table 1.
Table 58:
This table covers 272 compounds of the structural type T-1, wherein X is S, Z is N, $R^6$ is $CH_2OCH_3$, $R^1, R^2, R^3, R^4, R^5, R^7$ and $R^8$ are hydrogen and $R^{25}$ and $R^{26}$ are as defined in Table 1.
Table 59:
This table covers 272 compounds of the structural type T-1, wherein X is S, Z is N, $R^6$ is $CH_2OCH_2CH_3$, $R^1, R^2, R^3, R^4, R^5, R^7$ and $R^8$ are hydrogen and $R^{25}$ and $R^{26}$ are as defined in Table 1.
Table 60:
This table covers 272 compounds of the structural type T-1, wherein X is S, Z is N, $R^6$ is $CH_2CH_2OCH_3$, $R^1, R^2, R^3, R^4, R^5, R^7$ and $R^8$ are hydrogen and $R^{25}$ and $R^{26}$ are as defined in Table 1.

TABLE 61

This table covers 272 compounds of the structural type T-2:

T-2 wherein X is S, Z is C—H, $R^1, R^2, R^3, R^4, R^5, R^6, R^7$ and $R^8$ are hydrogen Table 62:
This table covers 272 compounds of the structural type T-2, wherein X is S, Z is C—H, $R^7$ is $CH_3$, $R^1, R^2, R^3, R^4, R^5, R^6$ and $R^8$ are hydrogen and $R^{25}$ and $R^{26}$ are as defined in Table 1.
Table 63:
This table covers 272 compounds of the structural type T-2, wherein X is S, Z is C—H, $R^7$ is $CH_2CH_3$, $R^1, R^2, R^3, R^4, R^5, R^6$ and $R^8$ are hydrogen and $R^{25}$ and $R^{26}$ are as defined in Table 1.
Table 64:
This table covers 272 compounds of the structural type T-2, wherein X is S, Z is C—H, $R^7$ is cyclopropyl, $R^1, R^2, R^3, R^4, R^5, R^6$ and $R^8$ are hydrogen and $R^{25}$ and $R^{26}$ are as defined in Table 1.
Table 65:
This table covers 272 compounds of the structural type T-2, wherein X is S, Z is C—H, $R^7$ is $CH_2OCH_3$, $R^1, R^2, R^3, R^4, R^5, R^6$ and $R^8$ are hydrogen and $R^{25}$ and $R^{26}$ are as defined in Table 1.
Table 66:
This table covers 272 compounds of the structural type T-2, wherein X is S, Z is C—H, $R^7$ is $CH_2OCH_2CH_3$, $R^1, R^2, R^3, R^4, R^5, R^6$ and $R^8$ are hydrogen and $R^{25}$ and $R^{26}$ are as defined in Table 1.
Table 67:
This table covers 272 compounds of the structural type T-2, wherein X is S, Z is C—H, $R^7$ is $CH_2CH_2OCH_3$, $R^1, R^2, R^3, R^4, R^5, R^6$ and $R^8$ are hydrogen and $R^{25}$ and $R^{26}$ are as defined in Table 1.
Table 68:
This table covers 272 compounds of the structural type T-2, wherein X is S, Z is C—H, $R^7$ is $OCH_3$, $R^1, R^2, R^3, R^4, R^5, R^6$ and $R^8$ are hydrogen and $R^{25}$ and $R^{26}$ are as defined in Table 1.
Table 69:
This table covers 272 compounds of the structural type T-2, wherein X is S, Z is C—H, $R^7$ is $OCH_2CH_3$, $R^1, R^2, R^3, R^4, R^5, R^6$ and $R^8$ are hydrogen and $R^{25}$ and $R^{26}$ are as defined in Table 1.
Table 70:
This table covers 272 compounds of the structural type T-2, wherein X is S, Z is C—H, $R^7$ and $R^2$ are $CH_3$, $R^1, R^3, R^4, R^5, R^6$ and $R^8$ are hydrogen and $R^{25}$ and $R^{26}$ are as defined in Table 1.

Table 71:
This table covers 272 compounds of the structural type T-2, wherein X is S, Z is C—H, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 72:
This table covers 272 compounds of the structural type T-2, wherein X is S, Z is C—H, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 73:
This table covers 272 compounds of the structural type T-2, wherein X is S, Z is C—H, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 74:
This table covers 272 compounds of the structural type T-2, wherein X is S, Z is C—H, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 75:
This table covers 272 compounds of the structural type T-2, wherein X is S, Z is C—H, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 76:
This table covers 272 compounds of the structural type T-2, wherein X is S, Z is C—$CH_3$, $R^1$, $R^2$, $R^3$, $R^4$, $R^5$, $R^6$, $R^7$ and $R^8$ are hydrogen Table 77:
This table covers 272 compounds of the structural type T-2, wherein X is S, Z is C—$CH_3$, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 78:
This table covers 272 compounds of the structural type T-2, wherein X is S, Z is C—$CH_3$, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 79:
This table covers 272 compounds of the structural type T-2, wherein X is S, Z is C—$CH_3$, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 80:
This table covers 272 compounds of the structural type T-2, wherein X is S, Z is C—$CH_3$, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 81:
This table covers 272 compounds of the structural type T-2, wherein X is S, Z is C—$CH_3$, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 82:
This table covers 272 compounds of the structural type T-2, wherein X is S, Z is C—$CH_3$, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 83:
This table covers 272 compounds of the structural type T-2, wherein X is S, Z is C—$CH_3$, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 84:
This table covers 272 compounds of the structural type T-2, wherein X is S, Z is C—$CH_3$, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 85:
This table covers 272 compounds of the structural type T-2, wherein X is S, Z is C—$CH_3$, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 86:
This table covers 272 compounds of the structural type T-2, wherein X is S, Z is C—$CH_3$, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 87:
This table covers 272 compounds of the structural type T-2, wherein X is S, Z is C—$CH_3$, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 88:
This table covers 272 compounds of the structural type T-2, wherein X is S, Z is C—$CH_3$, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 89:
This table covers 272 compounds of the structural type T-2, wherein X is S, Z is C—$CH_3$, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 90:
This table covers 272 compounds of the structural type T-2, wherein X is S, Z is C—$CH_3$, $R^6$ is $CH_2CH_2OCH_3$, $R^1$, $R^2$, $R^3$, $R^5$, $R^7$ and $R^8$ are hydrogen and $R^{25}$ and $R^{26}$ are as defined in Table 1.

Table 91:
This table covers 272 compounds of the structural type T-2, wherein X is S, Z is C—$CH_2CH_3$, $R^1$, $R^2$, $R^3$, $R^4$, $R^5$, $R^6$, $R^7$ and $R^8$ are hydrogen Table 92:
This table covers 272 compounds of the structural type T-2, wherein X is S, Z is C—$CH_2CH_3$, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 93:
This table covers 272 compounds of the structural type T-2, wherein X is S, Z is C—$CH_2CH_3$, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 94:
This table covers 272 compounds of the structural type T-2, wherein X is S, Z is C—$CH_2CH_3$, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 95:
This table covers 272 compounds of the structural type T-2, wherein X is S, Z is C—$CH_2CH_3$, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 96:
This table covers 272 compounds of the structural type T-2, wherein X is S, Z is C—$CH_2CH_3$, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are defined in Table 1.

Table 97:
This table covers 272 compounds of the structural type T-2, wherein X is S, Z is C—$CH_2CH_3$, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 98:
This table covers 272 compounds of the structural type T-2, wherein X is S, Z is C—$CH_2CH_3$, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 99:
This table covers 272 compounds of the structural type T-2, wherein X is S, Z is C—$CH_2CH_3$, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 100:
This table covers 272 compounds of the structural type T-2, wherein X is S, Z is C—$CH_2CH_3$, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 101:
This table covers 272 compounds of the structural type T-2, wherein X is S, Z is C—$CH_2CH_3$, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 102:
This table covers 272 compounds of the structural type T-2, wherein X is S, Z is C—$CH_2CH_3$, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 103:
This table covers 272 compounds of the structural type T-2, wherein X is S, Z is C—$CH_2CH_3$, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 104:
This table covers 272 compounds of the structural type T-2, wherein X is S, Z is C—$CH_2CH_3$, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 105:
This table covers 272 compounds of the structural type T-2, wherein X is S, Z is C—$CH_2CH_3$, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 106:
This table covers 272 compounds of the structural type T-2, wherein X is S, Z is N, $R^1$, $R^2$, $R^3$, $R^4$, $R^5$, $R^6$, $R^7$ and $R^8$ are hydrogen Table 107:
This table covers 272 compounds of the structural type T-2, wherein X is S, Z is N, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 108:
This table covers 272 compounds of the structural type T-2, wherein X is S, Z is N, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 109:
This table covers 272 compounds of the structural type T-2, wherein X is S, Z is N, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 110:
This table covers 272 compounds of the structural type T-2, wherein X is S, Z is N, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 111:
This table covers 272 compounds of the structural type T-2, wherein X is S, Z is N, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 112:
This table covers 272 compounds of the structural type T-2, wherein X is S, Z is N, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 113:
This table covers 272 compounds of the structural type T-2, wherein X is S, Z is N, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 114:
This table covers 272 compounds of the structural type T-2, wherein X is S, Z is N, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 115:
This table covers 272 compounds of the structural type T-2, wherein X is S, Z is N, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 116:
This table covers 272 compounds of the structural type T-2, wherein X is S, Z is N, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 117:
This table covers 272 compounds of the structural type T-2, wherein X is S, Z is N, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 118:
This table covers 272 compounds of the structural type T-2, wherein X is S, Z is N, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 119:
This table covers 272 compounds of the structural type T-2, wherein X is S, Z is N, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 120:
This table covers 272 compounds of the structural type T-2, wherein X is S, Z is N, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 121:
This table covers 272 compounds of the structural type T-1, wherein X is O, Z is C—H, $R^1$, $R^2$, $R^3$, $R^4$, $R^5$, $R^6$, $R^7$ and $R^8$ are hydrogen Table 122:
This table covers 272 compounds of the structural type T-1, wherein X is O, Z is C—H, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 123:
This table covers 272 compounds of the structural type T-1, wherein X is O, Z is C—H, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 124:
This table covers 272 compounds of the structural type T-1, wherein X is O, Z is C—H, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 125:
This table covers 272 compounds of the structural type T-1, wherein X is O, Z is C—H, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 126:
This table covers 272 compounds of the structural type T-1, wherein X is O, Z is C—H, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 127:
This table covers 272 compounds of the structural type T-1, wherein X is O, Z is C—H, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 128:
This table covers 272 compounds of the structural type T-1, wherein X is O, Z is C—H, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 129:
This table covers 272 compounds of the structural type T-1, wherein X is O, Z is C—H, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 130:
This table covers 272 compounds of the structural type T-1, wherein X is O, Z is C—H, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 131:
This table covers 272 compounds of the structural type T-1, wherein X is O, Z is C—H, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 132:
This table covers 272 compounds of the structural type T-1, wherein X is O, Z is C—H, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 133:
This table covers 272 compounds of the structural type T-1, wherein X is O, Z is C—H, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 134:
This table covers 272 compounds of the structural type T-1, wherein X is O, Z is C—H, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 135:
This table covers 272 compounds of the structural type T-1, wherein X is O, Z is C—H, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 136:
This table covers 272 compounds of the structural type T-1, wherein X is O, Z is C—$CH_3$, $R^1$, $R^2$, $R^3$, $R^4$, $R^5$, $R^6$, $R^7$ and $R^8$ are hydrogen Table 137:
This table covers 272 compounds of the structural type T-1, wherein X is O, Z is C—$CH_3$, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 138:
This table covers 272 compounds of the structural type T-1, wherein X is O, Z is C—$CH_3$, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 139:
This table covers 272 compounds of the structural type T-1, wherein X is O, Z is C—$CH_3$, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 140:
This table covers 272 compounds of the structural type T-1, wherein X is O, Z is C—$CH_3$, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 141:
This table covers 272 compounds of the structural type T-1, wherein X is O, Z is C—$CH_3$, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 142:
This table covers 272 compounds of the structural type T-1, wherein X is O, Z is C—$CH_3$, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 143:
This table covers 272 compounds of the structural type T-1, wherein X is O, Z is C—$CH_3$, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 144:
This table covers 272 compounds of the structural type T-1, wherein X is O, Z is C—$CH_3$, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 145:
This table covers 272 compounds of the structural type T-1, wherein X is O, Z is C—$CH_3$, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 146:
This table covers 272 compounds of the structural type T-1, wherein X is O, Z is C—$CH_3$, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 147:
This table covers 272 compounds of the structural type T-1, wherein X is O, Z is C—$CH_3$, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 148:
This table covers 272 compounds of the structural type T-1, wherein X is O, Z is C—$CH_3$, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 149:
This table covers 272 compounds of the structural type T-1, wherein X is O, Z is C—$CH_3$, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 150:
This table covers 272 compounds of the structural type T-1, wherein X is O, Z is C—CH$_3$, R$^6$ is CH$_2$CH$_2$OCH$_3$, R$^1$, R$^2$, R$^3$, R$^4$, R$^5$, R$^7$ and R$^8$ are hydrogen and R$^{25}$ and R$^{26}$ are as defined in Table 1.

Table 151:
This table covers 272 compounds of the structural type T-1, wherein X is O, Z is C—CH$_2$CH$_3$, R$^1$, R$^2$, R$^3$, R$^4$, R$^5$, R$^6$, R$^7$ and R$^8$ are hydrogen Table 152:
This table covers 272 compounds of the structural type T-1, wherein X is O, Z is C—CH$_2$CH$_3$, R$^7$ is CH$_3$, R$^1$, R$^2$, R$^3$, R$^4$, R$^5$, R$^6$ and R$^8$ are hydrogen and R$^{25}$ and R$^{26}$ are as defined in Table 1.

Table 153:
This table covers 272 compounds of the structural type T-1, wherein X is O, Z is C—CH$_2$CH$_3$, R$^7$ is CH$_2$CH$_3$, R$^1$, R$^2$, R$^3$, R$^4$, R$^5$, R$^6$ and R$^8$ are hydrogen and R$^{25}$ and R$^{26}$ are as defined in Table 1.

Table 154:
This table covers 272 compounds of the structural type T-1, wherein X is O, Z is C—CH$_2$CH$_3$, R$^7$ is cyclopropyl, R$^1$, R$^2$, R$^3$, R$^4$, R$^5$, R$^6$ and R$^8$ are hydrogen and R$^{25}$ and R$^{26}$ are as defined in Table 1.

Table 155:
This table covers 272 compounds of the structural type T-1, wherein X is O, Z is C—CH$_2$CH$_3$, R$^7$ is CH$_2$OCH$_3$, R$^1$, R$^2$, R$^3$, R$^4$, R$^5$, R$^6$ and R$^8$ are hydrogen and R$^{25}$ and R$^{26}$ are as defined in Table 1.

Table 156:
This table covers 272 compounds of the structural type T-1, wherein X is O, Z is C—CH$_2$CH$_3$, R$^7$ is CH$_2$OCH$_2$CH$_3$, R$^1$, R$^2$, R$^3$, R$^4$, R$^5$, R$^6$ and R$^8$ are hydrogen and R$^{25}$ and R$^{26}$ are as defined in Table 1.

Table 157:
This table covers 272 compounds of the structural type T-1, wherein X is O, Z is C—CH$_2$CH$_3$, R$^7$ is CH$_2$CH$_2$OCH$_3$, R$^1$, R$^2$, R$^3$, R$^4$, R$^5$, R$^6$ and R$^8$ are hydrogen and R$^{25}$ and R$^{26}$ are as defined in Table 1.

Table 158:
This table covers 272 compounds of the structural type T-1, wherein X is O, Z is C—CH$_2$CH$_3$, R$^7$ is OCH$_3$, R$^1$, R$^2$, R$^3$, R$^4$, R$^5$, R$^6$ and R$^8$ are hydrogen and R$^{25}$ and R$^{26}$ are as defined in Table 1.

Table 159:
This table covers 272 compounds of the structural type T-1, wherein X is O, Z is C—CH$_2$CH$_3$, R$^7$ is OCH$_2$CH$_3$, R$^1$, R$^2$, R$^3$, R$^4$, R$^5$, R$^6$ and R$^8$ are hydrogen and R$^{25}$ and R$^{26}$ are as defined in Table 1.

Table 160:
This table covers 272 compounds of the structural type T-1, wherein X is O, Z is C—CH$_2$CH$_3$, R$^7$ and R$^2$ are CH$_3$, R$^1$, R$^3$, R$^4$, R$^5$, R$^6$ and R$^8$ are hydrogen and R$^{25}$ and R$^{26}$ are as defined in Table 1.

Table 161:
This table covers 272 compounds of the structural type T-1, wherein X is O, Z is C—CH$_2$CH$_3$, R$^6$ is CH$_3$, R$^1$, R$^2$, R$^3$, R$^4$, R$^5$, R$^7$ and R$^8$ are hydrogen and R$^{25}$ and R$^{26}$ are as defined in Table 1.

Table 162:
This table covers 272 compounds of the structural type T-1, wherein X is O, Z is C—CH$_2$CH$_3$, R$^6$ is CH$_2$CH$_3$, R$^1$, R$^2$, R$^3$, R$^4$, R$^5$, R$^7$ and R$^8$ are hydrogen and R$^{25}$ and R$^{26}$ are as defined in Table 1.

Table 163:
This table covers 272 compounds of the structural type T-1, wherein X is O, Z is C—CH$_2$CH$_3$, R$^6$ is CH$_2$OCH$_3$, R$^1$, R$^2$, R$^3$, R$^4$, R$^5$, R$^7$ and R$^8$ are hydrogen and R$^{25}$ and R$^{26}$ are as defined in Table 1.

Table 164:
This table covers 272 compounds of the structural type T-1, wherein X is O, Z is C—CH$_2$CH$_3$, R$^6$ is CH$_2$OCH$_2$CH$_3$, R$^1$, R$^2$, R$^3$, R$^4$, R$^7$ and R$^8$ are hydrogen and R$^{25}$ and R$^{26}$ are as defined in Table 1.

Table 165:
This table covers 272 compounds of the structural type T-1, wherein X is O, Z is C—CH$_2$CH$_3$, R$^6$ is CH$_2$CH$_2$OCH$_3$, R$^1$, R$^4$, R$^5$, R$^7$ and R$^8$ are hydrogen and R$^{25}$ and R$^{26}$ are as defined in Table 1.

Table 166:
This table covers 272 compounds of the structural type T-1, wherein X is O, Z is N, R$^1$, R$^2$, R$^3$, R$^4$, R$^5$, R$^6$, R$^7$ and R$^8$ are hydrogen Table 167:
This table covers 272 compounds of the structural type T-1, wherein X is O, Z is N, R$^7$ is CH$_3$, R$^1$, R$^2$, R$^3$, R$^4$, R$^5$, R$^6$ and R$^8$ are hydrogen and R$^{25}$ and R$^{26}$ are as defined in Table 1.

Table 168:
This table covers 272 compounds of the structural type T-1, wherein X is O, Z is N, R$^7$ is CH$_2$CH$_3$, R$^1$, R$^2$, R$^3$, R$^4$, R$^5$, R$^6$ and R$^8$ are hydrogen and R$^{25}$ and R$^{26}$ are as defined in Table 1.

Table 169:
This table covers 272 compounds of the structural type T-1, wherein X is O, Z is N, R$^7$ is cyclopropyl R$^1$, R$^2$, R$^3$, R$^4$, R$^5$, R$^6$ and R$^8$ are hydrogen and R$^{25}$ and R$^{26}$ are as defined in Table 1.

Table 170:
This table covers 272 compounds of the structural type T-1, wherein X is O, Z is N, R$^7$ is CH$_2$OCH$_3$, R$^1$, R$^2$, R$^3$, R$^4$, R$^5$, R$^6$ and R$^8$ are hydrogen and R$^{25}$ and R$^{26}$ are as defined in Table 1.

Table 171:
This table covers 272 compounds of the structural type T-1, wherein X is O, Z is N, R$^7$ is CH$_2$OCH$_2$CH$_3$, R$^1$, R$^2$, R$^3$, R$^4$, R$^5$, R$^6$ and R$^8$ are hydrogen and R$^{25}$ and R$^{26}$ are as defined in Table 1.

Table 172:
This table covers 272 compounds of the structural type T-1, wherein X is O, Z is N, R$^7$ is CH$_2$CH$_2$OCH$_3$, R$^1$, R$^2$, R$^3$, R$^4$, R$^5$, R$^6$ and R$^8$ are hydrogen and R$^{25}$ and R$^{26}$ are as defined in Table 1.

Table 173:
This table covers 272 compounds of the structural type T-1, wherein X is O, Z is N, R$^7$ is OCH$_3$, R$^1$, R$^2$, R$^3$, R$^4$, R$^5$, R$^6$ and R$^8$ are hydrogen and R$^{25}$ and R$^{26}$ are as defined in Table 1.

Table 174:
This table covers 272 compounds of the structural type T-1, wherein X is O, Z is N, R$^7$ is OCH$_2$CH$_3$, R$^1$, R$^2$, R$^3$, R$^4$, R$^5$, R$^6$ and R$^8$ are hydrogen and R$^{25}$ and R$^{26}$ are as defined in Table 1.

Table 175:
This table covers 272 compounds of the structural type T-1, wherein X is O, Z is N, R$^7$ and R$^2$ are CH$_3$, R$^1$, R$^3$, R$^4$, R$^5$, R$^6$ and R$^8$ are hydrogen and R$^{25}$ and R$^{26}$ are as defined in Table 1.

Table 176:
This table covers 272 compounds of the structural type T-1, wherein X is O, Z is N, R$^6$ is CH$_3$, R$^1$, R$^2$, R$^3$, R$^4$, R$^5$, R$^7$ and R$^8$ are hydrogen and R$^{25}$ and R$^{26}$ are as defined in Table 1.

Table 177:
This table covers 272 compounds of the structural type T-1, wherein X is O, Z is N, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 178:
This table covers 272 compounds of the structural type T-1, wherein X is O, Z is N, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 179:
This table covers 272 compounds of the structural type T-1, wherein X is O, Z is N, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 180:
This table covers 272 compounds of the structural type T-1, wherein X is O, Z is N, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 181:
This table covers 272 compounds of the structural type T-2: wherein X is O, Z is C—H, $R^1$, $R^2$, $R^3$, $R^4$, $R^5$, $R^6$, $R^7$ and $R^8$ are hydrogen Table 182:
This table covers 272 compounds of the structural type T-2, wherein X is O, Z is C—H, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 183:
This table covers 272 compounds of the structural type T-2, wherein X is O, Z is C—H, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 184:
This table covers 272 compounds of the structural type T-2, wherein X is O, Z is C—H, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 185:
This table covers 272 compounds of the structural type T-2, wherein X is O, Z is C—H, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 186:
This table covers 272 compounds of the structural type T-2, wherein X is O, Z is C—H, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 187:
This table covers 272 compounds of the structural type T-2, wherein X is O, Z is C—H, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 188:
This table covers 272 compounds of the structural type T-2, wherein X is O, Z is C—H, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 189:
This table covers 272 compounds of the structural type T-2, wherein X is O, Z is C—H, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 190:
This table covers 272 compounds of the structural type T-2, wherein X is O, Z is C—H, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 191:
This table covers 272 compounds of the structural type T-2, wherein X is O, Z is C—H, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 192:
This table covers 272 compounds of the structural type T-2, wherein X is O, Z is C—H, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 193:
This table covers 272 compounds of the structural type T-2, wherein X is O, Z is C—H, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 194:
This table covers 272 compounds of the structural type T-2, wherein X is O, Z is C—H, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 195:
This table covers 272 compounds of the structural type T-2, wherein X is O, Z is C—H, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 196:
This table covers 272 compounds of the structural type T-2, wherein X is O, Z is C—$CH_3$, $R^1$, $R^2$, $R^3$, $R^4$, $R^5$, $R^6$, $R^7$ and $R^8$ are hydrogen Table 197:
This table covers 272 compounds of the structural type T-2, wherein X is O, Z is C—$CH_3$, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 198:
This table covers 272 compounds of the structural type T-2, wherein X is O, Z is C—$CH_3$, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 199:
This table covers 272 compounds of the structural type T-2, wherein X is O, Z is C—$CH_3$, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 200:
This table covers 272 compounds of the structural type T-2, wherein X is O, Z is C—$CH_3$, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 201:
This table covers 272 compounds of the structural type T-2, wherein X is O, Z is C—$CH_3$, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 202:
This table covers 272 compounds of the structural type T-2, wherein X is O, Z is C—$CH_3$, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 203:

This table covers 272 compounds of the structural type T-2, wherein X is O, Z is C—$CH_3$, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 204:

This table covers 272 compounds of the structural type T-2, wherein X is O, Z is C—$CH_3$, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 205:

This table covers 272 compounds of the structural type T-2, wherein X is O, Z is C—$CH_3$, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 206:

This table covers 272 compounds of the structural type T-2, wherein X is O, Z is C—$CH_3$, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 207:

This table covers 272 compounds of the structural type T-2, wherein X is O, Z is C—$CH_3$, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 208:

This table covers 272 compounds of the structural type T-2, wherein X is O, Z is C—$CH_3$, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 209:

This table covers 272 compounds of the structural type T-2, wherein X is O, Z is C—$CH_3$, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 210:

This table covers 272 compounds of the structural type T-2, wherein X is O, Z is C—$CH_3$, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 211:

This table covers 272 compounds of the structural type T-2, wherein X is O, Z is C—$CH_2CH_3$, $R^1$, $R^2$, $R^3$, $R^4$, $R^5$, $R^6$, $R^7$ and $R^8$ are hydrogen Table 212:

This table covers 272 compounds of the structural type T-2, wherein X is O, Z is C—$CH_2CH_3$, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 213:

This table covers 272 compounds of the structural type T-2, wherein X is O, Z is C—$CH_2CH_3$, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 214:

This table covers 272 compounds of the structural type T-2, wherein X is O, Z is C—$CH_2CH_3$, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 215:

This table covers 272 compounds of the structural type T-2, wherein X is O, Z is C—$CH_2CH_3$, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 216:

This table covers 272 compounds of the structural type T-2, wherein X is O, Z is C—$CH_2CH_3$, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 217:

This table covers 272 compounds of the structural type T-2, wherein X is O, Z is C—$CH_2CH_3$, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 218:

This table covers 272 compounds of the structural type T-2, wherein X is O, Z is C—$CH_2CH_3$, $R^7$ is $OCH_2$, $R^1$, $R^2$, $R^3$, $R^4$, $R^5$, $R^6$ and $R^8$ are hydrogen and $R^{25}$ and $R^{26}$ are as defined in Table 1.

Table 219:

This table covers 272 compounds of the structural type T-2, wherein X is O, Z is C—$CH_2CH_3$, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 220:

This table covers 272 compounds of the structural type T-2, wherein X is O, Z is C—$CH_2CH_3$, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 221:

This table covers 272 compounds of the structural type T-2, wherein X is O, Z is C—$CH_2CH_3$, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 222:

This table covers 272 compounds of the structural type T-2, wherein X is O, Z is C—$CH_2CH_3$, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 223:

This table covers 272 compounds of the structural type T-2, wherein X is O, Z is C—$CH_2CH_3$, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 224:

This table covers 272 compounds of the structural type T-2, wherein X is O, Z is C—$CH_2CH_3$, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 225:

This table covers 272 compounds of the structural type T-2, wherein X is O, Z is C—$CH_2CH_3$, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 226:

This table covers 272 compounds of the structural type T-2, wherein X is O, Z is N, $R^1$, $R^2$, $R^3$, $R^4$, $R^5$, $R^6$, $R^7$ and $R^8$ are hydrogen Table 227:

This table covers 272 compounds of the structural type T-2, wherein X is O, Z is N, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 228:

This table covers 272 compounds of the structural type T-2, wherein X is O, Z is N, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 229:
This table covers 272 compounds of the structural type T-2, wherein X is O, Z is N, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 230:
This table covers 272 compounds of the structural type T-2, wherein X is O, Z is N, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 231:
This table covers 272 compounds of the structural type T-2, wherein X is O, Z is N, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 232:
This table covers 272 compounds of the structural type T-2, wherein X is O, Z is N, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 233:
This table covers 272 compounds of the structural type T-2, wherein X is O, Z is N, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 234:
This table covers 272 compounds of the structural type T-2, wherein X is O, Z is N, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 235:
This table covers 272 compounds of the structural type T-2, wherein X is O, Z is N, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 236:
This table covers 272 compounds of the structural type T-2, wherein X is O, Z is N, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 237:
This table covers 272 compounds of the structural type T-2, wherein X is O, Z is N, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 238:
This table covers 272 compounds of the structural type T-2, wherein X is O, Z is N, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 239:
This table covers 272 compounds of the structural type T-2, wherein X is O, Z is N, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 240:
This table covers 272 compounds of the structural type T-2, wherein X is O, Z is N, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 241:
This table covers 272 compounds of the structural type T-1, wherein X is Se, Z is C—H, $R^1$, $R^2$, $R^3$, $R^4$, $R^5$, $R^6$, $R^7$ and $R^8$ are hydrogen Table 242:
This table covers 272 compounds of the structural type T-1, wherein X is Se, Z is C—H, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 243:
This table covers 272 compounds of the structural type T-1, wherein X is Se, Z is C—H, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 244:
This table covers 272 compounds of the structural type T-1, wherein X is Se, Z is C—H, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 255:
This table covers 272 compounds of the structural type T-1, wherein X is Se, Z is C—H, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 246:
This table covers 272 compounds of the structural type T-1, wherein X is Se, Z is C—H, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 247:
This table covers 272 compounds of the structural type T-1, wherein X is Se, Z is C—H, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 248:
This table covers 272 compounds of the structural type T-1, wherein X is Se, Z is C—H, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 249:
This table covers 272 compounds of the structural type T-1, wherein X is Se, Z is C—H, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 250:
This table covers 272 compounds of the structural type T-1, wherein X is Se, Z is C—H, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 251:
This table covers 272 compounds of the structural type T-1, wherein X is Se, Z is C—H, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 252:
This table covers 272 compounds of the structural type T-1, wherein X is Se, Z is C—H, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 253:
This table covers 272 compounds of the structural type T-1, wherein X is Se, Z is C—H, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 254:
This table covers 272 compounds of the structural type T-1, wherein X is Se, Z is C—H, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 255:
This table covers 272 compounds of the structural type T-1, wherein X is Se, Z is C—H, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 256:
This table covers 272 compounds of the structural type T-1, wherein X is Se, Z is C—$CH_3$, $R^1$, $R^2$, $R^3$, $R^4$, $R^5$, $R^6$, $R^7$ and $R^8$ are hydrogen Table 257:
This table covers 272 compounds of the structural type T-1, wherein X is Se, Z is C—$CH_3$, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 258:
This table covers 272 compounds of the structural type T-1, wherein X is Se, Z is C—$CH_3$, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 259:
This table covers 272 compounds of the structural type T-1, wherein X is Se, Z is C—$CH_3$, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 260:
This table covers 272 compounds of the structural type T-1, wherein X is Se, Z is C—$CH_3$, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 261:
This table covers 272 compounds of the structural type T-1, wherein X is Se, Z is C—$CH_3$, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 262:
This table covers 272 compounds of the structural type T-1, wherein X is Se, Z is C—$CH_3$, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 263:
This table covers 272 compounds of the structural type T-1, wherein X is Se, Z is C—$CH_3$, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 264:
This table covers 272 compounds of the structural type T-1, wherein X is Se, Z is C—$CH_3$, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 265:
This table covers 272 compounds of the structural type T-1, wherein X is Se, Z is C—$CH_3$, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 266:
This table covers 272 compounds of the structural type T-1, wherein X is Se, Z is C—$CH_3$, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 267:
This table covers 272 compounds of the structural type T-1, wherein X is Se, Z is C—$CH_3$, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 268:
This table covers 272 compounds of the structural type T-1, wherein X is Se, Z is C—$CH_3$, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 269:
This table covers 272 compounds of the structural type T-1, wherein X is Se, Z is C—$CH_3$, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 270:
This table covers 272 compounds of the structural type T-1, wherein X is Se, Z is C—$CH_3$, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 271:
This table covers 272 compounds of the structural type T-1, wherein X is Se, Z is C—$CH_2CH_3$, $R^1$, $R^2$, $R^3$, $R^4$, $R^5$, $R^6$, $R^7$ and $R^8$ are hydrogen Table 272:
This table covers 272 compounds of the structural type T-1, wherein X is Se, Z is C—$CH_2CH_3$, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 273:
This table covers 272 compounds of the structural type T-1, wherein X is Se, Z is C—$CH_2CH_3$, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 274:
This table covers 272 compounds of the structural type T-1, wherein X is Se, Z is C—$CH_2CH_3$, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 275:
This table covers 272 compounds of the structural type T-1, wherein X is Se, Z is C—$CH_2CH_3$, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 276:
This table covers 272 compounds of the structural type T-1, wherein X is Se, Z is C—$CH_2CH_3$, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 277:
This table covers 272 compounds of the structural type T-1, wherein X is Se, Z is C—$CH_2CH_3$, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 278:
This table covers 272 compounds of the structural type T-1, wherein X is Se, Z is C—$CH_2CH_3$, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 279:
This table covers 272 compounds of the structural type T-1, wherein X is Se, Z is C—$CH_2CH_3$, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 280:
This table covers 272 compounds of the structural type T-1, wherein X is Se, Z is C—$CH_2CH_3$, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 281:
This table covers 272 compounds of the structural type T-1, wherein X is Se, Z is C—$CH_2CH_3$, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 282:
This table covers 272 compounds of the structural type T-1, wherein X is Se, Z is C—$CH_2CH_3$, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 283:
This table covers 272 compounds of the structural type T-1, wherein X is Se, Z is C—$CH_2CH_3$, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 284:
This table covers 272 compounds of the structural type T-1, wherein X is Se, Z is C—$CH_2CH_3$, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 285:
This table covers 272 compounds of the structural type T-1, wherein X is Se, Z is C—$CH_2CH_3$, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 286:
This table covers 272 compounds of the structural type T-1, wherein X is Se, Z is N, $R^1$, $R^2$, $R^3$, $R^4$, $R^5$, $R^6$, $R^7$ and $R^8$ are hydrogen Table 287:
This table covers 272 compounds of the structural type T-1, wherein X is Se, Z is N, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 288:
This table covers 272 compounds of the structural type T-1, wherein X is Se, Z is N, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 289:
This table covers 272 compounds of the structural type T-1, wherein X is Se, Z is N, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 290:
This table covers 272 compounds of the structural type T-1, wherein X is Se, Z is N, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 291:
This table covers 272 compounds of the structural type T-1, wherein X is Se, Z is N, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 292:
This table covers 272 compounds of the structural type T-1, wherein X is Se, Z is N, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 293:
This table covers 272 compounds of the structural type T-1, wherein X is Se, Z is N, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 294:
This table covers 272 compounds of the structural type T-1, wherein X is Se, Z is N, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 295:
This table covers 272 compounds of the structural type T-1, wherein X is Se, Z is N, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 296:
This table covers 272 compounds of the structural type T-1, wherein X is Se, Z is N, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 297:
This table covers 272 compounds of the structural type T-1, wherein X is Se, Z is N, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 298:
This table covers 272 compounds of the structural type T-1, wherein X is Se, Z is N, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 299:
This table covers 272 compounds of the structural type T-1, wherein X is Se, Z is N, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 300:
This table covers 272 compounds of the structural type T-1, wherein X is Se, Z is N, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 301:
This table covers 272 compounds of the structural type T-2: wherein X is Se, Z is C—H, $R^1$, $R^2$, $R^3$, $R^4$, $R^5$, $R^6$, $R^7$ and $R^8$ are hydrogen Table 302:
This table covers 272 compounds of the structural type T-2, wherein X is Se, Z is C—H, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 303:
This table covers 272 compounds of the structural type T-2, wherein X is Se, Z is C—H, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 304:
This table covers 272 compounds of the structural type T-2, wherein X is Se, Z is C—H, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 305:
This table covers 272 compounds of the structural type T-2, wherein X is Se, Z is C—H, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 306:
This table covers 272 compounds of the structural type T-2, wherein X is Se, Z is C—H, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 307:
This table covers 272 compounds of the structural type T-2, wherein X is Se, Z is C—H, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 308:
This table covers 272 compounds of the structural type T-2, wherein X is Se, Z is C—H, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 309:
This table covers 272 compounds of the structural type T-2, wherein X is Se, Z is C—H, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 310:
This table covers 272 compounds of the structural type T-2, wherein X is Se, Z is C—H, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 311:
This table covers 272 compounds of the structural type T-2, wherein X is Se, Z is C—H, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 312:
This table covers 272 compounds of the structural type T-2, wherein X is Se, Z is C—H, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 313:
This table covers 272 compounds of the structural type T-2, wherein X is Se, Z is C—H, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 314:
This table covers 272 compounds of the structural type T-2, wherein X is Se, Z is C—H, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 315:
This table covers 272 compounds of the structural type T-2, wherein X is Se, Z is C—H, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 316:
This table covers 272 compounds of the structural type T-2, wherein X is Se, Z is C—$CH_3$, $R^1$, $R^2$, $R^3$, $R^4$, $R^5$, $R^6$, $R^7$ and $R^8$ are hydrogen Table 317:
This table covers 272 compounds of the structural type T-2, wherein X is Se, Z is C—$CH_3$, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 318:
This table covers 272 compounds of the structural type T-2, wherein X is Se, Z is C—$CH_3$, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 319:
This table covers 272 compounds of the structural type T-2, wherein X is Se, Z is C—$CH_3$, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 320:
This table covers 272 compounds of the structural type T-2, wherein X is Se, Z is C—$CH_3$, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 321:
This table covers 272 compounds of the structural type T-2, wherein X is Se, Z is C—$CH_3$, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 322:
This table covers 272 compounds of the structural type T-2, wherein X is Se, Z is C—$CH_3$, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 323:
This table covers 272 compounds of the structural type T-2, wherein X is Se, Z is C—$CH_3$, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 324:
This table covers 272 compounds of the structural type T-2, wherein X is Se, Z is C—$CH_3$, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 325:
This table covers 272 compounds of the structural type T-2, wherein X is Se, Z is C—$CH_3$, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 326:
This table covers 272 compounds of the structural type T-2, wherein X is Se, Z is C—$CH_3$, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 327:
This table covers 272 compounds of the structural type T-2, wherein X is Se, Z is C—$CH_3$, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 328:
This table covers 272 compounds of the structural type T-2, wherein X is Se, Z is C—$CH_3$, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 329:
This table covers 272 compounds of the structural type T-2, wherein X is Se, Z is C—$CH_3$, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 330:
This table covers 272 compounds of the structural type T-2, wherein X is Se, Z is C—$CH_3$, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 331:
This table covers 272 compounds of the structural type T-2, wherein X is Se, Z is C—$CH_2CH_3$, $R^1$, $R^2$, $R^3$, $R^4$, $R^5$, $R^6$, $R^7$ and $R^8$ are hydrogen Table 332:
This table covers 272 compounds of the structural type T-2, wherein X is Se, Z is C—$CH_2CH_3$, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 333:
This table covers 272 compounds of the structural type T-2, wherein X is Se, Z is C—$CH_2CH_3$, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 334:
This table covers 272 compounds of the structural type T-2, wherein X is Se, Z is C—$CH_2CH_3$, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 335:
This table covers 272 compounds of the structural type T-2, wherein X is Se, Z is C—$CH_2CH_3$, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 336:
This table covers 272 compounds of the structural type T-2, wherein X is Se, Z is C—$CH_2CH_3$, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 337:
This table covers 272 compounds of the structural type T-2, wherein X is Se, Z is C—$CH_2CH_3$, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 338:
This table covers 272 compounds of the structural type T-2, wherein X is Se, Z is C—$CH_2CH_3$, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 339:
This table covers 272 compounds of the structural type T-2, wherein X is Se, Z is C—$CH_2CH_3$, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 340:
This table covers 272 compounds of the structural type T-2, wherein X is Se, Z is C—$CH_2CH_3$, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 341:
This table covers 272 compounds of the structural type T-2, wherein X is Se, Z is C—$CH_2CH_3$, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 342:
This table covers 272 compounds of the structural type T-2, wherein X is Se, Z is C—$CH_2CH_3$, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 343:
This table covers 272 compounds of the structural type T-2, wherein X is Se, Z is C—$CH_2CH_3$, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 344:
This table covers 272 compounds of the structural type T-2, wherein X is Se, Z is C—$CH_2CH_3$, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 345:
This table covers 272 compounds of the structural type T-2, wherein X is Se, Z is C—$CH_2CH_3$, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 346:
This table covers 272 compounds of the structural type T-2, wherein X is Se, Z is N, $R^1$, $R^2$, $R^3$, $R^4$, $R^5$, $R^6$, $R^7$ and $R^8$ are hydrogen Table 347:
This table covers 272 compounds of the structural type T-2, wherein X is Se, Z is N, $R^7$ is $CH_3$, $R^1$, $R^2$, $R^3$, $R^4$, $R^5$, $R^6$ and $R^8$ are hydrogen and $R^{25}$ and $R^{26}$ are as defined in Table 1.

Table 348:
This table covers 272 compounds of the structural type T-2, wherein X is Se, Z is N, $R^7$ is $CH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 349:
This table covers 272 compounds of the structural type T-2, wherein X is Se, Z is N, $R^7$ is cyclopropyl, $R^1$, $R^2$, $R^3$, $R^4$, $R^5$, $R^6$ and $R^8$ are hydrogen and $R^{25}$ and $R^{26}$ are as defined in Table 1.

Table 350:
This table covers 272 compounds of the structural type T-2, wherein X is Se, Z is N, $R^7$ is $CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 351:
This table covers 272 compounds of the structural type T-2, wherein X is Se, Z is N, $R^7$ is $CH_2OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 352:
This table covers 272 compounds of the structural type T-2, wherein X is Se, Z is N, $R^7$ is $CH_2CH_2OCH_3$, $R^1$, $R^2$, $R^3$, $R^4$, $R^5$, $R^6$ and $R^8$ are hydrogen and $R^{25}$ and $R^{26}$ are as defined in Table 1.

Table 353:
This table covers 272 compounds of the structural type T-2, wherein X is Se, Z is N, $R^7$ is $OCH_3$, $R^1$, $R^2$, $R^3$, $R^4$, $R^5$, $R^6$ and $R^8$ are hydrogen and $R^{25}$ and $R^{26}$ are as defined in Table 1.

Table 354:
This table covers 272 compounds of the structural type T-2, wherein X is Se, Z is N, $R^7$ is $OCH_2CH_3$, $R^1$, $R^2$, $R^3$, $R^4$, $R^5$, $R^6$ and $R^8$ are hydrogen and $R^{25}$ and $R^{26}$ are as defined in Table 1.

Table 355:
This table covers 272 compounds of the structural type T-2, wherein X is Se, Z is N, $R^7$ and $R^2$ are $CH_3$, $R^1$, $R^3$, $R^4$, $R^5$, $R^6$ and $R^8$ are hydrogen and $R^{25}$ and $R^{26}$ are as defined in Table 1.

Table 356:
This table covers 272 compounds of the structural type T-2, wherein X is Se, Z is N, $R^6$ is $CH_3$, $R^1$, $R^2$, $R^3$, $R^4$, $R^5$, $R^7$ and $R^8$ are hydrogen and $R^{25}$ and $R^{26}$ are as defined in Table 1.

Table 357:
This table covers 272 compounds of the structural type T-2, wherein X is Se, Z is N, $R^6$ is $CH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 358:
This table covers 272 compounds of the structural type T-2, wherein X is Se, Z is N, $R^6$ is $CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Table 359:
This table covers 272 compounds of the structural type T-2, wherein X is Se, Z is N, $R^6$ is $CH_2OCH_2CH_3$, $R^1$, $R^2$, $R^3$, $R^4$, $R^5$, $R^7$ and $R^8$ are hydrogen and $R^{25}$ and $R^{26}$ are as defined in Table 1.

Table 360:
This table covers 272 compounds of the structural type T-2, wherein X is Se, Z is N, $R^6$ is $CH_2CH_2OCH_3$, $R^1$, $R^2$, $R^3$, $R^4$, $R^5$, $R^7$ and $R^8$ are hydrogen and $R^{25}$ and $R^{26}$ are as defined in Table 1.

Biological Examples

Example A

Seeds of a variety of test species were sown in standard soil in pots. After cultivation for one day (pre-emergence) or after 10 days cultivation (post-emergence) under controlled conditions in a glasshouse, the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methylpyrrolidone, 42.2% dipropylene glycol monomethyl ether (Registry number 34590-94-8) and 0.2% X-77 (Registry number 11097-66-8). The test plants were then grown in a greenhouse under optimum conditions until, 14 or 15 days later for post-emergence and 19 or 20 days for pre-emergence, the test was evaluated (100=total damage to plant; 0=no damage to plant).

Test Plants:

*Alopecurus myosuroides* (ALOMY), *Avena fatua* (AVEFA), *Lolium perenne* (LOLPE), *Setaria faberi* (SETFA), *Digitaria sanguinalis* (DIGSA), *Echinochloa crus-galli* (ECHCG)

Pre-Emergence Activity

Example B

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5).

The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

Test Plants:

*Alopecurus myosuroides* (ALOMY), *Avena fatua* (AVEFA), *Setaria faberi* (SETFA), *Echinochloa crus-galli* (ECHCG) and *Amaranthus retoflexus* (AMARE)

| Compound Number | Rate g/ha | ALOMY | AVEFA | LOLPE | SETFA | DIGSA | ECHCG |
|---|---|---|---|---|---|---|---|
| T4  | 500 | 70  | 70  | 70  | 70  | 30  | 70  |
| T5  | 500 | 0   | 20  | 0   | 0   | 0   | 0   |
| T6  | 500 | 0   | 60  | 0   | 0   | 0   | 0   |
| T7  | 500 | 10  | 10  | 10  | 0   | 20  | 0   |
| T10 | 250 | 10  | 10  | 20  | 0   | 30  | 30  |
| T12 | 500 | 10  | 20  | 10  | 20  | 0   | 30  |
| T14 | 250 | 90  | 60  | 100 | 100 | 70  | 90  |
| T15 | 250 | 70  | 10  | 10  | 20  | 30  | 90  |
| T21 | 250 | 90  | 70  | 90  | 100 | 100 | 100 |
| T22 | 250 | 100 | 100 | 100 | 100 | 100 | 100 |
| T23 | 500 | 100 | 90  | 90  | 100 | 100 | 100 |
| T24 | 250 | 90  | 60  | 90  | 100 | 100 | 100 |
| T25 | 250 | 90  | 90  | 100 | 100 | 100 | 100 |
| T26 | 250 | 90  | 60  | 70  | 100 | 100 | 80  |
| T27 | 250 | 70  | 60  | 90  | 100 | 100 | 70  |
| T28 | 250 | 100 | 100 | 100 | 100 | 100 | 100 |
| T30 | 250 | 10  | 30  | 40  | 70  | 60  | 80  |
| P1  | 250 | 30  | 0   | 30  | 0   | 0   | 20  |
| P2  | 250 | 30  | 0   | 50  | 0   | 0   | 50  |

Post-Emergence Activity

| Compound Number | Rate g/ha | ALOMY | AVEFA | LOLPE | SETFA | DIGSA | ECHCG |
|---|---|---|---|---|---|---|---|
| T4  | 125 | 10  | 30  | 40  | 40  | 60  | 80  |
| T5  | 125 | 10  | 10  | 0   | 10  | 30  | 0   |
| T6  | 125 | 10  | 10  | 10  | 40  | 20  | 30  |
| T7  | 125 | 0   | 0   | 0   | 0   | 0   | 50  |
| T10 | 125 | 10  | 40  | 20  | 60  | 40  | 60  |
| T12 | 125 | 80  | 80  | 30  | 70  | 80  | 80  |
| T14 | 125 | 90  | 100 | 80  | 80  | 60  | 100 |
| T15 | 125 | 50  | 40  | 40  | 70  | 40  | 90  |
| T21 | 125 | 50  | 20  | 40  | 80  | 80  | 100 |
| T22 | 125 | 70  | 70  | 20  | 60  | 100 | 100 |
| T23 | 125 | 100 | 100 | 100 | 100 | 100 | 100 |
| T24 | 125 | 70  | 70  | 30  | 80  | 90  | 100 |
| T25 | 125 | 100 | 100 | 50  | 90  | 100 | 100 |
| T26 | 125 | 10  | 0   | 0   | 0   | 30  | 0   |
| T27 | 125 | 80  | 90  | 40  | 80  | 100 | 100 |
| T28 | 125 | 70  | 70  | 50  | 80  | 100 | 100 |
| T30 | 125 | 0   | 10  | 20  | 40  | 70  | 70  |
| P1  | 125 | 70  | 80  | 60  | 90  | 80  | 100 |
| P2  | 125 | 90  | 90  | 70  | 80  | 80  | 100 |

Pre-Emergence Activity

| Compound Number | Rate g/ha | AMARE | SETFA | ALOMY | ECHCG | AVEFA |
|---|---|---|---|---|---|---|
| T20 | 250 | 0 | 80 | 50 | 70 | 60 |
| T29 | 250 | 20 | 90 | 50 | 90 | 90 |
| T31 | 250 | 20 | 90 | 60 | 90 | 70 |
| T32 | 250 | 0 | 40 | 0 | 0 | 0 |
| T33 | 250 | 0 | 100 | 90 | 100 | 0 |
| T34 | 250 | 0 | 90 | 40 | 70 | 20 |
| T35 | 250 | 0 | 100 | 100 | 100 | 100 |
| T36 | 250 | 0 | 100 | 90 | 100 | 80 |
| T37 | 250 | 0 | 90 | 30 | 40 | 0 |
| T38 | 250 | 0 | 90 | 0 | 40 | 0 |
| T39 | 250 | 0 | 90 | 70 | 80 | 90 |
| T40 | 250 | 0 | 100 | 90 | 100 | 40 |
| T41 | 250 | 0 | 100 | 100 | 100 | 30 |
| T42 | 250 | 0 | 100 | 90 | 90 | 30 |
| T43 | 250 | 0 | 60 | 0 | 80 | 0 |
| T45 | 250 | 0 | 100 | 90 | 100 | 60 |
| T47 | 250 | 0 | 100 | 90 | 90 | 80 |
| T48 | 250 | 0 | 90 | 40 | 70 | 20 |
| T49 | 250 | 0 | 90 | 20 | 70 | 0 |
| T50 | 250 | 0 | 90 | 40 | 90 | 0 |
| T51 | 250 | 0 | 100 | 80 | 100 | 90 |
| T52 | 250 | 0 | 100 | 70 | 100 | 90 |
| T53 | 250 | 90 | 90 | 50 | 80 | 70 |
| T54 | 250 | 0 | 100 | 90 | 100 | 100 |
| P4 | 250 | 0 | 90 | 60 | 90 | 90 |
| P5 | 250 | 0 | 100 | 50 | 90 | 70 |
| P6 | 250 | 0 | 70 | 0 | 20 | 0 |
| P7 | 250 | 0 | 100 | 100 | 100 | 100 |
| P8 | 250 | 0 | 100 | 90 | 100 | 30 |
| P9 | 250 | 0 | 90 | 70 | 90 | 50 |
| P10 | 250 | 0 | 100 | 90 | 100 | 100 |

Post-Emergence Activity

| Compound Number | Rate g/ha | AMARE | SETFA | ALOMY | ECHCG | AVEFA |
|---|---|---|---|---|---|---|
| P34 | 250 | 0 | 100 | 100 | 100 | 80 |
| T17 | 1000 | 70 | 100 | 100 | 100 | 100 |
| T18 | 1000 | 0 | 40 | 20 | 20 | 0 |
| T19 | 1000 | 20 | 30 | 10 | 0 | 0 |
| T20 | 250 | 0 | 100 | 90 | 100 | 100 |
| T21 | 1000 | 0 | 100 | 100 | 100 | 100 |
| T29 | 250 | 0 | 100 | 100 | 100 | 100 |
| T31 | 250 | 0 | 70 | 60 | 80 | 50 |
| T32 | 250 | 0 | 70 | 0 | 30 | 0 |
| T33 | 250 | 60 | 100 | 100 | 100 | 100 |
| T35 | 250 | 0 | 100 | 100 | 100 | 100 |
| T36 | 250 | 30 | 100 | 100 | 100 | 100 |
| T37 | 250 | 0 | 90 | 50 | 90 | 10 |
| T38 | 250 | 0 | 100 | 90 | 100 | 90 |
| T39 | 250 | 0 | 100 | 100 | 100 | 100 |
| T40 | 250 | 0 | 100 | 100 | 100 | 70 |
| T41 | 250 | 0 | 100 | 100 | 100 | 90 |
| T42 | 250 | 0 | 100 | 100 | 100 | 100 |
| T43 | 250 | 0 | 100 | 90 | 100 | 100 |
| T45 | 250 | 0 | 100 | 100 | 100 | 100 |
| T47 | 250 | 0 | 100 | 100 | 100 | 100 |
| T48 | 250 | 40 | 90 | 60 | 100 | 40 |
| T49 | 250 | 0 | 90 | 50 | 100 | 30 |
| T50 | 250 | 0 | 100 | 90 | 100 | 90 |
| T51 | 250 | 0 | 90 | 90 | 100 | 80 |
| T52 | 250 | 0 | 100 | 100 | 100 | 100 |
| T53 | 250 | 0 | 100 | 60 | 90 | 70 |
| T54 | 250 | 40 | 100 | 100 | 100 | 100 |
| P3 | 250 | 0 | 100 | 100 | 100 | 100 |
| P4 | 250 | 0 | 100 | 100 | 100 | 100 |
| P5 | 250 | 0 | 100 | 90 | 100 | 90 |
| P6 | 250 | 0 | 100 | 90 | 100 | 90 |
| P7 | 250 | 0 | 100 | 100 | 100 | 100 |
| P8 | 250 | 0 | 100 | 100 | 100 | 100 |
| P9 | 250 | 0 | 100 | 100 | 100 | 90 |
| P10 | 250 | 20 | 100 | 100 | 100 | 100 |

What is claimed is:

1. A compound of the formula (I)

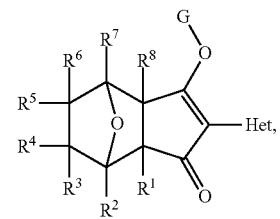

and tautomeric forms thereof, wherein $R^1$ and $R^8$ are independently of each other hydrogen, $C_1$-$C_3$alkyl, $C_1$-$C_3$haloalkyl, $C_1$-$C_3$alkoxy, $C_1$-$C_3$alkylthio, halogen or $C_1$-$C_6$alkoxycarbonyl, $R^2$ and $R^7$ are independently of each other hydrogen, halogen, cyano, $C_1$-$C_6$alkyl or a group $COR^9$, $CO_2R^{10}$ or $CONR^{11}R^{12}$, $CR^{13}$=$NOR^{14}$ or $CR^{15}$=$NNR^{16}R^{17}$;

$R^3$, $R^4$, $R^5$ and $R^6$ are independently of each other hydrogen, cyano, $C_1$-$C_6$alkyl, $C_2$-$C_6$alkenyl, $C_1$-$C_6$alkoxy, $C_1$-$C_6$alkoxy$C_1$-$C_6$alkyl, 3-7 membered heterocycyl or $CR^{13}$=$NOR^{14}$;

wherein $R^9$, $R^{10}$, $R^{11}$ and $R^{12}$ are $C_1$-$C_6$alkyl, $R^{13}$ and $R^{15}$ are hydrogen or $C_1$-$C_3$ alkyl, $R^{14}$ is $C_1$-$C_3$ alkyl, and $R^{16}$ and $R^{17}$ are independently of each other hydrogen or $C_1$-$C_3$alkyl;

or $R^3$ and $R^4$ together with the carbon atoms to which they are attached form a keto, imino or alkenyl unit, or $R^3$ and $R^6$ together form a bond, G is hydrogen or an alkali metal, alkaline earth metal, sulfonium, ammonium or a latentiating group, Het is a group of the formula $R_1$ to $R_{12}$

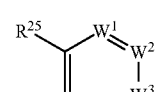

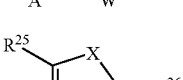

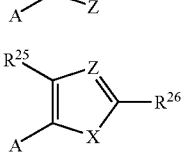

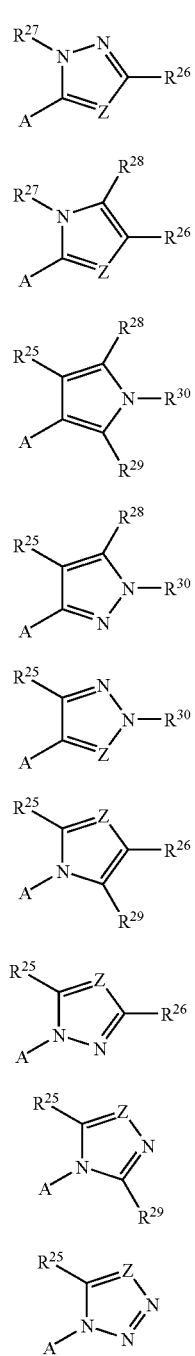

wherein

A designates the point of attachment to the ketoenol moiety, $W^1$ is N or $CR^{28}$, $W^2$ and $W^3$ are independently of each other N or $CR^{26}$, $W^4$ is N or $CR^{29}$, with the proviso that at least one of $W^1$, $W^2$, $W^3$ or $W^4$ is N, X is O, S, Se, or $NR^{31}$, Z is N or $CR^{32}$, wherein $R^{25}$ is hydrogen, halogen, $C_1$-$C_4$alkyl, $C_1$-$C_4$haloalkyl, $C_3$-$C_6$-cycloalkyl, $C_3$-$C_6$-halocycloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, nitro or cyano, preferably halogen, $C_1$-$C_2$alkyl, $C_1$-$C_2$haloalkyl, vinyl, ethynyl, or methoxy, $R^{26}$ is optionally substituted aryl or optionally substituted heteroaryl wherein the substituents are selected from halogen $C_1$-$C_2$-alkyl, $C_1$-$C_2$-alkoxy, $C_1$-$C_2$ haloalkyl, $C_1$-$C_2$ haloalkoxy, cyano or nitro, $R^{27}$ is hydrogen, $C_1$-$C_4$ alkyl, $C_1$-$C_4$ haloalkyl, $C_3$-$C_6$-cycloalkyl, $C_3$-$C_6$-halocycloalkyl, $C_2$-$C_3$alkenyl, $C_2$-$C_3$alkynyl, $C_1$-$C_4$ haloalkyl or $C_2$-$C_3$ haloalkenyl, $R^{28}$ is hydrogen, methyl, halomethyl or halogen, $R^{29}$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl or cyano, $R^{30}$ is optionally substituted aryl or optionally substituted heteroaryl wherein the substituents are selected from halogen $C_1$-$C_2$-alkyl, $C_1$-$C_2$-alkoxy, $C_1$-$C_2$ haloalkyl, $C_1$-$C_2$ haloalkoxy, cyano or nitro, $R^{31}$ is hydrogen, methyl, ethyl or halomethyl, and $R^{32}$ is hydrogen, methyl, ethyl, halomethyl, haloethyl, halogen, cyano or nitro;

and agronomically acceptable salts of compounds of formula I and of said tautomeric forms.

2. A compound according to claim 1, wherein $R^3$ and $R^6$ together form a bond.

3. A compound according to claim 1, wherein $R^1$ and $R^8$ are independently of each other hydrogen or $C_1$-$C_3$alkyl.

4. A compound according to claim 1, wherein $R^1$ and $R^8$ together with the carbon atoms to which they are attached form a 3-7 membered ring, optionally containing an oxygen or sulphur atom.

5. A compound according to claim 1, wherein G denotes hydrogen, an alkali metal cation, alkaline earth metal cation, sulfonium cation or ammonium cation, or $C_1$-$C_6$alkyl, $C_3$-$C_6$alkenyl or $C_3$-$C_6$alkynyl or a latentiating group.

6. A compound according to claim 1, wherein $R^1$ to $R^8$ and G are hydrogen, Het is a group $R_2$

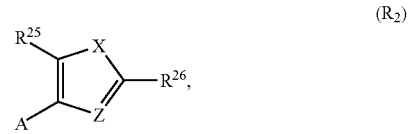

wherein A designates the point of attachment to the ketoenol moiety, X is S, Z is N, $R^{25}$ is methyl or ethyl and $R^{26}$ is 4-chlorophenyl or 4-bromophenyl.

7. A herbicidal composition comprising; a formulation assistant, and a herbicidally effective amount of a compound of formula (I), according to claim 1.

8. A composition according to claim 7 further comprising a second herbicide, optionally a third herbicide, and optionally a safener.

9. A method of controlling grasses and weeds in crops of useful plants, which comprises applying a herbicidally effective amount of a compound of formula (I) according to claim 1, or of a composition comprising such a compound, to the plants or to a locus thereof.

10. A compound according to claim 1 wherein $R^2$ and $R^7$ are independently of each other hydrogen, methyl or methyl substituted by $C_1$-$C_3$alkoxy.

11. A compound according to claim 1, wherein $R^3$ and $R^4$ together form a unit $=O$ or $=NR^{23}$, wherein $R^{23}$ is $C_1$-$C_3$alkoxy.

12. A compound according to claim 1, wherein Het is a group of formula $R_2$

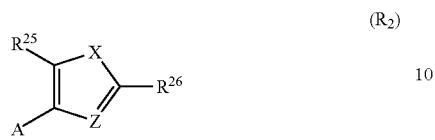

($R_2$)

wherein A designates the point of attachment to the ketoenol moiety, wherein X is S and Z is N and $R^{25}$ and $R^{26}$ are as defined in claim 1.

13. A compound according to claim 1, wherein Het is a group of formula $R_2$

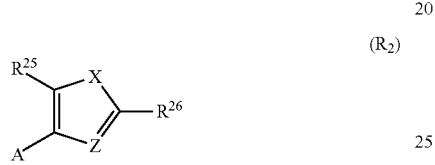

($R_2$)

wherein A designates the point of attachment to the ketoenol moiety, X is S and Z is $CR^{32}$ and $R^{25}$, $R^{26}$ and $R^{32}$ are as defined in claim 1.

* * * * *